(12) United States Patent
Volkov et al.

(10) Patent No.: US 7,668,697 B2
(45) Date of Patent: Feb. 23, 2010

(54) METHOD FOR ANALYZING DYNAMIC DETECTABLE EVENTS AT THE SINGLE MOLECULE LEVEL

(76) Inventors: Andrei Volkov, 4010 Linkwood Dr., #1064, Houston, TX (US) 77025; Costa M. Colbert, 2234 McClendon, Houston, TX (US) 77030; Ivan Pan, 3035 W. Hampton Dr., Houston, TX (US) 77082; Anelia Kraltcheva, 14230 Wenderlich Dr., #153, Houston, TX (US) 77069; Mitsu Reddy, 2203 Lake Wind Dr., Pearland, TX (US) 77584; Nasanshargal Battulga, VisiGen Biotechnologies, Inc., 2575 W. Bellfort, Suite 250, Houston, TX (US) 77054; Michael A. Rea, 13935 Hidden Lake Ln., Sugarland, TX (US) 77478; Keun Woo Lee, 900 Gazwa-dong, Jinju, GN 660-701 (KR); Susan H. Hardin, 4712 Nantucket Dr., College Station, TX (US) 77845; Brent Mulder, 3720 Ponca Ct., SW., Grandville, MI (US) 49418; Chris Hebel, 17006 Quiet Dale Ct., Houston, TX (US) 77095; Alok Bandekar, 7777 Cambridge #7777, Houston, TX (US) 77059

( * ) Notice: Subject to any disclaimer, the term of this patent is extended or adjusted under 35 U.S.C. 154(b) by 0 days.

(21) Appl. No.: 11/671,956

(22) Filed: Feb. 6, 2007

(65) Prior Publication Data

US 2007/0250274 A1 Oct. 25, 2007

Related U.S. Application Data

(63) Continuation-in-part of application No. 10/007,621, filed on Dec. 3, 2001, now Pat. No. 7,211,414, and a continuation-in-part of application No. 09/901,782, filed on Jul. 3, 2001.

(60) Provisional application No. 60/765,693, filed on Feb. 6, 2006.

(51) Int. Cl.
$G06F\ 19/00$ (2006.01)
$G06F\ 17/40$ (2006.01)
$G01N\ 33/00$ (2006.01)

(52) U.S. Cl. .................. 702/187; 382/128; 382/129; 702/19; 702/20; 702/27

(58) Field of Classification Search ............... 382/100, 382/128, 129, 130, 133; 702/1, 19, 20, 21, 702/22, 27, 28, 127, 187, 189, 190, 199
See application file for complete search history.

(56) References Cited

U.S. PATENT DOCUMENTS 4,711,955 A 12/1987 Ward et al. ............... 536/25.32

(Continued)

FOREIGN PATENT DOCUMENTS

EP 745686 12/1996

(Continued)

OTHER PUBLICATIONS

Rosenblum et al: "New dye-labeled terminators for improved DNA sequencing patterns" @ 1997 Oxford University Press, Nucleic Acids Research, 1997, vol. 25, No. 22, pp. 4500-4504.*

(Continued)

Primary Examiner—Edward R Cosimano
(74) Attorney, Agent, or Firm—Robert C. Klinger; Technology Corporation

(57) ABSTRACT

A method to be implemented on or in a computer is disclosed, where the method includes data collection, calibration, candidate selection, and analysis of data streams associated with each candidate to classify single molecule fluorescence resonance energy transfer events. Once classified, the classifications correlate to the nature of the events, such as the identification of dNTP incorporation during primer extension to obtain a base read out of an unknown template.

28 Claims, 34 Drawing Sheets

U.S. PATENT DOCUMENTS

| | | | | |
|---|---|---|---|---|
| 4,994,373 A | 2/1991 | Stavrianopoulos et al. | | 435/6 |
| 4,997,928 A | 3/1991 | Hobbs | | 536/24.3 |
| 5,200,313 A | 4/1993 | Carrico | | 435/6 |
| 5,230,781 A | 7/1993 | Middendorf et al. | | 204/461 |
| 5,241,060 A | 8/1993 | Englehardt et al. | | 536/25.32 |
| 5,302,509 A | 4/1994 | Cheeseman | | 435/6 |
| 5,360,523 A | 11/1994 | Middendorf et al. | | 204/457 |
| 5,366,603 A | 11/1994 | Middendorf et al. | | 204/461 |
| 5,403,708 A | 4/1995 | Brennan et al. | | 435/6 |
| 5,405,747 A | 4/1995 | Jett et al. | | 435/6 |
| 5,470,710 A | 11/1995 | Weiss et al. | | 435/6 |
| 5,512,462 A | 4/1996 | Cheng | | 435/91.2 |
| 5,534,125 A | 7/1996 | Middendorf et al. | | 204/618 |
| 5,547,835 A | 8/1996 | Koster | | 435/6 |
| 5,571,388 A | 11/1996 | Patonay et al. | | 204/461 |
| 5,601,982 A | 2/1997 | Sargent et al. | | 435/6 |
| 5,620,854 A | 4/1997 | Holzrichter et al. | | 435/6 |
| 5,631,134 A | 5/1997 | Cantor | | 435/6 |
| 5,639,874 A | 6/1997 | Middendorf et al. | | 536/25.32 |
| 5,646,264 A | 7/1997 | Glazer et al. | | 536/25.32 |
| 5,661,028 A | 8/1997 | Foote | | 435/287.2 |
| 5,677,196 A | 10/1997 | Herron et al. | | 436/518 |
| 5,688,648 A | 11/1997 | Mathies et al. | | 435/6 |
| 5,695,934 A | 12/1997 | Brenner | | 435/6 |
| 5,703,222 A | 12/1997 | Grossman et al. | | 536/24.3 |
| 5,723,298 A | 3/1998 | Oommen et al. | | 435/6 |
| 5,755,943 A | 5/1998 | Middendorf et al. | | 204/467 |
| 5,800,995 A | 9/1998 | Patonay et al. | | 435/6 |
| 5,846,727 A | 12/1998 | Soper et al. | | 435/6 |
| 5,858,671 A | 1/1999 | Jones | | 435/6 |
| 5,922,591 A | 7/1999 | Anderson et al. | | 435/287.2 |
| 5,961,923 A | 10/1999 | Nova et al. | | 506/4 |
| 5,972,603 A | 10/1999 | Bedford et al. | | 435/6 |
| 6,004,446 A | 12/1999 | Middendorf et al. | | 204/618 |
| 6,004,744 A | 12/1999 | Goelet et al. | | 435/5 |
| 6,027,709 A | 2/2000 | Little et al. | | 424/1.65 |
| 6,027,890 A | 2/2000 | Ness et al. | | 506/9 |
| 6,048,690 A | 4/2000 | Heller et al. | | 435/6 |
| 6,086,737 A | 7/2000 | Patonay et al. | | 204/461 |
| 6,143,151 A | 11/2000 | Middendorf et al. | | 204/451 |
| 6,207,421 B1 | 3/2001 | Middendorf et al. | | 435/91.1 |
| 6,210,896 B1 | 4/2001 | Chan | | 435/6 |
| 6,221,592 B1 | 4/2001 | Schwartz et al. | | 435/6 |
| 6,232,075 B1 | 5/2001 | Williams | | 435/6 |
| 6,255,083 B1 | 7/2001 | Williams | | 435/91.1 |
| 6,263,286 B1 | 7/2001 | Gilmanshin et al. | | 702/19 |
| 6,280,939 B1 | 8/2001 | Allen | | 435/6 |
| 6,306,607 B2 | 10/2001 | Williams | | 435/6 |
| 6,329,178 B1 | 12/2001 | Patel et al. | | |
| 6,355,420 B1 | 3/2002 | Chan | | 435/6 |
| 6,399,335 B1 | 6/2002 | Kao et al. | | 435/91.1 |
| 6,403,311 B1 | 6/2002 | Chan | | 435/6 |
| 6,485,944 B1 | 11/2002 | Church et al. | | 435/91.2 |
| 6,524,829 B1 | 2/2003 | Seeger | | 435/91.2 |
| 6,593,148 B1 | 7/2003 | Narayanan | | 436/546 |
| 6,762,048 B2 | 7/2004 | Williams | | 435/287.1 |
| 6,936,702 B2 | 8/2005 | Williams et al. | | 536/22.1 |
| 6,982,146 B1 | 1/2006 | Schneider et al. | | |
| 6,995,274 B2 | 2/2006 | Lugade et al. | | 548/427 |
| 7,005,518 B2 | 2/2006 | Peng et al. | | 540/145 |
| 7,033,762 B2 | 4/2006 | Nelson et al. | | |
| 7,037,687 B2 | 5/2006 | Williams et al. | | |
| 7,041,812 B2 | 5/2006 | Kumar et al. | | |
| 7,118,907 B2 | 10/2006 | Williams et al. | | 435/287.1 |
| 7,125,671 B2 | 10/2006 | Sood et al. | | |
| 7,130,041 B2 | 10/2006 | Bouzid et al. | | 356/303 |
| 7,223,541 B2 | 5/2007 | Fuller et al. | | |
| 7,229,799 B2 | 6/2007 | Williams | | 435/91.2 |
| 7,270,951 B1 | 9/2007 | Stemple et al. | | |
| 7,280,205 B2 | 10/2007 | Bouzid et al. | | 356/326 |
| 7,286,232 B2 | 10/2007 | Bouzid | | 356/417 |
| 2001/0014850 A1 | 8/2001 | Gilmanshin et al. | | 702/19 |
| 2002/0025529 A1 | 2/2002 | Quake et al. | | 435/6 |
| 2002/0115076 A1 | 8/2002 | Williams | | 435/6 |
| 2002/0164629 A1 | 11/2002 | Quake et al. | | 435/6 |
| 2002/0168678 A1 | 11/2002 | Williams et al. | | 435/6 |
| 2003/0044781 A1 | 3/2003 | Korlach et al. | | 435/6 |
| 2003/0064366 A1 | 4/2003 | Hardin et al. | | 435/6 |
| 2003/0064400 A1 | 4/2003 | Williams | | 435/6 |
| 2003/0134807 A1 | 7/2003 | Hardin et al. | | 514/44 |
| 2003/0174992 A1 | 9/2003 | Levene et al. | | 385/129 |
| 2003/0186255 A1 | 10/2003 | Williams et al. | | 506/16 |
| 2003/0194740 A1 | 10/2003 | Williams et al. | | 435/6 |
| 2004/0015964 A1 | 1/2004 | McCann et al. | | 717/178 |
| 2004/0161741 A1 | 8/2004 | Rabani et al. | | 435/6 |
| 2004/0171827 A1 | 9/2004 | Peng et al. | | 540/145 |
| 2004/0259082 A1 | 12/2004 | Williams | | 435/6 |
| 2005/0042633 A1 | 2/2005 | Williams | | 435/6 |
| 2005/0158761 A1 | 7/2005 | Korlach et al. | | 435/6 |
| 2005/0164255 A1 | 7/2005 | Korlach et al. | | 435/6 |
| 2005/0186619 A1 | 8/2005 | Korlach et al. | | 435/6 |
| 2005/0202466 A1 | 9/2005 | Korlach et al. | | 435/6 |
| 2005/0208557 A1 | 9/2005 | Korlach et al. | | 435/6 |
| 2005/0257611 A1 | 11/2005 | Fogal et al. | | 73/152.22 |
| 2005/0260614 A1 | 11/2005 | Hardin et al. | | 435/6 |
| 2005/0266424 A1 | 12/2005 | Hardin et al. | | 435/6 |
| 2005/0266456 A1 | 12/2005 | Williams et al. | | 435/6 |
| 2005/0276535 A1 | 12/2005 | Levene et al. | | 385/12 |
| 2006/0057606 A1 | 3/2006 | Korlach et al. | | 435/6 |
| 2006/0060766 A1 | 3/2006 | Turner et al. | | 250/251 |
| 2006/0061754 A1 | 3/2006 | Turner et al. | | 356/38 |
| 2006/0061755 A1 | 3/2006 | Turner et al. | | 356/38 |
| 2006/0062531 A1 | 3/2006 | Turner et al. | | 385/123 |
| 2006/0063173 A1 | 3/2006 | Williams et al. | | 435/6 |
| 2006/0063247 A1 | 3/2006 | Lugade et al. | | 435/183 |
| 2006/0063264 A1 | 3/2006 | Turner | | 436/8 |
| 2006/0078937 A1 | 4/2006 | Korlach et al. | | 435/6 |
| 2006/0134666 A1 | 6/2006 | Korlach et al. | | 435/6 |
| 2006/0154288 A1 | 7/2006 | Korlach et al. | | 435/6 |
| 2006/0160113 A1 | 7/2006 | Korlach et al. | | 435/6 |
| 2006/0172313 A1 | 8/2006 | Buzby | | |
| 2006/0188900 A1 | 8/2006 | Korlach et al. | | 435/6 |
| 2006/0194232 A1 | 8/2006 | Turner et al. | | 435/6 |
| 2006/0197949 A1 | 9/2006 | Bouzid et al. | | 356/328 |
| 2006/0211010 A1 | 9/2006 | Korlach et al. | | 435/6 |
| 2006/0280688 A1 | 12/2006 | Kovar et al. | | 424/9.6 |
| 2007/0036502 A1 | 2/2007 | Levene et al. | | 385/132 |
| 2007/0042398 A1 | 2/2007 | Peng et al. | | 435/6 |
| 2007/0044538 A1 | 3/2007 | Johnson et al. | | 73/19.01 |
| 2007/0048748 A1 | 3/2007 | Williams et al. | | 435/6 |
| 2007/0134128 A1 | 6/2007 | Korlach et al. | | 422/56 |
| 2007/0134716 A1 | 6/2007 | Levene | | 385/12 |
| 2007/0172819 A1 | 7/2007 | Hardin et al. | | 539/24.3 |
| 2007/0172858 A1 | 7/2007 | Hardin et al. | | |
| 2007/0172859 A1 | 7/2007 | Hardin et al. | | 435/6 |
| 2007/0172860 A1 | 7/2007 | Hardin et al. | | 435/912 |
| 2007/0172861 A1 | 7/2007 | Hardin et al. | | |
| 2007/0172862 A1 | 7/2007 | Hardin et al. | | |
| 2007/0172863 A1 | 7/2007 | Hardin et al. | | |
| 2007/0172864 A1 | 7/2007 | Gao et al. | | |
| 2007/0172865 A1 | 7/2007 | Hardin et al. | | |
| 2007/0172866 A1 | 7/2007 | Hardin et al. | | |
| 2007/0172867 A1 | 7/2007 | Hardin et al. | | |
| 2007/0172868 A1 | 7/2007 | Hardin et al. | | |
| 2007/0172869 A1 | 7/2007 | Hardin et al. | | |
| 2007/0184475 A1 | 8/2007 | Hardin et al. | | |
| 2007/0250274 A1 | 10/2007 | Volkov et al. | | 702/22 |
| 2007/0275395 A1 | 11/2007 | Hardin et al. | | 435/6 |
| 2007/0292867 A1 | 12/2007 | Hardin et al. | | 435/6 |

FOREIGN PATENT DOCUMENTS

| | | |
|---|---|---|
| EP | 0258017 B1 | 6/1997 |
| EP | 834576 | 6/1999 |

| | | |
|---|---|---|
| WO | WO 90/13666 | 11/1990 |
| WO | WO 91/13075 | 9/1991 |
| WO | WO 93/21340 | 10/1993 |
| WO | WO 95/06138 | 3/1995 |
| WO | WO96/27025 | 9/1996 |
| WO | WO 98/22615 | 5/1998 |
| WO | WO-98/31834 | 7/1998 |
| WO | WO 98/31834 | 7/1998 |
| WO | WO199840496 | 9/1998 |
| WO | WO 98/44152 | 10/1998 |
| WO | WO 99/05315 | 2/1999 |
| WO | WO-99/05315 | 2/1999 |
| WO | WO 99/19341 | 4/1999 |
| WO | WO 99/53034 | 10/1999 |
| WO | WO 00/06770 | 2/2000 |
| WO | WO-00/06770 | 2/2000 |
| WO | WO-00/09757 | 2/2000 |
| WO | WO-00/17330 | 3/2000 |
| WO | WO 00/17330 | 3/2000 |
| WO | WO 00/36151 | 6/2000 |
| WO | WO-00/36151 | 6/2000 |
| WO | WO 00/36152 | 6/2000 |
| WO | WO-00/40750 | 7/2000 |
| WO | WO-00/53805 | 9/2000 |
| WO | WO-00/53812 | 9/2000 |
| WO | WO-00/58507 | 10/2000 |
| WO | WO-00/60072 | 10/2000 |
| WO | WO-00/60114 | 10/2000 |
| WO | WO 00/60114 | 10/2000 |
| WO | WO-00/67698 | 11/2000 |
| WO | WO-00/70073 | 11/2000 |
| WO | WO 00 70073 A | 11/2000 |
| WO | WO-01/13088 | 2/2001 |
| WO | WO-01/16375 | 3/2001 |
| WO | WO 01/16375 | 3/2001 |
| WO | WO 01/23610 | 4/2001 |
| WO | WO-01/23610 | 4/2001 |
| WO | WO 01/25480 | 4/2001 |
| WO | WO-01/25480 | 4/2001 |
| WO | WO-01/32930 | 5/2001 |
| WO | WO-01/57248 | 8/2001 |
| WO | WO-01/57249 | 8/2001 |
| WO | WO-01/94609 | 12/2001 |
| WO | WO-02/02813 | 1/2002 |
| WO | WO-02/03305 | 1/2002 |
| WO | WO 02/04680 A2 | 1/2002 |
| WO | WO-02/29106 | 4/2002 |
| WO | WO-02/061126 | 8/2002 |
| WO | WO-02/061127 | 8/2002 |
| WO | WO-02/072892 | 9/2002 |
| WO | WO-02/095070 | 11/2002 |
| WO | WO-02/101095 | 12/2002 |
| WO | WO-03/016565 | 2/2003 |
| WO | WO-03/020734 | 3/2003 |
| WO | WO2004020604 | 3/2004 |
| WO | WO2004072297 | 8/2004 |
| WO | WO2004072304 | 8/2004 |

OTHER PUBLICATIONS

Ambrose et al: "Single-Molecule Detection With Total Internal Reflection Excitation: Comparing Signal-to-Background and Total Signals in Different Geometries", @ 1999 Wiley-Liss, Inc. Cytometry 36:224-231 (1999).*

Agrawal, Sudhir et al., "Site-specific functionalization of oligodeoxynucleotides for non-radioactive labelling", *Tetrahedron Letters* vol. 31, No. 11 1990, 1543-1546.

Allen, Beth L. et al., "DNA recognition properties of the N-terminal DNA binding domain within the large subunit of replication factor C", *Nucleic Acids Research* vol. 26, No. 17 Sep. 1998, 3877-3882.

Ambrose, W P. et al., "Alterations of Single Molecule Fluorescence Lifetimes in Near-Field Optical Microscopy", *Science* vol. 265 Jul. 15, 1994, 364-367.

Arion, Dominique et al., "HIV resistance to zidovudine: the role of pyrophosphorolysis", *Drug Resistance Updates* vol. 2, No. 2 Apr. 1999, 91-95.

Asanov, Alexander N. et al., "Regenerable Biosensor Platform: A Total Internal Reflection Fluorescence Cell with Electrochemical Control", *Analytical Chemistry* vol. 70, No. 6 Mar. 15, 1998, 1156-1163.

Bains, William et al., "A Novel Method for Nucleic Acid Sequence Determination", *Journal of Theoretical Biology* vol. 135 Dec. 7, 1988, 303-307.

Ball, S, "The use of tailed octamer primers for cycle sequencing", *Nucleic Acids Research* vol. 26, No. 22 Nov. 1998, 5225-5227.

Basche, TH, "Photon antibunching in the fluorescence of a single dye molecule trapped in a solid", *Physical Review Letters* vol. 69, No. 10 Sep. 7, 1992, 1516-1519.

Bedford, Ella et al., "The thioredoxin binding domain of bacteriophage T7 DNA polymerase confers processivity on *Escherichia coli* DNA polymerase I", *Proceedings of the National Academy of Sciences (PNAS)* vol. 94, No. 2 Jan. 21, 1997, 479-484.

Bonnaffe, D et al., "Synthesis of acyl pyrophosphates. Application to the synthesis of nucleotide lipophilic prodrugs", *Tetrahedron Letters* vol. 36, No. 4 Jan. 23, 1995, 531-534.

Brouwer, A.C.J. et al., "Single-molecule fluorescence autocorrelation experiments on pentacene: The dependence of intersystem crossing on isotopic composition", *Journal of Chemical Physics* vol. 110, No. 18 1999, 9151-9159.

Brownstein, Michael J. et al., "Modulation of Non-Templated Nucleotide Addition by Taq DNA Polymerase: Primer Modifications that Facilitate Genotyping", *Biotechniques* vol. 20, No. 6 Jun. 1996, 1004-1010.

Burbelo, Peter D. et al., "Rapid Plasmid DNA Sequencing with Multiple Octamer Primers", *BioTechniques* vol. 16, No Apr. 1994, 645-650.

Castro, Alonso et al., "Single-Molecule Detection of Specific Nucleic Acid Sequences in Unamplified Genomic DNA", *Analytical Chemistry* vol. 69, No. 19 Oct. 1, 1997, 3915-3920.

Church, George M. et al., "Multiplex DNA sequencing", *Science* vol. 240, No. 4849 Apr. 8, 1988, 185-188.

Clegg, Robert M. et al., "Observing the Helical Geometry of Double-Stranded DNA in Solution by Fluorescence Resonance Energy Transfer", *Proceedings of the National Academy of Sciences (PNAS)* vol. 90: National Academy of Sciences of the USA Apr. 1993, 2994-2998.

Cline, Janice et al., "PCR Fidelity of Pfu DNA Polymerase and Other Thermostable DNA Polymerases", *Nucleic Acids Research* vol. 24, No. 18, Oxford University Press Sep. 1996, 3546-3551.

Collins, Francis S. et al., "New Goals for the U.S. Human Genome Project: 1998-2003", *Science* vol. 282 Oct. 23, 1998, 682-689.

Cross, Collin W. et al., "Solution Structure of an RNA•DNA Hybrid Duplex Containing a 3'-Thioformacetal Linker and an RNA A-Tract", *Biochemistry* vol. 36, No. 14 Apr. 8, 1997, 4096-4107.

Davis, Lloyd M. et al., "Rapid DNA Sequencing Based On Single Molecule Detection", *Los Alamos Science* vol. 20 1992, 281-285.

Davis, Lloyd M. et al., "Rapid DNA sequencing based upon single molecule detection.", *Genetic Analysis, Techniques and Applications* vol. 8, No. 1 Feb. 1991, 1-7.

Dobrikov, M I. et al., "Sensitized Photomodification of Single-Stranded DNA by a Binary System of Oligonucleotide Conjugates", *Antisense and Nucleic Acid Drug Development* vol. 7, No. 4 1997, 309-317.

Doore, Klaus et al., "Techniques for Single Molecule Sequencing", *Bioimaging* vol. 5, No. 3 Sep. 1997, 139-152.

Driscoll, Robert J. et al., "Atomic-scale imaging of DNA using scanning tunnelling microscopy", *Nature* vol. 346 Jul. 19, 1990, 294-296.

Eckert, Kristin A. et al., "High fidelity DNA synthesis by the *Thermus aquaticus* DNA polymerase", *Nucleic Acids Research* vol. 18, No. 13 1990, 3739-3744.

Edman, Lars et al., "Conformational transitions monitored for single molecules in solution", *Proceedings of the National Academy of Sciences (PNAS)* vol. 93, No. 13 Jun. 25, 1996, 6710-6715.

Eggeling, C, "Monitoring conformational dynamics of a single molecule by selective fluorescence spectroscopy", *Proceedings of the National Academy of Sciences (PNAS)* vol. 95, No. 4 Feb. 17, 1998, 1556-1561.

Eigen, Manfred, "The fifth Paul Ehrlich lecture virus strains as models of molecular evolution", *Medicinal Research Reviews* vol. 13, No. 4 (XP000430626) Jul. 1993, 385-398.

Eom, Soo H. et al., "Structure of Taq polymerase with DNA at the polymerase active site", *Nature* vol. 382, Macmillan Journals Ltd. Jul. 18, 1996, 278-281.

Ewing, Brent et al., "Base-Calling of Automated Sequencer Traces Using Phred. I. Accuracy Assessment", *Genome Research* vol. 8 1998, 175-185.

Fang, Xiaohong et al., "Designing a Novel Molecular Beacon for Surface-Immobilized DNA Hybridization Studies", *Journal of the American Chemical Society* vol. 121, No. 12 Mar. 31, 1999, 2921-2922.

Fleischmann, Robert D. et al., "Whole-genome random sequencing and assembly of *Haemophilus influenzae* Rd", *Science* vol. 269, No. 5223 Jul. 28, 1995, 496-498; 507-512.

Forster, T., "Modern Quantum Chemistry", *Istanbul Lectures* Part III, Academic Press 1965, 93-137.

Fu, Dong-Jing et al., "Sequencing double-stranded DNA by strand displacement", *Nucleic Acids Research* vol. 25, No. 3 Feb. 1997, 677-679.

Furey, W S. et al., "Use of Fluorescence Resonance Energy Transfer to Investigate the Conformation of DNA Substrates Bound to the Klenow Fragment", *Biochemistry* vol. 37, No. 9 1998, 2979-2990.

Gao, Xiaolian, "Probing structural factors stabilizing antisense oligonucleotide duplexes: NMR studies of a DNA.cntdot.DNA duplex containing a formacetal linkage", *Biochemisry* vol. 31, No. 27 Jul. 1992, 6228-6236.

Gao, Xiaolian, "Structural correlations of backbone modifications in antisense oligonucleotide duplexes.", *Nucleosides, Nucleotides & Nucleic Acids* vol. 16, No. 7 Jul. 1997, 1599-1608.

Garcia, Anna M. et al., "Determination of ion permeability by fluorescence quenching", *Methods in Enzymology* vol. 207, No. 33 1992, 501-510.

Goodwin, Peter M. et al., "Application of Single Molecule Detection to Dna Sequencing", *Nucleosides, Nucleotides & Nucleic Acids* vol. 16, No. 5&6 May 1997, 543-550.

Guatelli, John C. et al., "Isothermal, In Vitro Amplification of Nucleic Acids by a Multienzyme Reaction Modeled After Retroviral Replication", *Proceedings of the National Academy of Sciences (PNAS)* vol. 87 Mar. 1990, 1874-1878.

Gupta, K. C. et al., "A general method for the synthesis of 3'-sulfhydryl and phosphate group containing oligonucleotides", *Nucleic Acids Research* vol. 19, No. 11 Jun. 11, 1991, 3019-3025.

Hardin, Susan H. et al., "Octamer-primed cycle sequencing: design of an optimized primer library.", *Genome Research* vol. 6, No. 6 Jun. 1996, 545-550.

Harding, John D., "Single-molecule detection as an approach to rapid DNA sequencing", *Trends in Biotechnology* vol. 10 1992, 55-57.

Holland, Pamela M. et al., "Detection of Specific Polymerase Chain Reaction Product by Utilizing the 5'->3' Exonuclease Activity of *Thermus aquaticus* DNA Polymerase", *Proceedings of the National Academy of Sciences (PNAS)* vol. 88, National Academy of Sciences of the USA Aug. 1991, 7276-7280.

Huber, Hans E. et al., "*Escherichia coli* Thioredoxin Stabilizes Complexes of Bacteriophage T7 DNA Polymerase and Primed Templates", *The Journal of Biological Chemistry* vol. 262, No. 33 Nov. 25, 1987, 16224-16232.

Hultman, Thomas et al., "Direct solid phase sequencing of genomic and plasmid DNA using magnetic beads as solid support", *Nucleic Acids Research* vol. 17 Jul. 11, 1989, 4937-4946.

Hunkapiller, T et al., "Large-scale and automated DNA sequence determination", *Science* vol. 254, No. 5028 Oct. 4, 1991, 59-67.

Jett, James H. et al., "High-Speed DNA Sequencing: An Approach Based Upon Fluorescence Detection of Single Molecules", *Journal of Biomolecular Structure and Dynamics* vol. 7 1989, 301-308.

Johnson, J. C. et al., "An Enzymic Method for Determination of Inorganic Pyrophosphate and Its Use as an Assay for RNA Polymerase", *Analytical Biochemistry* vol. 26, No. 1 1968, 137-145.

Jones, Douglas H. et al., "An Iterative and Regenerative Method for DNA Sequencing", *Biotechniques* vol. 22, No. 5 May 1997, 938-946.

Jones, Leslie B. et al., "Octamer Sequencing Technology : Optimization Using Fluorescent Chemistry", *ABRF News* vol. 9, No. 2 Jun. 1988, 6-10.

Jones, Leslie B. et al., "Octamer-Primed Cycle Sequencing Using Dye-Terminator Chemistry", *Nucleic Acids Research* vol. 26 1998, 2824-2826.

Ju, Jingyue et al., "Fluorescence Energy Transfer Dye-Labeled Primers for DNA Sequencing and Analysis", *Proceedings of the National Academy of Sciences (PNAS)* vol. 92: National Academy of Sciences of the USA May 1995, 4347-4351.

Kawata, Yoshimasa et al., "Feasibility of molecular-resolution fluorescence near-field microscopy using multi-photon absorption and field enhancement near a sharp tip", *Journal of Applied Physics* vol. 85, No. 3 1999, 1294-1301.

Keller, Ra et al., "Single-molecule fluorescence analysis in solution", *Applied Spectroscopy* vol. 50, No. 7 Jul. 1996, 12A-32A.

Kelman, Zvi et al., "Processivity of DNA polymerases: two mechanisms, one goal", *Structure* vol. 6, No. 2 Jan. 15, 1998, 121-125.

Kieleczawa, Jan, "DNA sequencing by primer walking with strings of contiguous hexamers", *Science* vol. 258, No. 5089 Dec. 11, 1992, 1787-1791.

Kim, Baek et al., "New Human Immunodeficiency Virus Type 1 Reverse Transcriptase (HIV-1 RT) Mutants with Increased Fidelity of DNA Synthesis", *Journal of Biological Chemistry* vol. 274, No. 39 Sep. 24, 1999, 27666-27673.

Kinjo, Masataka et al., "Ultrasensitive hybridization analysis using fluorescence correlation spectroscopy", *Nucleic Acids Research* vol. 23, No. 10 May 25, 1995, 1795-1799.

Koster, Hubert et al., "A strategy for rapid and efficient DNA sequencing by mass spectrometry", *Nature Biotechnology* vol. 14 Sep. 1, 1996, 1123-1128.

Kotler, Lev E. et al., "DNA sequencing: modular primers assembled from a library of hexamers or pentamers", *Proceedings of the National Academy of Sciences (PNAS)* vol. 90, No. 9 May 1, 1993, 4241-4245.

Kristensen, T et al., "Rapid and Simple Preparation of Plasmids Suitable for Dideoxy DNA Sequencing and Other Purposes", *DNA sequence : the journal of DNA sequencing and mapping* vol. 1, No. 4 1991, 227-232.

Kunkel, Thomas A., "DNA replication fidelity", *Journal of Biological Chemistry* vol. 267, No. 26 Sep. 15, 1992, 18251-18254.

Lebel, Denis et al., "Characterization and purification of a calcium-sensitive ATP diphosphohydrolase from pig pancreas", *Journal of Biological Chemistry* vol. 255, No. 3 Feb. 10, 1980, 1227-1233.

Lee, L G. et al., "New energy transfer dyes for DNA sequencing", *Nucleic Acids Research* vol. 25, No. 14 Jul. 1997, 2816-2822.

Lewis, Frederick D. et al., "Bispyrenyl Excimer Fluorescence: A Sensitive Oligonucleotide Probe", *J Am Chem Soc* vol. 119 1997, 5451-5452.

Lewis, Deborah A. et al., "Uniquely Altered DNA Replication Fidelity Conferred by an Amino Acid Change in the Nucleotide Binding Pocket of Human Immunodeficiency virus Type I Reverse Transcriptase", *The Journal of Biological Chemistry* vol. 274, American society for Biochemistry and Molecular Biology Nov. 12, 1999, 32924-32930.

Li, Ying et al., "Crystal structures of open and closed forms of binary and ternary complexes of the large fragment of *Thermus aquaticus* DNA polymerase I: structural basis for nucleotide incorporation", *European Molecular Biology Organization* vol. 17, No. 24 1998, 7514-7525.

Li, Ying et al., "Crystal structures of the Klenow fragment of *Thermus aquaticus* DNA polymerase I complexed with deoxyribonucleoside triphosphates", *Protein Science* vol. 7, No. 5 May 1998, 1116-1123.

Lichtarge, Olivier, "An Evolutionary Trace Method Defines Binding Surfaces Common to Protein Families", *Journal of Molecular Biology* vol. 257, No. 2 Mar. 29, 1996, 342-358.

Lundberg, Kelly S. et al., "High-fidelity amplifications using a thermostabile DNA. polymerase isolated from *Pyrococcus furiosus*", *Gene* vol. 108, Elsevier Science B.V. 1991, 1-6.

Mackerell, A D. et al., "All-Atom Empirical Potential for Molecular Modeling and Dynamics Studies of Proteins", *Journal of Physical Chemistry* vol. 102, No. 18 Apr. 30, 1998, 3586-3616.

Maxam, Allan M. et al., "A New Method for Sequencing DNA", *Proceedings of the National Academy of Sciences (PNAS)* vol. 74, The National Academy of Sciences of the USA Feb. 1977, 560-564.

Mei, Gangwu, "Octamer-primed sequencing technology: development of primer identification software", *Nucleic Acids Research* vol. 28, No. 7 Apr. 2000, i-ix.

Molecular Simulations, Inc, "Quanta and InsightII", www.msi.com www.msi.com 2000.

Morris, Garrett M. et al., "Automated docking using a Lamarckian genetic algorithm and an empirical binding free energy function", *Journal of Computational Chemistry* vol. 19, No. 14 Nov. 15, 1998, 1639-1662.

Narasimhan, Krishna et al., "ρ-Benzoquinone activation of metal oxide electrodes for attachment of enzymes", *Enzyme and Microbial Technology* vol. 7, No. 6 Jun. 1985, 283-286.

Nelson, Paul S. et al., "Bifunctional oligonucleotide probes synthesized using a novel CPG support are able to detect single base pair mutations", *Nucleic Acids Research* vol. 17 Sep. 25, 1989, 7187-7193.

Nickerson, Deborah A. et al., "PolyPhred: automating the detection and genotyping of single nucleotide substitutions using fluorescence-based resequencing", *Nucleic Acids Research* vol. 25, No. 14 Jul. 1997, 2745-2751.

Nie, Shuming et al., "Probing individual molecules with confocal fluorescence microscopy", *Science* vol. 266 Nov. 11, 1994, 1018-1021.

Nie, Shuming, "Real-Time Detection of Single Molecules in Solution by Confocal Fluorescence Microscopy", *Analytical Chemistry* vol. 67, No. 17 Sep. 1, 1995, 2849-2857.

Novotny, Lukas et al., "Theory of Nanometric Optical Tweezers", *Physical Review Letters* vol. 79, No. 4 1997, 645-648.

Nyren, Pal, "Enzymatic Method for Continuous Monitoring of DNA Polymerase Activity", *Analytical Biochemistry* vol. 167, No. 2 1987, 235-238.

Orrit, M et al., "Single molecule fluorescence: from excitation spectra to time correlation", *Journal of Luminescence* vol. 60-61 1994, 991-996.

Orrit, M et al., "Single pentacene molecules detected by fluorescence excitation in a ρ-terphenyl crystal", *Physical Review Letters* vol. 65, No. 21 Nov. 19, 1990, 2716-2719.

Osheroff, Wendy P. et al., "The Fidelity of DNA Polymerase during Distributive and Processive DNA Synthesis", *Journal of Biological Chemistry* vol. 274, No. 6 Feb. 5, 1990, 3642-3650.

Paris, Pamela L. et al., "Probing DNA Sequences in Solution With a Monomer-Excimer Fluorescence Color Change", *Nucleic Acids Research* vol. 26, No. 16: Oxford University Press 1998, 3789-3793.

Raja, Mugasimangalam C. et al., "DNA sequencing using differential extension with nucleotide subsets", *Nucleic Acids Research* vol. 25, No. 4 Feb. 1997, 800-805.

Reeve, Michael A. et al., "A novel thermostabile polymerase for DNA sequencing", *Nature* vol. 376, Nature Publishing Group Aug. 31, 1995, 796-797.

Rice, Jeffrey S. et al., "Conformation of formacetal and 3'-thioformacetal nucleotide linkers and the stability of their antisense RNA-DNA hybrid duplexes", *Biochemistry* vol. 36, No. 2 Jan. 14, 1997, 399-411.

Ronaghi, Mostafa et al., "DNA Sequencing: A Sequencing Method Based on Real-Time Pyrophosphate", *Science* vol. 281, No. 5375 Jul. 17, 1998, 363-365.

Ronaghi, Mostafa et al., "Real-Time DNA Sequencing Using Detection of Pyrophosphate Release", *Analytical Biochemistry* vol. 242, No. 1 Nov. 1, 1996, 84-89.

Rosenblum, B B. et al., "New dye-labeled terminators for improved DNA sequencing patterns", *Nucleic Acids Research* vol. 25, No. 22 Nov. 1997, 4500-4504.

Sanchez, Erik J. et al., "Near-Field Fluorescence Microscopy Based on Two-Photon Excitation with Metal Tips", *Physical Review Letters* vol. 82, No. 20 May 17, 1999, 4014-4017.

Sanger, F et al., "DNA sequencing with chain-terminating inhibitors", *Proceedings of the National Academy of Sciences (PNAS)* vol. 74, No. 12 Dec. 15, 1977, 5463-5467.

Sauer, M et al., "Detection and identification of single dye labeled mononucleotide molecules released from an optical fiber in a microcapillary: First steps towards a new single molecule DNA sequencing technique", *Physical Chemistry Chemical Physics* vol. 1, No. 10 1999, 2471-2477.

Schlageck, Joseph G. et al., "Spectroscopic techniques for study of phosphodiester bond formation by *Escherichia coli* RNA polymerase", *Journal of Biological Chemistry* vol. 254, No. 23 Dec. 10, 1979, 12074-12077.

Schmidt, TH. et al., "Imaging of single molecule diffusion", *Proceedings of the National Academy of Sciences (PNAS)* vol. 93, No. 7 Apr. 2, 1996, 2926-2929.

Schwille, Petra et al., "Dual-color fluorescence cross-correlation spectroscopy for multicomponent diffusional analysis in solution.", *Biophysical Journal* vol. 72, No. 4 Apr. 1997, 1878-1886.

Siemieniak, David R. et al., "A library of 3342 useful nonamer primers for genome sequencing", *Gene* vol. 96, No. 1 1990, 121-124.

Smith, Lloyd M. et al., "Fluorescence detection in automated DNA sequence analysis", *Nature* vol. 321 Jun. 12, 1986, 674-679.

Soares, T A. et al., "Docking of 4-oxalocrotonate tautomerase substrates: Implications for the catalytic mechanism", *Biopolymers* vol. 50, No. 3 Sep. 1999, 319-328.

Sproat, Brian S. et al., "The synthesis of protected 5'-mercapto-2',5'-dideoxyribonucleoside-3'-0-phosphorainidites; uses of 5'-mercapto-oligodeoxyribonucleotides", *Nucleic Acids Research* vol. 15, No. 12 Jun. 25, 1987, 4837-4849.

Studier, F W., "A strategy for high-volume sequencing of cosmid DNAs: random and directed priming with a library of oligonucleotides", *Proceedings of the National Academy of Sciences (PNAS)* vol. 86, No. 18 Sep. 1989, 6917-6921.

Syvanen, Ann-Christine et al., "A primer-guided nucleotide incorporation assay in the genotyping of apolipoprotein E", *Genomics* vol. 8, No. 4 Dec. 1990, 684-692.

Tabor, Stanley et al., "A Single Residue in DNA Polymerases of the *Escherichia coli* DNA Polymerase I Family is Critical for Distinguishing Between Deoxy- and Dideoxyribonucleotides", *Proceedings of the National Academy of Sciences (PNAS)* vol. 92(14) Jul. 1995, 6339-6343.

Tabor, Stanley et al., "DNA Sequence Analysis with a Modified Bacteriophage T7 DNA Polymerase", *Journal of Biological Chemistry* vol. 265, No. 14 May 15, 1990, 8322-8328.

Tabor, Stanley et al., "*Escherichia coli* Thioredoxin Confers Processivity on the DNA Polymerase Activity of the Gene 5 Protein of Bacteriophage T7", *The Journal of Biological Chemistry* vol. 262, No. 33 Nov. 25, 1987, 16212-16223.

Tokunaga, Makio et al., "Single Molecule Imaging of Fluorophores and Enzymatic Reactions Achieved by Objective-Type Total Internal Reflection Fluorescence Microscopy", *Biochemical and Biophysical Research Communications* vol. 235, No. 1 Jun. 9, 1997, 47-53.

Tong, Glenn et al., "Oligonucleotide-Polyamide Hybrid Molecules Containing Multiple Pyrene Residues Exhibit Significant Excimer Fluorescence", *Journal of the American Chemical Society* vol. 117, No. 49 Dec. 1995, 12151-12158.

Tyagi, Sanjay et al., "Molecular Beacons : Probes that fluoresce upon Hybridization", *Nature Biotechnology* vol. 14, No. 3 Mar. 1996, 303-308.

Tyagi, Sanjay et al., "Multicolor molecular beacons for allele discrimination", *Nature Biotechnology* vol. 16, No. 1, Nature Publishing Group Jan. 1998, 49-53.

Tyagi, Sanjay C. et al., "Synthesis and characterization of fluorescent dinucleotide substrate for the DNA-dependent RNA polymerase from *Escherichia coli*", *Journal of Biological Chemistry* vol. 262, No. 22 Aug. 5, 1987, 10684-10688.

Velculescu, Victor E. et al., "Serial Analysis of Gene Expression", *Science* vol. 270, No. 5235 Oct. 20, 1995, 484-487.

Voss, H. et al., "Automated Cycle Sequencing with Taquenase: Protocols for Internal Labeling, Dye Primer and Doublex Simultaneous Sequencing", *BioTechniques* vol. 23, No. 2 Aug. 1997, 312-318.

Wainberg, Mark A. et al., "Enhanced Fidelity of 3TC-Selected Mutant HIV-1 Reverse Transcriptase", *Science* vol. 271 Mar. 1, 1996, 1282-1285.

Weiss, Shimon et al., "Flourescence Spectroscopy of Single Biomolecules", *Science* vol. 283, No. 5408 Mar. 12, 1999, 1676-1683.

Wong, Isaac et al., "An induced-fit kinetic mechanism for DNA replication fidelity: direct measurement by single-turn-over kinetics", *Biochemistry* vol. 30, No. 2 Jan. 1991, 526-537.

Wu, Felicia Y. et al., "Synthesis and properties of adenosine-5'-triphosphoro-γ-1-(5-sulfonic acid)naphthyl ethylamidate: A fluorescent nucleotide substrate for DNA-dependent RNA polymerase from *Escherichia coli*", *Archives of Biochemistry and Biophysics* vol. 246, No. 2 May 1, 1986, 564-571.

Xu, Xiao-Hong N. et al., "Long-Range Electrostatic Trapping of Single-Protein Molecules at a Liquid-Solid Interface", *Science* vol. 11, No. 5383 Sep. 1998, 1650-1653.

Yamana, Kazushige, "Synthesis of oligonucleotide derivatives containing pyrene labeled glycerol linkers: Enhhanced excimer fluorescence on binding to a complementary DNA sequence", *Tetrahedron Letters* vol. 38, No. 34 Aug. 25, 1997, 6051-6054.

Yang, Xueyong et al., "NMR Structure of an Antisense DNA•RNA Hybrid Duplex Containing a 3'-CH2N(CH3)-O-5' or an MMI Backbone Linker", *Biochemistry* vol. 38, No. 39 Sep. 28, 1999, 12586-12596.

Yanlong, et al., "Design, Synthesis, and Spectroscopic Properties of Peptide: Bridged Fluorescence Energy-Transfer Cassettes", *Bioconjugate Chem.* vol. 10 1999, 241-245.

Yarbrough, Lynwood R., "Synthesis and Properties of a New Fluorescent Analog of ATP: Adenosine-5'-Triphosphoro-γ-1-(5-SUlfonic Acid) Napthylamidate", *Biochemical and Biophysical Research Communications* vol. 81, No. 1 Mar. 15, 1978, 35-41.

Yarbrough, L R. et al., "Synthesis and properties of fluorescent nucleotide substrates for DNA-dependent RNA polymerases", *Journal of Biological Chemistry* vol. 254, No. 23 Dec. 10, 1979, 12069-12073.

Zuckermann, Ronald et al., "Efficient Methods for Attachment of Thiol Specific Probes to the 3'-ends of Synthetic Oligodeoxyribonucleotides", *Nucleic Acids Research* vol. 15, No. 13 Jul. 10, 1987, 5305-5321.

Anal Biochem 1990 Dec; 191 (2):396-400. Engelke DR., et. al. Purification of Thermus DNA polymerase expressed in *Escherichia coli*.

Anal Chem 1990 Sep 1;62(17):1786-1791. Mathies RA, et.al. Optimization of high-sensitivity fluorescence detection.

Anal Chem 1999 Jul 15;71(14):2850-2857. Sauer M, et. al. Interaction of chemically modified antisense oligonucleotides with sense DNA: a label-free interaction study with reflectometric interference spectroscopy.

Brandis, Dye structure affects Taq DNA polymerase terminator selectivity, 1999, Nucleic Acids Research, vol. 27. No. 8, pp. 1912-1918.

Cytometry 1999 Jul 1;36(3): 163-168. Dapprich J Single-molecule DNA digestion by lambda-exonuclease.

EurBiophys J 28(6):457-467. Blachut-Okrasinska E., et.al. Poisson-Boltzmann model studies of molecular electrostatic properties of the cAMP dependent protein Kinase. 1999 (Abstract Only).

Gardner et al., "Acyclic and dideoxy terminator preferences denote divergent sugar recognition by archeon and Taq DNA polymerases", 2002, Nucleic Acids Research, vol. 30, No. 2, pp. 605-613.

Hepatology 1998 Jun;27(6):1670-1677. Allen Mi, et.al. Identification and characterization of mutations in hepatitis B virus resistant to lamivudine. Lamivudine Clinical Investigation Group.

Hereditas 1998; 129(2):161-167. Allen M, et.al. High resolution genetic typing of the class II HLA-DRB 1 locus using group-specific amplification and SSO-hybridisation in microplates.

Hum Mut 1996; 7 (2):89-99. Zhuang J, et al. Direct sequencing of PCR products derived from cDNAS for the pro alpha I and pro alpha 2 chains of type I procollagen s a screening method to detect mutations in patients with osteogenesis imperfecta.

J Biol Chem 1998 Sep 4; 273(36): 23558-23566. Li, Xy et. al. Stimulation of open complex formation by nicks and apurinic sites suggests a role for nucleation of DNA melting in *Escherichia coli* promoter function.

J Mol Biol 1994 May 6:238(3):415-436. Antosiewicz J., et. al. Prediction of Ph-dependent properties of proteins.

Mem Inst Oswaldo Cruz 1992;87:235-239. Davis, WC. et.al, a rapid, reliable method of evaluating growth and viabilit of intraerythrocytic protozoan hemoparasites using fluorescence flow cytometry.

Nat Biotechnol 1999 Aug; 17(8):822-823. Murphy JC, et.al. Purification of plasmid DNA using selective precipitation by compaction agents.

Nature 1989 Nov 16:342(6247):224-225. Sambrook J, et. al. Protein structure. Chaperones, paperones.

Nucleic Acids Res 1999 Aug 1;27(15):3057-3063. Mitsis PG, et.al. Characterization of the interaction of lambda exonuclease with the ends of DNA.

Proc Natl Acad Sci USA 1989 Jun;86(11):4087-4091. Peck K, et.al. Single-molecule fluorescence detection: autocorrelation criterion and experimental realization with phycoeytherin.

Voet et al. Biochemistry, 1990, John Wiley & Sons, First Edition, pp. 329-352.

Wisniewski et al., "Mutations in the Primer Grip Region of HIV Reverse Transcriptase Can Increase Replication Fidelity", The Journal of Biological Chemistry, vol. 274, No. 40, pp. 28175-28184.

* cited by examiner

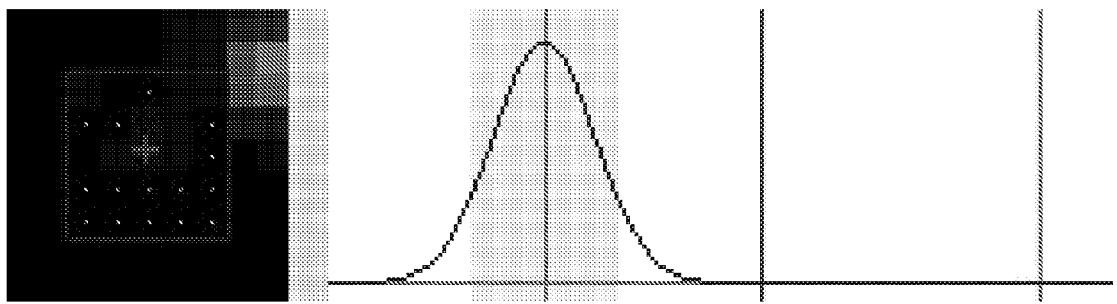
FIG. 4
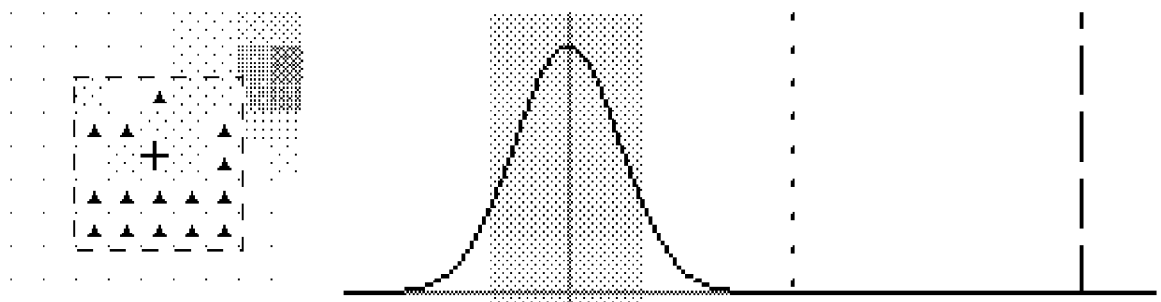
FIG. 4'
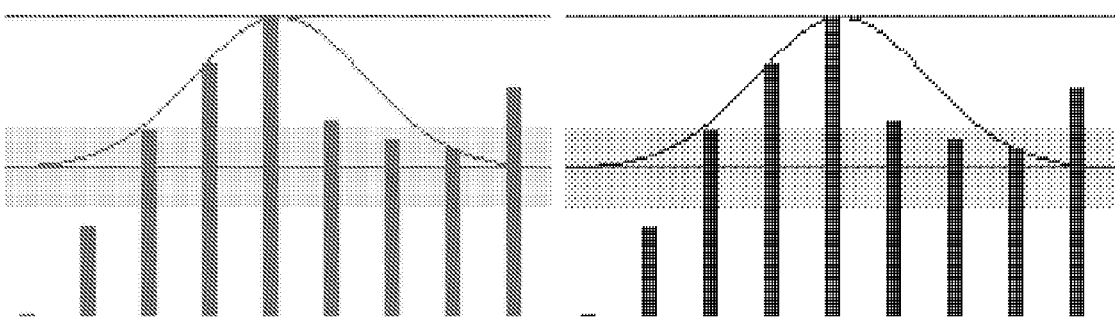
FIG. 5       FIG. 5'

METHOD FOR ANALYZING DYNAMIC DETECTABLE EVENTS AT THE SINGLE MOLECULE LEVEL

RELATED APPLICATIONS

This application claims priority to U.S. Provisional Patent Application Ser. No. 60/765,693 filed 6 Feb. 2006, now expired, is a continuation-in-part of U.S. patent application Ser. No. 09/901,782, filed 3 Jul. 2001, and is a continuation-in-part of U.S. patent application Ser. No. 10/007,621, filed 3 Dec. 2001, now U.S. Pat. No. 7,211,414, issued 1 May 2007.

GOVERNMENTAL INTEREST

Some of the subject matter disclosed in this application was funded to some degree by funds supplied by the United States Government under NIH grant no. 5 R01 HG003580

BACKGROUND OF THE INVENTION

1. Field of the Invention

The present invention relates to a method for characterizing signals generated from molecular events at the single molecule level, such as donor-acceptor fluorescent resonance energy transfer events, of dynamic systems or static systems over a period of time, where the event data can be collected continuously, periodically, or intermittently and analyzed continuously, periodically or intermittently. The data collection and analysis, thus, can be in real time or near real time, while analysis can be any time post collection. A dynamic system means that the data is collected on the system in real time over the period of time as the system undergoes detectable changes in one or more detectable properties, while a static system means that the data is collected for a given period of time and the system is unchanging during that period of time.

More particularly, the present invention relates to a method for characterizing signals generated from detectable molecular events at single molecule level, where the method includes the steps of collecting and storing data from a viewing field associated with a detector, where the viewing field includes a plurality of molecules or molecular assemblies capable of being detected directly and undergoing a detectable event or a plurality of detectable events, where direct detection involves monitoring at least one detectable property associated with the molecule or molecular assembly and where the detectable events involve interactions associated with or occurring at the molecule or molecular assembly. Data associated with the viewing field is collected into one data channel or a plurality of data channels, where each data channel corresponds to an attribute of the detected events, such as intensity, frequency or wavelength, duration, phase, attenuation, etc. The method also includes the step of reading the stored data and spatially registering or calibrating the data channels so that a given location within the viewing field in one channel corresponds to the same location in the other channels—the data is registered relative to the viewing field. After registering, candidate molecules or molecular assemblies are identified. The candidate identification is generally designed to minimize locations within the viewing field that include more than a single directly detected molecule or molecular assembly to simplify data analysis. Next, an n×m array of data elements such as pixels is selected for each candidate so that the array includes all data elements having a detection value above a definable threshold originating from or associated with each candidate such as a definable intensity threshold value. Then, a plurality of "dark" data elements or pixels in an immediate neighborhood of the array associated with each candidate are selected to improve background removal. Once the array and background elements have been selected, a hybrid dataset for each candidate is constructed derived from data from two or more data channels. The hybrid dataset is then smoothed and differentiated. After smoothing and differentiating, non-productive events are separated from productive events based on a set of criteria, where the criteria are dependent on the detectable property and events being detected. The productive events are then placed in time sequence. For donor-acceptor systems, the method includes determining anti-correlated donor and acceptor fluorescent signals. For monomer sequencing (nucleotide, amino acid, saccharide, etc.), the criteria are designed to separate binding and mis-incorporation events from true incorporation events, and when placed in time order, evidence a sequence of monomers in a target sequence of monomers.

2. Description of the Related Art

With the increase in single molecular analytical techniques, there have been developed many software routines for analyzing the resulting data. However, each single molecule analytic technique gives rise to many unique problems and normal analytical software is ill suited to analyze data from very specific single molecule data detection systems.

Thus, there is a need in the art for data processing processes that can help researchers understand and characterize data corresponding to detectable events arising at the single molecule level especially in the area of single molecule fluorescence detection such as fluorescent resonance energy transfer signals originating from interactions between a donor or plurality of donors and an acceptor or a plurality of acceptors.

DEFINITIONS USED IN THE INVENTION

The term "single molecule level" means any individual system capable of undergoing detectable chemical or physical events that can be detected and analyzed independently. For example, systems of isolated atoms, molecules, ions, or assemblages of atoms, molecules and/or ions that have a detectable property that changes during a chemical or physical event capable of individual detection and analysis satisfy the definition. Such systems include, without limitation, any isolated reactive system having a detectable property that undergoes as change before, during or after a chemical and/or physical event or reaction. Exemplary examples of such systems including, again without limitation, DNA replication complexes, protein translation complexes, transcription complexes, any other isolated or isolatable biological system, quantum dots, catalysts, cellular sites, tissue sites, domains on chips (groove, lines, channels, pads, etc.), or any other system having a detectable property that undergoes a change before, during and/or after a chemical and/or physical event. Although the isolated single reactive systems simplify analysis, images including overlapping or multiply occupied sites can be analyzed as well, but with greater difficulty.

The term "detection at the single molecule level" means that chemical events are being detected at the single molecule level.

The term "anti-correlated" means that changes in a value of a first detected response are opposite to changes in a value of a second detected response.

The term "correlated" means that changes in a value of a first detected response are coincide (same direction) to changes in a value of a second detected response.

The term "data channel or data quadrant" means data that has a particular attribute such as data within a given frequency range of light derived from a given detector or imagining system. A quadrant more specifically is terminology relating to a data channel of a particular type of imaging apparatus such as a charge coupled device (CCD) imaging apparatus.

The term "slide" means an actual sample, which is often disposed on the surface of a treated or untreated surface such as the surface of a cover slip.

The term "viewing field" or "viewing volume" means the actual portion of the sample that is being observed by the imagining or detecting system. Often this volume is considerably smaller than the actual sample and is dependent on the exact nature of the imagining or detection system being used.

The term "frame" means an image of the viewing field taken over a short period of time within the imagining or detecting system prior to being outputted to the processing system. The size and time span of the frame depends on the memory, buffering, outputting speed and receiving speed of the imagining system and of the processing system.

The term "stack" or "stream" means a set of frames. Thus, frames from a single slide are collected as a stack of frames or a stream of frames.

The term "trace" means data for a particular data element or pixel over all the frames in a stack or over a given number of frames in a stack.

The term "related data" means data from other data channels that are related to data from a selected data channel. The data can be spatially related, temporally related, network related, etc. or related through a combination of these relationship types.

The term "data calibration or registration" means transforming data in one data channel so all locations within that data channel are matched to corresponding locations in other data channels.

The term "assemblage" means a collection of atoms, molecules and/or ions to form an isolated or isolatable system. For example, a DNA replication complex is an assemblage and a ribosome translation complex is an assemblage. The collection can be of a single atomic or molecular type (atom clusters, molecular cluster, etc.) or a collection of mixtures of atoms, molecules, and/or ions. Assemblages can also be constructed of assemblages. The main criterion in the definition is that the assemblage be capable of being isolated or formed in an isolated manner so that detectable events occurring at each individual assemblage can be separately detected and analyzes.

The term "spot" means a location within a viewing field of an imaging apparatus that evidence fluorescent light from one or more atoms, molecules, ions or assemblages. Although the method have focused on fluorescent light, the method can be applied to any detectable property that corresponds to one or more atoms, molecules, ions or assemblages within a viewing field.

SUMMARY OF THE INVENTION

The present invention provides a method implemented on a computer for collecting data in real or near real time, at the single molecule level corresponding to detectable chemical and/or physical events and analyzing the collected data to identify the events and classify the events as to their intrinsic nature. The method can be used to collect and analyze data from monomer additions, polymerase extension reactions, protein biosynthesis at ribosomal machinery, (translation reactions), saccharide polymerization reactions, kinase phosphorylation reactions, or any other reaction that involves interactions between atoms, ions, molecules or assemblages having at least one detectable that undergoes a change before, during or after the reaction being monitored.

The present invention also provides a method implemented on a computer including the step of collecting data representing values of an attribute or attributes of a detectable property or detectable properties of an atom, an ion, a molecule or an assemblage of atoms, ions and/or molecules or a plurality of atoms, ions, molecules or assemblages of atoms, ions and/or molecules within a viewing volume or field over a period of time. The collected data includes data derived directly from the atom(s), molecule(s) and/or assemblage(s) and data derived from events evidencing interactions between the atom(s), ion(s), molecule(s) or assemblage(s) and other atomic, ionic, molecular, and/or assemblage species or between different parts of the ion(s), molecule(s) or assemblage(s). If the data is collected simultaneously in a plurality of data channels, then after data collection, the data in the data channels are calibrated or registered to align the data within the channels spatially and temporally. After data registration, data in one data channel, often times a primary data channel corresponding to the directly detected data, are scanned and an atom, ion, molecule or assemblage candidate or atom, ion, molecule, or assemblage candidates within the viewing volume or field that meet a set of detection criteria are selected. After candidate selection, the candidate data is smoothed, hybridized and differentiated. After or simultaneously, data from other data channels are scanned and related data are selected from these other channels, where the related data is data that evidences changes in a detectable property or an attribute or attributes thereof spatially, temporally, or otherwise related to the candidate data. Generally, the related data is data that evidences changes in a detectable property or an attribute or attributes thereof occurring within a neighborhood of each candidate. This related data is then analyzed, smoothed, hybridized and differentiated. The candidate data and their related data are then analyzed together to produce events. If the interactions are anti-correlated, then the candidate data and their related data are analyzed for anti-correlated events. Anti-correlation means that changes in the detectable property(ies) of the atom(s), ion(s), molecule(s) or assemblage(s) and opposite changes in the detectable property(ies) of the other atomic, ionic, molecular or assemblage species, such as a reduction in a donor intensity and a corresponding increase in acceptor intensity. After anti-correlation analysis, the anti-correlated events are classified as relating to one of a set of event types, such as a productive event type, a non-productive event type, a binding event type, a pre-binding event type, a group release event type, a mis-incorporation event type, a complexing event, a transition event, etc. For example, if the method is directed toward nucleic acid sequencing, the classification scheme includes a correct base incorporation event type, a mis-match or incorrect base incorporation event type, a binding event type, a pre-base incorporation event type, a proximity event type, a pyrophosphate release event, etc.

The present invention also provides a method implemented on a computer including the step of collecting data including a plurality of data channels representing fluorescent data from a plurality of fluorophores within a viewing volume or field. After data collection, the data within the data channels are calibrated or registered to align the data spatially and temporally, i.e., locations within the viewing field are matched between the channels. After data alignment, the data in a primary channel is scanned for the candidate fluorophores within the viewing volume that meet a set of candidate criteria. For example, if the system is a donor-acceptor system, then the primary channel is the donor channel. After candidate selection, the data associated with each candidate is smoothed, hybridized and differentiated. After or simultaneously, related data from the other channels are selected, where the related data is data within a neighborhood of each donor candidate that undergoes a change over time. After selection of the related data, the related data is smoothed, hybridized and differentiated. The candidate and related data are then analyzed together to identify events. The events are then classified. If the system is a donor-acceptor system, the related data is acceptor data and the donor data and the acceptor data are analyzed for anti-correlated events evidence by anti-correlated intensity shifts. After identification of anti-correlated intensity events, the identified anti-correlated events are classified as relating to one of a set of event types, such as a productive binding event, a pre-binding event, a non-productive binding event, etc. For example, if the method is directed toward determining base incorporation events, the classification scheme includes a correct base incorporation event, a mis-match or incorrect base incorporation event, a non-productive base binding event, a pre-base incorporation event, a proximity event, etc.

The present invention provides a system for characterizing events at the single molecule level, including a sample subsystem and optionally an irradiating subsystem for irradiating a sample in the sample subsystem. The system also include a detector subsystem for detecting and collecting data evidencing changes in a detectable property associated with an atom, ion, molecule or assemblage within the sample subsystem or within a region of the sample subsystem. The system also includes a processing subsystem that stores and processes the data collected by the detector. The processing subsystems uses methods of this invention to identify event and to classify the identified events. The classification is then related to aspects of the dynamic system being detected. For DNA, RNA or DNA/RNA hybrid sequencing, the classification permits identification of the base sequence of an unknown nucleic acid molecule. Although the system collects data in real time, the data processing can occur in real time, near real time or it can be processed later or both.

The present invention also provides a system for characterizing donor-accept fluorescent resonance energy transfer events at the single molecule level, including a TIRF or similar sample assembly, a detector system for irradiating the sample assembly with an incident light having a wavelength range designed to excite the donor fluorophores within a sample viewing volume and detecting fluorescent light emitted by emitters within the volume, where the emitters are the donors, acceptors activated by a donor via fluorescent resonance energy transfer (FRET), and background or nor donor/acceptor emitters. The system also includes a processing subsystem that stores and processes the data collected from the detector. The processing subsystems uses methods of this invention to produce a classification of detected fluorescent events. The classification is then related to aspects of the dynamic system being detected. For DNA, RNA or DNA/RNA hybrid sequencing, the classification permits identification of the base sequence of an unknown nucleic acid molecule. Although the system collects data in real time, the data processing can occur in real time or it can be processed later or both.

The present invention also provides a method for characterizing signals generated from molecular events at the single molecule level, dNTP or nucleotide incorporation fluorescent resonance energy transfer (dNTPFRET) events at the single molecule level, where the method includes the steps of collecting and storing pixelated data in a plurality of data fluorescent channels of a plurality of dNTPFRET events, reading the stored data, spatially registering or calibrating the data channels, identifying candidate single polymerase/primer/template complexes, selecting an n×n array of pixels including each identified candidate, selecting a plurality of "dark" pixels in the immediate neighborhood of the pixel array associated with each identified candidate for background removal, constructing a hybrid dataset for each candidate, smoothing the hybrid dataset, differentiating the hybrid dataset, determining anti-correlated donor and acceptor fluorescent events, separating true incorporation event from mis-incorporation and non-productive binding events and identifying one or a plurality of incorporated dNTPs corresponding to sequencing information associated with an unknown nucleic acid sequence.

BRIEF DESCRIPTION OF THE DRAWINGS

The invention can be better understood with reference to the following detailed description together with the appended illustrative drawings in which like elements are numbered the same.

FIG. 2' is a black and white version of FIG. 2, where ⊕ represents accepted spots, ▲ represents spots rejected at stages 2 and 3 and + represents spots rejected at stage 1.

FIG. 3a' is a black and white version of FIG. 3a, where + represents the brightest pixel, ▲ represents background pixels selected for computing c and na, dashed square represent the 7×7 pixel area around the spot, dotted line represents the 3na cutoff level, dashed line represents the brightest pixel intensity.

FIG. 3b' is a black and white version of FIG. 3b, where + represents the brightest pixel, ▲ represents background pixels selected for computing c and na, dashed square represent the 7×7 pixel area around the spot, dotted line represents the 3na cutoff level, dashed line represents the brightest pixel intensity.

FIG. 4 depicts a "poor" spot candidate passed through stage 1 filter.

FIG. 4' is a black and white version of FIG. 4, where + represents the brightest pixel, ▲ represents background pixels selected for computing c and na, dashed square represent the 7×7 pixel area around the spot, dotted line represents the 3na cutoff level, dashed line represents the brightest pixel intensity.

FIG. 5 depicts stage 2 filter.

FIG. 5' is black and white version of FIG. 5, where the dotted line represents doubt*avgna value and the dashed dotted line represents the minc*avgna value.

FIG. 6a' is black and white version of FIG. 6a, where + represents the brightest pixel, ▲ represents background pixels selected for computing c and na, dashed square represent the 7×7 pixel area around the spot, dotted line represents the 3 na cutoff level, dashed line represents the brightest pixel intensity.

FIG. 6a' is black and white version of FIG. 6a, where+ represents the brightest pixel,▲ represents background pixels selected for computing c and na, dashed square represent the 7×7 pixel area around the spot, dotted line represents the 3 na cutoff level, dashed line represents the brightest pixel intensity.

FIG. 6b' is black and white version of FIG. 6b, where the dotted line represents doubt*avgna value and the dashed dotted line represents the minc*avgna value.

FIG. 6c' is black and white version of FIG. 6c, where the dashed dotted line represents minc2*avgna value.

FIG. 6c depicts graphically the spot candidate filtering process of the stage 3 filter.

FIG. 6c' is black and white version of FIG. 6c, where the dashed dotted line represents minc2*avgna value.

FIG. 7b depicts selection of single spots in an average donor image after voting.

FIG. 7c depicts snapshot of grouped spots after voting and selection of the donor pixel.

FIGS. 10a'-10d' are black and white version of FIGS. 10a-10d, where the left panel represents the donor data, the middle panel represents the acceptor 1 data, the right panel represents acceptor 2 data,▲ represent signal pixels,+ represents noise pixels, the solid square represents the 3×3 pixel area for donor signal pixels and the dashed square represents the 7×7 pixel area for donor noise pixels.

FIGS. 11a'-11d' are black and white version of FIGS. 11a-11d, where the top trace in each graph represents the original (non-background subtracted) signal and the bottom trace in each graph represent the signal after background subtraction– 11a' presents the donor noise signals, 11b' presents the donor signal, 11c' presents acceptor noise signals, and 11d' presents the acceptor signals.

FIG. 12' is black and white version of FIG. 12 showing donor pixel selection, where the top panel represents the hybrid trace, the bar right below represents the donor lifetime, the remaining 9 panels represent individual donor pixel traces, and the grayed ones represent pixels rejected by pixel selection process. In the overlayed image, the ⊕ symbol represents accepted pixels, the + symbol represents rejected pixels, and the ◇ symbol represent noise pixels.

FIGS. 13a'-13b' is black and white version of FIGS. 13a-13b showing acceptor pixel selection, where 13a' represents intensitybased selection and 13b' represents DAC-based selection. From top to bottom: Donor (with donor lifetime bar), Acceptor hybrid (with lifetime), 9 individual pixel traces, the grayed ones rejected by the selection process. In the overlayed image, the ⊕ symbols represent accepted pixels, the+ symbols represent rejected pixels and the ◇ symbols represent noise pixels.

FIG. 15' is black and white version of FIG. 15 showing donor model—initial stage selection, where the top panel represents donor, the darker curve is smoothed donor signal, the lighter represents original; grayed area represent donor noise level. In the middle panel, donor derivatives are shown, grayed area is its standard deviation. The bottom bar represents donor derivative "lifetime" used to set segment boundaries (vertical lines).

FIGS. 16a'-16c' is black and whiteversion of FIGS. 16a-16c showing the donor model Optimization.

FIG. 17' is black and white version of FIG. 17 showing the donor model final stage. The segmented curve represents suggested 'donor high' level, gray area around it represents 'noise level in donor high state'. Bottom represents donor lifetime computed based on the donor model.

FIG. 18' is black and white version of FIG. 18, where the dark circle represents the middle sample, the dark squares represents samples being used together with the middle one to compute the polynomial (curve), the light squares represent samples not in use, and ◇ represents the value of the polynomial at the middle data sample location (smoothed value).

FIG. 19' is black and white version of FIG. 19, where the top panel represent a simulated signal (numbers showing duration in data samples), middle panel represents the simulated signal with added Gaussian noise, and the bottom panel represents smoothed signal.

FIGS. 20a'-20c' are black and white version of FIGS. 20a-20c, where the top panel represents the donor signal, the middle panel represents the acceptor signal, and the bottom panel represents the DAC function–20a'-no noise, 20b'-low noise(high S/N), 20c'-high noise (low S/N).

DETAILED DESCRIPTION OF THE INVENTION

Figure 1:
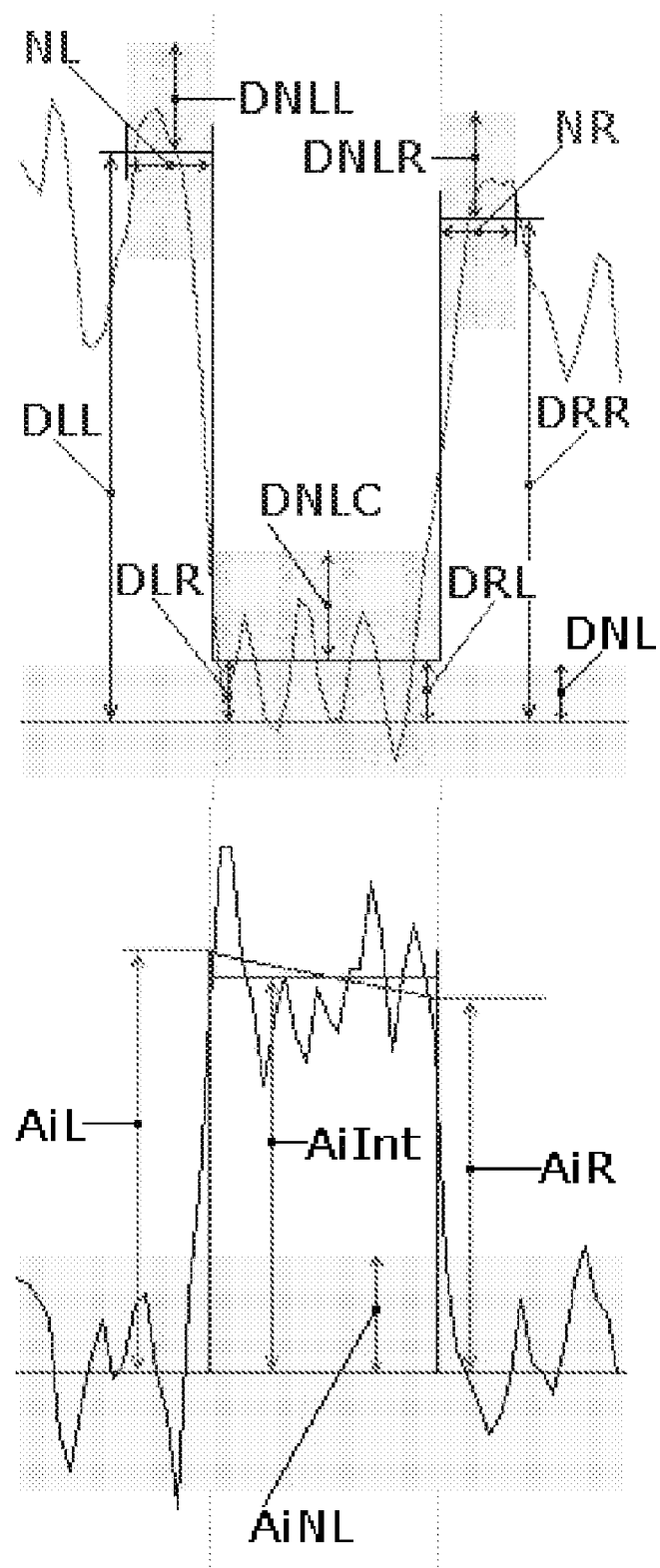
FIG. 1 depicts a graphical illustration of certain of the parameters that are used to define an event.

The inventors have found that a system including a method implemented on a computer can be constructed that is capable of collecting data corresponding to changes in a detectable property of one or more atoms, molecules, ions or assemblages within a viewing volume or field of an imaging apparatus such as a charge coupled device of a viewing volume or field. The method processes the single molecule level image data to identify and classify chemical events occurring at the atoms, molecules, ions or assemblages within a viewing volume. The inventors have found that the system and method are ideally well suited for collecting and analyzing DNA extension data derived from single molecule fluorescent events, especially single molecule fluorescent resonance energy transfer event between a donor associated with a replication complex and acceptors on incorporating nucleotides. Although the inventors have focused primarily on the use of the system and method for DNA sequence data collection and analysis, the system and method are capable of being applied to any single molecule level data corresponding to events occurring at atomic, molecular, ionic or assemblage sites. The inventors have found that the system and method are also well suited for detection formats with limited viewing fields such as TIRF limiting viewing field, wave-guide limited viewing field, channel limited viewing fields, or any other method of restricting the volume or field being detected by the detector or imaging apparatus.

The methods of this invention are well suited for detecting fluorescent resonance energy transfer (FRET) fluorescent events between a donor and an acceptor or plurality of acceptors, especially FRET fluorescent events associated with nucleic acid sequencing complexes including a donor labeled polymerase and an acceptor labeled nucleotide. For further details of sequencing technologies involving FRET strategies, the reader is directed to U.S. Pat. Nos. 6,982,146; and 7,056,661 and patent application Ser. Nos. 09/901,782 and 11/648,723, and abandoned patent application Ser. Nos. 11/007,642 and 11/648,107, incorporated herein by reference.

In certain embodiments, the inventors have applied the system and method to the identification and analysis of spots (fluorescent light) derived from individual DNA replicating complexes within a viewing field of an imaging apparatus. The method and associated software is designed to:

1) correctly identify a position or location of each fluorescently active species in each data channel or quadrant view of a viewing volume or field. The identities are based on single molecule fluorescent properties including:

a) intensity of the fluorescent signal relative to background, and b) size of an area associated with signal, e.g., number of pixels or data elements containing the signal, for each identified molecule, where the size can be fixed or adjustable, where the background is determined locally from an average intensity of pixels or data elements surrounding each area, e.g., a ring of 2 pixels removed from the area that define the "core" of each signal, where the background element selection criteria can be fixed or adjustable;

2) correlate or register positions of molecules in each quadrant or data channel to determine whether a molecule in one quadrant is the same molecule observed in another quadrant. The correlation or registration of molecules within each quadrant or data channel is facilitated by placing a grid on the viewing volume for overlap and proper correlation or registration. Correction algorithms such as rubber sheeting software can be used to correct for image distortions in the different quadrants or channels;

3) track and graphically present information about:

a) a length of time a fluorophore is detected, and b) an intensity of the fluorophore over the time period (length of time the fluorophore is detected);

4) plot intensities ratios between molecules observed in each quadrant or channel (signal intensities observed in each quadrant for an individual location in the viewing field, which corresponds to fluorescing species associated with the location such as a donor labeled replication complex and incorporating labeled nucleotides). This step really starts the base identity analysis of this method. The ratios are used to determine a confidence of a base call, i.e., each base call is assigned a confidence value.

5) time correlate spot data. For a spot to be a TRUE sequencing complex, there should be a connection of data points over time, producing a line of data associated with a single active replicating complex or sequencing source. Timing associated with the data line creation is generally an adjustable feature of the software, but can be fixed for system run under substantially similar conditions, conditions that generate data the is consistent and substantially reproducible. Timing generally depends on reaction conditions such as buffer, substrate concentration, enzyme concentration, temperature, viscosity, template and primer sequences, etc.). Timing of modified or labeled nucleotide or monomer incorporations will also be used to assign a confidence value to a base call. For example, when the donor can move out of the viewing volume during base extension, e.g., a system where the primer or template is immobilized on a surface or confined in a structure, then a penetration depth of light via TIRF (100 nm) generally permits detection of about 300 incorporation events per site, but for other systems, the number of detectable events may be in the thousands.

6) identify evidence of true incorporation events. Depending on the fluorophore or linker-fluorophore-nucleotide combination used and on the detection system configuration, a TRUE incorporation event is evidenced by wavelength shifts and intensity changes in the donor and acceptor channels (e.g., intensity increases for acceptors and intensity decreases for donors) during nucleotide incorporation and pyrophosphate (PPi) release. The donors are monitored and serve to punctuate an incorporation event. During FRET, the donor intensity is decreased (or be eliminated—decreased to zero). Thus, FRET events between a donor and acceptor result in a decrease in donor fluorescence and an anti-correlated increase in acceptor fluorescence.

7) determine and map localized signals. As the nascent DNA strand grows, its signal are NOT extended beyond the original 4 pixel area (assuming a 16 µm pixel size). Thus, the program may compare positional information between early and late data. Similarly, movement from an immobilized elongating molecule are not spread across more pixels.

8) substrate bursts of light not associated with a sequencing complex from the data file to reduce analysis time.

9) classify backgrounds. For certain sequencing systems, the background, data from pixels or data elements in the background surrounding a replicating complex, may become fairly standard or known. Thus, for a given system, the background may eventually become a known or standardized quantity. The background signal can then be used to set starting values and less computational time will need to be expended in determining localized background.

The present invention broadly relates to a system for collecting and analyzing chemical and/or physical event data occurring at one or a plurality of locations withing a viewing volume or field of an imagining apparatus. The system including a sample subsystem for containing a sample of be detected an analyzed, where the sample includes one atom, molecule, ion and/or assemblage or a plurality of atoms, molecules, ions and/or assemblages, at least one having detectable property that undergoes a change before, during or after one or a sequence of chemical and/or physical events involving the atom, molecule, ion or assemblage. The system also includes a detection apparatus having a viewing field that permits the detection of changes in the detectable property of one atom, molecule, ion and/or assemblage or a plurality of atoms, molecules, ions and/or assemblages within the viewing field. The system also includes a data processing subsystem connected to the imagining for collecting, storing and analyzing data corresponding to the chemical and/or physical events occurring at definable locations in the viewing field involving one or more atoms, molecules, ions and/or assemblages within the viewing field of the imagining subsystem. The data processing subsystem converts the data into classifications of events according the event type determined by a set of parameters defining or characterizing each event type.

The method broadly includes the step of receiving data from the detection apparatus comprising one or a plurality of data channels. The data channels can represent data associated with different parts of the viewing field of can represent data from the same viewing field, but separated by attributes such as frequency, intensity, phase, attenuation, flux density, any other detectable property, and mixtures thereof. Once the data is received, the data from each channels is stored. After and simultaneous with storage, the data in each data channel is registered or calibrated. This process matches locations in one data channel to corresponding locating in the other channels. Often times, the data in different channels does not directly line up, i.e., a location in the data in one data channel is not coincident with its corresponding location the another data channel. This distortion may occur over the entire image, in portions of the image, or may vary across the image. The registration process makes sure that all locations are registered between the channels—each location in one channel directly corresponds to the same location in all the other channels. If one data channel is a primary channel, then the primary channel data is analyzed to identify localized areas or regions—spots—within the viewing field that evidence a given value of the detected property. For example, if the primary channel represents immobilized or confined components of a reaction system such as a DNA replication complex, then the data in the primary channel is analyzed to locate the confined or immobilized components within the viewing field. Simultaneously or subsequently, data in the other channels is analyzed to determine if data in the other channels can be related to the spots in the primary data. If a spot is associated with a reactive species, then the other channels should include data evidencing reactions involving the identified reactive species. Otherwise, each data channel is analyzed for such localized areas or regions—spots, and locations are identified in which data in some or all of the channels evidence reactions—changes in detectable properties over time at each spot. Once the active spots and related data have been identified, then the event data is classified into a set of event types. After classification, a time profile of events occurring at each active site is determined. The time profile of events is then output to the user. This time profile can evidence a single event or a sequence of events. For sequences of events, the sequence can correspond to a sequence of monomer additions, a sequence of catalytic reactions, a sequence structural changes, a sequence of monomer removals, etc.

In certain embodiments, the present invention broadly relates to a method for analyzing fluorescent resonance energy transfer (FRET) events corresponding to interactions between a donor fluorophore associated with a first molecule or assemblage and an acceptor fluorophore associated with a second molecule or assemblage, e.g., a donor fluorophore associated with a member of a polymerase/template/primer complex and acceptor fluorophores associated with nucleotides for the polymerase. The method includes the step of collecting or receiving data from a viewing volume of an imagining apparatus such as an CCD or iCCD detection system, in real time or near real time. The data can be in a single data channel or a plurality of channels. In most embodiments, the data is collected in a plurality of data channels, each data channel representing a different frequency range of emitted fluorescent light, e.g., one channel can include fluorescent light data emitted by a donor, a donor channel, while other channels include fluorescent light data emitted by an acceptor channel, an acceptor channel, or by another donor, a second donor channel channel. In certain embodiments, a channel will exit for each different fluorophore being detected simultaneously. For DNA sequencing and in certain embodiments of the methodology of this invention, the number of data channels monitored is five (5). In other embodiments, the number of data channels monitored is four (4). In other embodiments, the number of data channels monitored is three (3), where three generally represents a minimally configured system. However, two (2) channels can be used provided that the acceptors are selected so that they can be separately identified based on detectable attributes of their signals e.g., intensity, frequency shifts, signal duration, attenuation, etc.

After data collection, the separate data channels are spatially correlated within the viewing volume so that active fluorophores can be spatially and temporally related, called calibration or registration. The goal of calibration is to determine the pixel coordinates in each quadrant that correspond to a single position on the slide or a single location within the viewing field—to make sure that the data in each channel is spatially coincident over the viewing field and through time of detection. For most of the data collected on the imaging systems used by the inventors, the inventors have been able to determine empirically that location distortions between channels comprises almost exclusively translations and rotations. In other systems, the distortions may be translations, rotations, shearing, stretching, compressing, screwing, twisting, etc. and the calibrating process must be able to register the data between the channels so that locations within one channel correspond to the same locations in the other channels.

The calibration procedure includes two principal components. Both components utilize image files comprising an average over a set of frames of a data stream from a data channel, where the set of frames can be the entire data stream collected or any subset thereof. A frames is data collected by the imagining apparatus over a given short period of time that is received by the processing unit and assembly into a temporal data set for each data channel. The frames generally represent average data over the collection time period depending on the imagining apparatus data collection and transmission speeds.

The first component is a visual tool that allows the quadrants or data channel averaged data or cumulated image to be overlaid with transparency to quickly check data alignment. This tool was constructed using standard MATLAB libraries.

The second component is an automated tool based on maximizing mutual information across the quadrants or data channels. Mutual information quantifies the predictive power that one image has for another. For example, knowing there is a bright spot in one quadrant should mean that there is a corresponding bright spot in one or more of the other quadrants or data channels. The component determines and outputs the rotation and translation operators that when applied to the data in one or more the channels produces the greatest mutual information between the quadrants.

This calibration process produces improved data calibration or registration. The process avoids the effects of individual pixels having poor brightness, spurious or missing data or other noise. The program encoding this second component was written in C++ and includes libraries from the standard ITK project libraries.

The method then includes the step of reading a configuration file and a corresponding open log file. After reading the configuration file and the open log file, calibrations, if any, are loaded from the command line. After loading the calibration information, a corresponding directory is read as specified in the command line with all subdirectories, for each one. This read step includes: (1) scanning for calibration stacks, and if there are some not matched by the available calibrations, generate new calibrations out of them; (2) scanning for stacks; if there are some, assume this directory is a slide; and (3) scanning the directory path for a date and slide name comprising reaction conditions such as donor identity, acceptor identity, buffers, etc.

The method also includes the step of looping over all stacks for every slide. The looping step includes: (1) finding calibration data by date and frame dimensions; (2) averaging all the donor frames in the stack or averaging the donor frames over an adjustable number of frames in the stack; (3) finding spots in the averaged donor data or quadrant; (4) applying the calibration data to the acceptor channels to find acceptor coordinates corresponding to each found donor spot; (5) identifying a 3×3 pixel array associated with each found donor spot in the donor and acceptor channels (although the method has been tuned to use a 3×3 array, the method can use smaller and larger array and the array size will depend on the detector system and on the system being detected); (6) collecting traces for each pixel in the array over the frames in the averaged data; (7) applying a pixel selection algorithm to the pixels in the array to select pixels that have a value above a threshold value; (8) averaging the selected pixels to form hybrid traces (signals); and (9) checking the donor traces for minimal requirements on lifetime and average intensity; and (10) discharging any found donor spots and associated acceptor data that does not meet these criteria.

The method also includes the step of computing the acceptor "lifetimes" for each found donor spot using two different smoothing algorithms, a regular Savitzky-Golay smoother, which is adapted to identify short-lived, sharp signals, and a smart smoother, which is adapted to identify long-lived, weak signals and "broken" signals.

The method also includes the step of creating lists of acceptor events from the identified acceptor lifetimes.

The method also includes the step of adjusting boundaries of the acceptor events using numeric derivatives using a similar Savitzky-Golay process to achieve maximum correlation/anti-correlation with the donor.

The method also includes the step of computing a set of parameters for every acceptor event and assigning the every acceptor event a score based on these parameters as described below.

The method also includes the step of joining adjacent segments from the acceptor event lists, and find and resolve overlaps (if any) as describe in detail below. For instance, if there is a long event overlapped by several shorter events, check their scores as to decide which case describes the data better: one large event or a series of smaller ones.

The method also includes the step of using the resulting acceptor event list as a list of FRET event candidates: for every candidate, compute a set of FRET event parameters, such as FRET efficiency, acceptor and donor signal to noise ratios, probabilities, boundary anti-correlation coefficients, etc. as described in more detail below. The method determines if these parameters meet minimal criteria (specified in the configuration file), and if they do, accept this candidate as a FRET event for output.

The method also includes the step of sorting spots of the current stack by how "event-reach" they are, and output an event-list for the whole stack. Also, add the detected events to the slide's event list. The method also includes the step of after finishing with all the stacks in the slide, generating the combined report containing results from every spot of every stack in the slide.

Another embodiment of the methodology of this invention is described below invention Main Routine The process states with the construction of workspace and data structures to support the analysis. The workspace includes configurational data, current state information such as slide/stream information stored in a separate structure, data result structures, etc.

Next, the process reads the default configuration file, if present in the same directory. The configuration file includes a set of configurational parameter data, which are throughout the process by the routine to find needed configurational data. The process then scans a command line for a log file of options. If a log file is present, then the process opens the specified log file. If the log file is not present, then the process attempts to open a log file in the directory specified by the configurational parameter data. If no log file is found in this directory, then the process attempts to open a log file in the current working directory. If that fails, the process exits with an error message. The log file is opened with shared reading options, which is required for proper inter routine communications and proper interactions with Windows operating system routines.

The process then checks the command line for the first argument, which is supposed to be a sub-directory in the source root directory, specified by the configurational parameter data. If not present, the process prompts the user to enter the sub-directory from the standard input (generally a keyboard).

If the command line has more than one argument, parse the extra arguments. The extra arguments can be either additional configurational files, an user-specified log file, or a no calibration flag. The last option overrides configurational parameter data, and specifies whether the routines in the process are allowed to use the cached calibrations either found in the calibration directory given in the configurational parameter data or default calibrations given in the configurational parameter data separately for each frame size. If the configurational parameter data or the command line sets no calibration flag on, instructs the process not to use the cached calibration data. In this case, original calibration stacks must be present in the directory starting with date of the slide, and a new calibration is generated every time subsequent routines require calibration. If the calibration stacks are not present, the process fails with the error message "No calibration present".

If the first command argument (or user input) is a valid and corresponds to an existing subdirectory in the source data structure directly, then the process recursively scans the subdirectory for stacks/slides data. The process then clean up and exits.

Process Directory Routine

This routine scans the directories for calibration data and slide information. The routine then constructs corresponding output directory names. Assuming the current directory correspond to data derived from a slide, the routine reads the list of stack files contained in the directory. If the list is not empty, the routines processes each stack file. The routine then reads the list of FITS files (FITS files stand for Flexible Image Transport System files) and generates slide wide statistics for reporting purposes. The routine then reads the list of associated sub-directories, and call processes the subdirectories recursively extracting the data contained in the subdirectories.

Scan for Calibration Data Routine

If directory name start with the proper date pattern, then the routine reads the date pattern from the directory name; otherwise, the routine returns control to the calling routine. The routine then scans the directory configurational parameters data for calibration data matching the date pattern and downloads any matches found. The routine next scans the current directory for stack and fit data files containing no more than 3 planes or frames of data. The routine then checks if calibration data for the given frame size and date is present. If the calibration data is not present, then the routine queues the file for generation of new calibration data. A queue is necessary because there can be more than one calibration stack so that the routine implemented in add calibration data can chose the best calibration stack by comparing the number of donor spots detected in each stack. The calibration data is generated in context and is represented by a data structure containing overlays and spot lists from each quadrant, generated by the find spot routine described herein. The routine then checks the calibration queue, and generates calibration data via a generate calibration routine that determines the transformation needed to register pixel locations in one channel with corresponding pixel locations in the other channels. The transform is generally comprised of simply a translation and a simply rotation. However, the transformation can be much more complex and is constructed to map pixels from one channel into corresponding pixels in other channels.

Generate Calibration Data Routine

The routine starts by opening a stack file. The routine then applies non-standard geometry settings if specified. The routine then checks to ensure that the file is valid, i.e., the file includes 16-bit non-compressed data, has a known frame size, has enough frames, and has an ok integration cycle time. Search for calibration data associated with the frame size and the date/time of the file collection. The calibration is cached as defined above. If all conditions are met and the calibration is found, then allocate the data structures needed for detection processing and forward control to the stack processing routines.

Process Stack Routine

The stack processing routine reads and averages frames from the stack file to generate an overlay. The routine then generates an overlay picture for the donor quadrant and searches for donor spots in the donor quadrant using the find spot routines. The routine then uses the existing picture object to mark the initial donor spots.

The routine then creates signal to noise structures for individual pixel traces, one per channel per spot. The routine then applies the calibration transform to register the acceptor pixel coordinates to the donor channel pixel coordinate system. The routine then reads the stack file again, collecting data samples at each frame for the identified pixel traces. For each spot, the routine applies the hi-pass filter to the donor traces and performs the donor pixel selection and generates the donor hybrid traces.

Next, the routine applies the hi-pass filter to acceptor traces, and performs the Acceptor pixel selection and generates acceptor hybrid traces. The acceptor hybrid trace routine is repeated for each acceptor channel. The routine then stores the hybrid traces into a signal structures, which is stored as part of the signal to noise structures.

The routine then filters out spots that do not satisfy the donor lifetime and the donor S/N ratio conditions from the initial data file. The routine then generates an overlay picture of the donor quadrant with spots found/filtered out. The routine then writes the results as the list of donor spots.

The routine then sends the list of donor spots to the FRET analysis routines. Next, the routine generates an overlay picture of the donor quadrant with active spots, and outputs text data files related to the current stack.

FRET Analysis Routine

The FRET analysis routine first allocates structures to keep the results from the analysis. The routine then, for each spot in the donor spot list, makes a separate array of signal structures by copying the signal data structure from the input signal to the noise data structure previously stored. The FRET analysis routine then calls the create donor model routine. The create donor model routine then adds a dynamic list of acceptor data traces from corresponding pixels in the acceptor channels. The FRET analysis routine then generates a list of FRET event candidates from the donor spot list. The routine then stores the resulting event list into previously allocated data structures. The routine then counts the number of high probability events and low probability events in the list, and determines the highest probability to set a spot efficiency entry on the current spot. The routine then sorts the arrays based on spot efficiency entry, the number of high probability events, the number of low probability events, and the highest probability. The index within this sorted array becomes the spot ranking.

For each spot, the routine creates a list of donor events by calling a construct donor events routines. This routine computes adjusted donor lifetimes by calling a compute adjusted lifetime routine. The routine then stores all the data such as event lists, noise level, donor lifetime, adjusted donor lifetime, etc. into a previously allocated entry in the spot list structure, associated with current slide. The stored information becomes persistent across the whole slide, while the rest of data is deallocated.

For each spot, the routine detects donor around events stuff, and store it into a slidewide persistent area and generates signal and FRET detection trace pictures if necessary. The routine then generate as rich spot file that contains spot info for so-called rich spots. A rich spot is a spot that contain at least one FRET event. The routine also generates an activity picture, with the rich spots colored.

SIGNAL Data Structure

The signal data structures is a data structure containing hybrid traces of one of the channels, donor, acceptor 1, acceptor 2, etc. The elements of the data structure include:

| | |
|---|---|
| accno | channel number - 0 for the donor channel, 1 for the first acceptor channel, 2 for the second acceptor channel, etc. |
| x, y | spot coordinates - coordinates of the middle pixel of the 3 × 3 pixel spot array |
| mask | bit mask indicating which individual pixels from the 3 × 3 area were included in constructing the hybrid trace |
| nsamp | number of data samples in the trace (same as number of frames in the stack file) |
| nlvl | noise level computed as standard deviation (sometimes scaled by a factor) of the noise channel |
| *sigbuf | buffer containing hybrid trace data samples |
| *noise | buffer containing hybrid noise data samples |
| ACC-DETECTOR *first | first element in the list of additional data structures, usually related to a particular detection algorithm |

ACC-DETECTOR Data Structure

The ACC-DETECTOR data structure containing additional information about a hybrid trace, such as intermediate data from different types of detectors, simulation data or donor model. The data structure includes the following elements:

| | |
|---|---|
| struct tag__ACC__DETECTOR *next | a pointer to the next ACC__DETECTOR object in the list, or NULL if this is the last object |
| detector | detector type, one of the following: |
| 0 | undefined detector type |
| DETECTOR__LONG | long lived event candidate detector |
| DETECTOR__SHORT | short lived event candidate detector |
| DETECTOR__DONOR__MODEL | Donor Model |
| DETECTOR__SIMULATION | Simulation data (such as original trace before blending with noise) |
| nlvl | noise level used in particular computations (usually is the nlvl from SIGNAL scaled by a factor) |
| *sigsmooth | Hybrid trace data after smoothing |
| *sigder | Digital derivative |
| *life | Lifetime buffer indicating which data samples represent on or off state of the channel |
| double stdac | Standard deviation of the derivative |
| void (*destructor)(struct-tag-ACC-DETECTOR *ad) | pointer to a function which is called wnen the object is deallocated. An actual implementation of ACC__DETECTOR object may contain some extra data, which is sometimes allocated dynamically. Since the control logic is not aware of such data, an implementation-specific code must be provided to handle that. When the standard delete__acc__detector( ) function is called, it checks whether this pointer is not NULL, and if so, calls that function, which is supposed to take care of any implementation-specific de-initialization. |

When a routine (such as a detection routine) needs to associate some extra data with a given signal, the routine constructs an ACC-DETECTOR object, and adds it to the list of ACC-DETECTOR objects, pointed to by '->first' member of the SIGNAL data structure.

Construct Donor Model

The model constructs a Smart Smoother object for subsequent operations via construct smart smoother routine. The routine allocates a donor model object. The model smart smoothes the original donor trace, and then compute its first derivative using a Savitzky-Golay (SG) fitting routine. The model then computes a standard deviation of the derivative and stores it in the donor model object. This derivative will be used to detect slow changes in the donor trace.

The model then calls a donor lifetime routine to compute the donor's derivative lifetime. It computes another "finer" derivative of the original trace using a different SG smoother to detect fast changes in the donor trace. The model then computes segments, where both derivatives go outside their standard deviations either way (positive or negative), and then combines detected segments from both processes.

The model then the results representing segments, where fast donor changes were detected (high derivative value) are stored in life time buffer.

The SG-smoothed original donor trace is stored in signal smoothed buffer for subsequent operation using the SG-smoother from the Smart Smoother object.

The model then calls a routine to create initial static segments, which examines each segment having a high-derivative value, to find the sample index at which the change is highest (max/min derivative), and to break down the entire donor trace into segments with the boundaries set at those 'high-change' points.

The model typically creates a large set of tiny segments, which need certain types of optimization to determine if neighbor or adjacent donor segments (i.e., donor segments to the immediate right or left of a particular donor segment) are substantially different. If adjacent segments are not substantially different, the adjacent donor segments are joined into a single larger segment. The term substantially different is determined by applying a variety of criteria, such as close enough average value, a tiny segment in between two larger ones with close averages, etc. In addition, the model decides whether each segment represent donor on state or donor off state.

Finally, the model iteratively calls a finalize donor model routine a few times (each time the routine iteratively improves the segment joining process) to compute final donor lifetimes and to construct a best polynomial fit of the appropriate donor segments.

Detect Acceptor Events Routine

For each acceptor channel, the routine calls a subroutine to generate a list of long lived acceptor event candidates using the long lived event detection algorithm, an algorithm optimized to identify long lived events. Next, the routine calls a subroutine to generate a list of short lived event candidates using the short lived event detection algorithm, an algorithm optimized for to identify short lived events. The routine then join all the event candidate lists into a single event candidate list, where the total number of candidates in the list is 2 times number of acceptor channels—long lived events and short lived events per channel. The routine then calls a subroutine adapted to exclude conflicting entries in the joint list of event candidates as describe below. The routine then returns list of event candidates to its calling routine.

Detect Long Lived Acceptor Events Routine

This routine constructs a Smart Smoother object. The routine first checks to determine whether ACC-DETECTOR objects of type DETECTOR-LONG are already attached to both donor and acceptor SIGNAL objects. If not, the routine create new ones, fills them with smoothed data, and attaches the objects the SIGNAL objects. The routine operates by calling a static routine to determine rough acceptor lifetimes to fill the lifetime buffer. Zero values in the lifetime buffer represent signal in the channel that are in an OFF state, while non-zero values in the lifetime buffer represent signal in the channel that are in an ON state. The routine then reads the acceptors events from the lifetime buffer to create an initial array of event candidates stored as ACC-EVENT objects by scanning for non-zero segments in the lifetime buffer. The routine then optimizes the acceptor event segments by joining adjacent segments iteratively based on a set of joining criteria to form joined acceptor event segments. This process is a more thorough test to determine whether adjacent 'on'-segments should be joined together because they belong to a single event, accidentally broken apar by noise spikes. The routine then calls a subroutine to determine and adjust event boundaries, where the subroutine uses the Derivative Anti-correlation (DAC) function to adjust boundaries of the event candidates.

For each event candidate, the routine also computes a variety of event parameters like average intensities, signal to noise ratios, etc., and compute an event, which is used later to evaluate how "good" this event candidate is. The event score is computed in static according to the following formula:

$$f*sqrt(x1*x1+x2+x3)-0.5$$

where x1 is the acceptor signal to noise ratio, x2 is the product of differential acceptor and donor signal to noise ratios at the beginning and x3 is the product of differential acceptor and donor signal to noise ratios at the end of the event. If the product is negative, it is multiplied by −0.25. The coefficient f depends on the event duration and is computed according to the following formula:

$$1.+2.*(1.-exp(-dl*dl))$$

where dl is the ratio of the event duration to a long scan distribution parameter in the configurational parameter data. The coefficient f is to provide a configurable boost to the score of longer lived events.

The routine then cleans up and return the resulting list of acceptor events to its calling routine.

Detect Short Lived Acceptor Events Routine

This routine constructs SG smoother objects for a signal trace (function) and its derivative. First, the routine checks whether acceptor detector objects of type short lived detector objects are already attached to both donor and acceptor SIGNAL objects. If not, the routine create new ones, fills them with smoothed data, and attaches them to the appropriate SIGNAL objects.

The routine operates by calling a static subroutine adapted to to fill in a lifetime buffer. Zero values in the lifetime buffer represent channel signals in an OFF state, while non-zero values in the lifetime buffer represent channel signals in a ON state. Next, the routine calls a subroutine adapted to join lifetime segments, which comprises segments separated by short interruptions, generally by noise.

The routine then calls a subroutine adapted to split up lifetime segments, which were unjustifiably joined by accidental noise or smoothing algorithm peculiarities. The routine then calls a subroutine to create and initial array of event candidates stored in an acceptor event objects by scanning for non-zero segments in the lifetime buffer. Next, the routine calls a subroutine to adjust short event boundaries, where the subroutine uses the Derivative Anti-correlation (DAC) function to adjust boundaries of the event candidates.

For each event candidate, the routine calls a subroutine adapted to compute a variety of event parameters like average intensities, signal to noise ratios, etc., and compute the event acceptor score, which is used later to evaluate how "good" this event candidate is.

Similar to a long lived event score, the acceptor event score is computed in according to the formula:

$$sqrt(x1*x1+x2+x3)-2.0$$

where x1 is the acceptor signal to noise ratio, x2 is the products of differential acceptor and donor signal to noise ratios at the beginning of the event and x3 is the product of differential acceptor and donor signal to noise ratios at the end of the event. If the product is negative, it is multiplied by −0.25. If the event is in the beginning of the trace, x2 is forced to the value of 2.0; likewise, if the event is at the end of the trace, x3 is forced to the value of 2.0. This forcing value process reflects the fact that the anti-correlation status is not known under these circumstances.

The routine then cleans up and return the resulting list of acceptor events to its calling routine.

Resolve Acceptor Event Overlap Routine

The purpose of this routine is to eliminate overlapping event candidates from the list of acceptor events. The routine first sorts the input array of event candidates in order of event starts. Next, the routine breaks down the array into sub-arrays containing conflicting areas. The routine operates by adding a first event to the current sub-list. The routine then iterates over subsequent events until no events overlap with any events in the sub-list, adding each overlapping event to the list. If no new overlapping event are found, the routine closes that sub-list, selects an event and creates a new sub-list of overlapping events. The routine repeats this process until all events have been processed, creating a set of sub-lists including overlapping events. The sub-lists contain a set of conflicting (overlapping) event candidates, but each sub-list is independent of events in any other sub-list, i.e., the sub-lists are distinct with no shared events.

For each conflicting or overlapping area sub-list, the routine calls a subroutine to find best rated non-conflicting sub-list of event candidates. The routine operates by sorting events in the conflicting sub-list by their acceptor event score. Next, for every event in the sub-list, the routine constructs a further sub-list containing only events, which do not conflict with the starting event. The routine then compute the resulting score of every sub-list as the sum of adjusted scores of their events, then selects the sub-list with the highest adjusted score.

The 'adjusted score' is computed according to the following formula:

$$score*2.0*bias$$

where score is the acceptor event score and bias is the configurational parameter data element bias N (N is the acceptor channel number) and is set to bais N for segments from the long lived routine or 1-bias N for segments from the short lived routine. Using this process, it is possible to manipulate scores and eligibility of events identified in the short lived detection routines versus events identified in the long lived algorithm by adjusting the value of the parameter bias N.

After resolving overlapping event data, the routing join the non-conflicting sub-lists into a single list of event candidates, and return control to its calling routine.

Detect FRET Events Routine

The purpose of this routine is to compute FRET event parameters for every input event candidate. The routine also applies certain basic criteria to filter out any obvious non-events or trash events.

The routine operates by computing DAC functions based on derivatives from the acceptor detector objects of type short lived events. The routine then creates a 'finer' SG-smoother/derivative, and compute DAC functions based on the smoother output.

Next, for every event candidate, the routine adjust event boundaries. If the resulting duration does not exceed a parameter maximum short event in the configurational parameter data, the routing repeats event boundary adjustments with the 'finer' DAC functions.

Using finer DAC functions to analyze short lived events is necessary to avoid problems such as the 6-frame problem. The six frame problem occurs with standard smoother used to analyze short lived signals. The DAC functions, which are based on donor and acceptor derivatives, have peaks at the event boundaries, and the peaks are not infinitely narrow, but have certain widths. If the event duration is less than or equal to about two times the boundary widths, then adjusting the event boundaries using the standard smoothing routines gives inaccurate results. As the event duration gets shorter, the adjusted duration does not, which creates certain errors. To reduce these errors to a tolerable level, 'finer' digital derivatives/DAC functions are used.

Next, for every event candidate, after basic FRET event parameters (e.g., start, duration, acceptor number) are set, the routine computes a whole set of parameters, associated with FRET events.

Then, for every FRET event, the routine determines if the computed probability is smaller than an desired or allowed minimum value given in the configurational parameter data as the low probability limit. If the probability of the event is less than the low probability limit, then the event is removed from the final FRET event list. The routine then compacts the FRET event list.

The routine then sets the parameters il and ir for each event. The parameter i is the acceptor intensity at the beginning of the event, while ir is the acceptor intensity at the end of the event. The routine sets the values of il and ir equal to the average acceptor intensity value during the event, if the duration or length of the event is less than 20 frames, set both values equal to average acceptor intensity. Otherwise, the routine first best fits the acceptor trace during the event with a straight line. The routine then set the value of il to the value of the straight line at the beginning of the event and the value of ir to the value of the straight line at end of the event. Of course, an ordinary artisan can recognize that the best fit routine can be to a polynomial of any dimension, provided that il and ir are set to the polynomial values at the beginning and end of the event, respectively.

Finally, the routines performs cleanup operations and returns the FRET event list to is calling routine.

The process of this invention utilize routine that in certain embodiment includes data structures having the following data.

Output File Format

Slide Events Data

The following table tabulates the slide event data stored in the data structures.

| Label Name | Description |
| --- | --- |
| Stream | Stream ID. Normally, 2-digit number taken from the stack file name. For example, if the stack name is Stream05, the stream ID is 05. |
| Rank | Spot trace rank within the slide based on how event-rich is the spot. Lower number means richer spot. |
| DonCol | Donor X-coordinate of the spot. |
| DonRow | Donor Y-coordinate of the spot. |
| Start | Start of the event in ms. |
| Length | Duration of the event in ms. |
| Acc | Acceptor number of the acceptor causing the event. Currently can be either 1 or 2, but in the future releases it will also take values 3 and 4. |
| Prob | Event probability. A value in the range 0 . . . 1.0, indicating how "good" is the event, that is, how reliably it is detected. The closer the value to 1, the more reliably the event is detected. |
| FRETEff | FRET Efficiency computed as AiSN/(AiSN + DSN), where AiSN is the acceptor signal to noise ratio AiInt/AiNL (i is the acceptor number, same as Acc), and DSN is the donor dark state signal to noise ratio, either DLR/DNLC or DRL/DNLC, depending on which difference is higher, DLL − DLR or DRR − DRL. |
| Style | Event style. Possible values are:<br>0 - No correlation between donor and acceptor of any kind (both LACC and RACC are above −1 but below 2);<br>1 - Positive correlation at least at one end (either LACC, or RACC, or both are below −1, while none of them is above 2);<br>2 - Negative (anti-) correlation at one end (one of the LACC or RACC is above 2, while the other is not);<br>3 - Negative (anti-) correlation at both ends (both LACC and RACC are above 2.) |
| Hi | Indicates whether the event is hi-prob. If Prob is greater than the value of the configurational parameter hi_probi, then Hi is 1, otherwise, 0. |
| LACC | Anti-correlation coefficient on the left (at the start of the event), calculated as product of acceptor signal to noise ratio AiInt/AiNL and donor differential signal to noise ratio (DLL − DLR)/DNLL. |

-continued

| Label Name | Description |
| --- | --- |
| RACC | Anti-correlation coefficient on the right (at the end of the event), calculated as product of acceptor signal to noise ratio AiInt/AiNL and donor differential signal to noise ratio (DRR − DRL)/DNLR. |
| Dark | Average donor intensity during the event. |
| DonProb | Donor "probability" computed as $(1. - \exp(-DSN^2 * WTD)) * (1. - \exp(-2 * (DInt/DNL)^2))$ where DSN is donor differential signal to noise ratio, either (DLL − DLR)/DNLL or (DRR − DRL)/DNLR, whichever is higher; WTD is a coefficient equal to 0.4 for short events (shorter that configurable max_short_event), or 0.71 for long events; DInt is either DLL or DRR, depending on which differential signal to noise ratio is higher. |
| Ac1Prob | Acceptor 1 "probability" computed as $1. - \exp(-(A1Int/A1NL)^2 * WT1)$, where WT1 is a coefficient equal to the product of the configurable parameter wt_ac1 and a value of 0.4 for short events or 0.71 for long events. |
| Ac2Prob | Acceptor 2 "probability" computed as $1. - \exp(-(A2Int/A2NL)^2 * WT2)$, where WT2 is a coefficient equal to the product of the configurable parameter wt_ac2 and a value of 0.4 for short events or 0.71 for long events. |
| NL | Number of donor data samples preceeding the start of the event, that were used to calculate DLL (see below.) |
| DLL | Donor Intensity right before the start of the event. If NL is large enough (larger than 20), an average is computed, otherwise, a peak value of fine-smoothed data less DNL/√v2. |
| DNLL | Donor noise level right before the start of the event. Normally taken from the donor model, and is equal to the standard deviation from the polynomial fit at the corresponding donor segment. |
| DLR | Donor Intensity right after the start of the event. |
| DNLC | Donor noise level during the event. It is taken from the donor model, and frequently equal to DNL. |
| DRL | Donor Intensity right before the end of the event. |
| NR | Number of donor data samples following the end of the event, that were used to calculate DRR (see below.) |
| DRR | Donor Intensity right after the end of the event. If NR is large enough (larger than 20), an average is computed, otherwise, a peak value of fine-smoothed data less DNL/√v2. |
| DNLR | Donor noise level right after the end of the event. Normally taken from the donor model, and is equal to the standard deviation from the polynomial fit at the corresponding donor segment. |
| DNL | Donor Background Noise Level. Computed as the standard deviation of the donor "noise" hybrid trace. |
| A1Int | Average (for long events, longer than max_short_event) or peak acceptor 1 intensity during the event. |
| A1L | Acceptor 1 Intensity at the start of the event. Computed by modeling acceptor with a straight line best fit. |
| A1R | Acceptor 1 Intensity at the end of the event. Computed by modeling acceptor with a straight line best fit. |
| A1NL | Acceptor 1 background Noise Level. Computed as the standard deviation of the acceptor 1 "noise" hybrid trace. |
| A2Int | Average (for long events, longer than max_short_event) or peak acceptor 2 intensity during the event. |
| A2L | Acceptor 2 Intensity at the start of the event. Computed by modeling acceptor with a straight line best fit. |
| A2R | Acceptor 2 Intensity at the end of the event. Computed by modeling acceptor with a straight line best fit. |
| A2NL | Acceptor 2 background Noise Level. Computed as the standard deviation of the acceptor 2 "noise" hybrid trace. |

Referring now to FIG. 1, a graphical illustration of certain of the parameters that are defined for an event are shown. The parameters are defined in the table above.

Donor Spots Data

Tab delimited file. The first line contains tab delimited text labels, the rest, data, one line per donor trace.

| Label Name | Description |
| --- | --- |
| Stream | Stream ID. Normally, 2-digit number taken from the stack file name. For example, if the stack name is Stream05, the stream ID is 05. |
| Rank | Spot trace rank within the slide based on how event-rich is the spot. Lower number means richer spot. |
| DonCol | Donor X-coordinate of the spot. |
| DonRow | Donor Y-coordinate of the spot. |
| AvgInt | Average Donor Intensity during Lifetime. |
| LifeTm | Donor Lifetime (ms). |
| DE | Ratio (Total Donor Event Duration)/(Total Trace Duration). |
| DEAC | Ratio (Total Anti-Correlated Donor Event Duration)/(Total Trace Duration). |
| Cnt | Number of Donor Events detected. |
| CntAC | Number of Anti-Correlated Donor Events (that have a FRET event match). |
| NPDon | Number of Donor pixel traces selected by Pixel Selection and averaged into Hybrid Donor Trace. |
| NPAc1 | Number of Acceptor 1 pixels selected by Pixel Selection for averaging into Acceptor 1 Hybrid Trace. |
| NPAc2 | Number of Acceptor 2 pixels selected by Pixel Selection for averaging into Acceptor 2 Hybrid Trace. |

Donor Events Data

Tab delimited file. The first line contains tab delimited text labels, the rest, data, one line per donor event. A Donor Event is defined as a temporary switch to dark state of limited duration, which happens in the middle of the trace (that is, there is always excited donor before and after that event.)

| Label Name | Description |
| --- | --- |
| Stream | Stream ID. Normally, 2-digit number taken from the stack file name. For example, if the stack name is Stream05, the stream ID is 05. |
| Rank | Spot trace rank within the slide based on how event-rich is the spot. Lower number means richer spot. |
| DonCol | Donor X-coordinate of the spot. |
| DonRow | Donor Y-coordinate of the spot. |
| DonProb | Donor "probability", computed in a way similar to slide_events:DonProb. |
| Start | Start time of the Donor Event (ms). |
| Length | Duration of the Donor Event (ms). |
| AC | Anti-Correlation. If 'Y', the Donor Event has a match of a detected FRET Event. |

Donor Segments Data

Tab delimited file. The first line contains tab delimited text labels, the rest, data, one line per donor segment.

| Label Name | Description |
| --- | --- |
| DSegId | Slidewise unique number, identifying a Donor Segment. |
| Stream | Stream ID. Normally, 2-digit number taken from the stack file name. For example, if the stack name is Stream05, the stream ID is 05. |
| Rank | Spot trace rank within the slide based on how event-rich is the spot. Lower number means richer spot. |
| DonCol | Donor X-coordinate of the spot. |

-continued

| Label Name | Description |
| --- | --- |
| DonRow | Donor Y-coordinate of the spot. |
| Start | Start time of the Donor Segment (ms). |
| Length | Duration of the Donor Segment (ms). |
| Excited | 1 - excited, 0 - dark. |
| Int | Average Intensity. |
| Dev | Deviation of the polynomial approximation from the average intensity. Valid only for large (80 frames or more) excited segments. |
| NL | Noise Level within the segment. Based on standard deviation of the actual intensity from the polynomial approximation (or average intensity if no PA). |

Donseg Events Data

Tab delimited file. A Donor Segment Event is defined as a temporary change in the donor behaviour within a defined Donor Segment. If the Donor Segment is dark (Excited=0), the event is a temporary switch to excited state. If the Donor Segment is excited (Excited=1), the event is a temporary switch to dark state.

There can be zero to many Donor Segment Events in each Donor Segment.

| Label Name | Description |
| --- | --- |
| DSegId | Donor Segment ID of the Donor Segment where this event belongs in. |
| Start | Start time of the Donor Segment Event (ms). |
| Length | Duration of the Donor Segment Event (ms). |
| Int | Average Intensity during the event. |

Donor Around Event Data

Tab delimited file. The first line contains tab delimited text labels, the rest, data, one line per FRET Event. Line-to-line match with slide_events.dat.

| Label Name | Description |
| --- | --- |
| Stream | Stream ID. Normally, 2-digit number taken from the stack file name. For example, if the stack name is Stream05, the stream ID is 05. |
| Rank | Spot trace rank within the slide based on how event-rich is the spot. Lower number means richer spot. |
| DonCol | Donor X-coordinate of the spot. |
| DonRow | Donor Y-coordinate of the spot. |
| Start | Start time of the FRET Event (ms). |
| Length | Duration of the FRET Event (ms). |
| LDur | Duration of portion of the Donor Segment immediately preceeding the FRET Event (ms). |
| LDInt | Average Intensity of the Donor Segment on the left (same as donor_segments:Int). |
| LDDev | Deviation of the polynomial approximation from the average intensity of the Donor Segment on the left (same as donor_segments:Dev). |
| LDNL | Noise Level within the Donor Segment on the left (same as donor_segments:NL). |
| RDur | Duration of portion of the Donor Segment immediately following the FRET Event (ms). |
| RDInt | Average Intensity of the Donor Segment on the right (same as donor_segments:Int). |
| RDDev | Deviation of the polynomial approximation from the average intensity of the Donor Segment on the right (same as donor_segments:Dev). |
| RDNL | Noise Level within the Donor Segment on the right (same as donor_segments:NL). |

BRIEF SUMMARY OF SEQUENCING TECHNOLOGY

The sequencing technology utilized for analysis in this application produces fluorescence events at multiple wavelengths in a large number of individual sequencing complexes (polymerase/template/primer/nucleotides). The primary analysis centers around identifying positions of the individual sequencing complexes generally within a small viewing volume or field associated with an experimental sample. That is, the actual sample volume may be disposed over a fairly large area of a surface of a substrate or in a fairly large volume of a container and the system is adapted to only view a small volume or field of the actual sample volume. However, in certain embodiments of sequencing systems, the viewing field could be the entire small volume if the sample is sufficiently confined to restrict its overall volume. The technology is adapted to follow fluorescence intensity at multiple wavelengths over time within the viewing volume, and extracting sequence information from the coordinated, time-dependent changes in fluorescence at each wavelength (base calling). Although the imager used specifically in this application is a frame-based CCD camera, data acquisition can be considered a parallel array of single detectors, each monitoring one sequencing complex. The inherently parallel nature of simultaneous sequencing (estimated to be several hundred up to 1000 individual sequencing complexes) occurring within the viewing field demands efficient use of computational resources, particularly where our goal is to have a near real-time output. While the inventors have not yet needed to rely on parallel computing to produce results quickly, the technology lends itself to straightforward parallelization—pipeline or matrix processing. Computationally intensive routines were implemented in C++ in conjunction with standard functions in MatLab as well as MPI libraries (Gropp et al., 1994). The routines can be run on any acceptable computer operating system platform such as Windows, Linux, Macintosh OS X, or other windowing platforms.

BRIEF OVERVIEW OF SIGNAL PROCESSING METHODOLOGY

Calibration

Each sequencing complex produces fluorescence signals at multiple wavelengths or frequencies. Individual fluorophores produce signals in specific wavelength or frequency ranges or bands of the electromagnetic spectrum. Thus, each sequencing complex will include more than one fluorophore, at least one donor and at least one acceptor. Each wavelength band is independently monitored. In certain detection systems, the optical system splits the spectrum and directs various wavelength or frequency bands to different quadrants of a single CCD imager. Calibration is needed to determine pixel coordinates within each quadrant or data channel of the CCD that correspond to a single sequencing complex, i.e., the calibration permits the individual quadrants to be spatially correlated or registered—locations in one quadrant correspond to locations in the other quadrants. The necessary transformation is primarily a translation operation, however, a small amount of rotation may also occur requiring correction due to misalignments in the optical system. Although in the CCD system being currently used translation and rotation are the major components of the calibration operation, in other systems, the calibration may have to correct for many other types of data distortion such as twisting, stretching, compressing, skewing, etc. In the imager used in this application, the inventors have found that light emitted from each sequencing complex is generally localized within a single pixel or a small array of contiguous pixels within the frames and quadrant rotations of even a fraction of a degree are sufficient to mis-align pixel positions at the ends of the sensors. Additionally, small deviations in the optical system over time requires that the system be calibrated on a daily basis. Of course, the system can be calibrated more frequently if desired. While it is desirable to minimize these errors inherent in the hardware, the inventors believe that all systems will have some type of errors, such as alignment errors, that require calibration. To determine the correct image transformations, the inventors currently use a calibration program that adjusts translation and rotation of each image until multi-wavelength emitting fluorescent beads and/or grids (Molecular Probes) are brought into alignment. Automated calibration routines are based on maximizing mutual information (MI; Viola and Wells, 1997; National Library of Medicine Insight toolkit). The MI approach appears to work very well for data having small errors in alignment. The inventors believe that the mutual information approach allows them to tweak the calibration using the fluorescence captured during sequencing itself, because the errors in alignment are small and develop slowly. Using the actual sequencing data for registration should eliminate the need for a separate calibration step (i.e., with beads), and thus allow constant updating during sequencing, but is not absolutely necessary.

Spot Identification

Fluorescence within the viewing field is continuously monitored by the CCD imager. The first step in the analysis is to identify sequencing complexes within the viewing volume of the imaging device. Computationally, this process must be highly efficient because it is carried out for each pixel or data element in the imager (i.e., millions of pixel positions). Once the sequencing complexes are found, more complex and time consuming analyses can be directed at this subset of pixel positions. The inventors have been successful using a simple averaging approach to identify potential sequencing complexes. By observing an image formed by averaging pixel intensity values over all the collected data frames or over a subset of the collected data frames, pixels localions that have fluorescence values greater than background fluorescent can be identified, particularly under conditions of static FRET. In situations where FRET is more dynamic, the inventors have found that this approach still works, but requires a running average over fewer frames.

Filtering/Denoising

The fluorescent signals are recorded by the CCD imager by counting the number of photons that arrive at a given pixel during a fixed integration time, an adjustable parameter of the imagining device. Estimating the fluorescent state of each fluorophore in a sequencing complex requires two interrelated processes. First the instantaneous fluorescence intensity emitted in each band of the spectrum, donor fluorescence and acceptor fluorescence, must be extracted from background noise. Second, the fluorescence state must be estimated using this multi-band information (see below). It is clear at this point that there is considerable variance in the fluorescence intensity both from the coming together of the sequencing reagents and from instrumentation noise such as laser intensity fluctuations and camera readout noise. The signals can be smoothed by standard techniques such as averaging, fast Fourier transform techniques, and wavelet techniques (Donoho and Johnstone, 1994; Cooley and Tukey, 1965; Frigo and Johnson, 1998). However, before rationally applying these techniques to yield an optimal signal that does not lose valuable information, the inventors have or are systematically characterizing the statistical properties of each of the noise sources. This characterization involves performing controlled experiments where each noise source, alone and in combination, is isolated as much as possible and characterized. These experiments are used to determine instrumentation noise, and characteristics of each of the fluorescent indicators. Next, controlled experiments are used to characterize dynamic spFRET. This data have been and is being used to classify FRET signatures for different event types such as true nucleotide incorporation event, mis-incorporation events, a nonproductive binding events, random collisions FRET events, etc. For example, to characterize signals due to a random collision of the labeled nucleotides, sample runs can be preformed in the absence of donors. To characterize mis-incorporation events, the inventors observe samples where only a mismatched base is available. To characterize nonproductive binding events, reactions are performed in conditions that incorporation cannot occur, e.g., in the presence of a 3' dideoxy-terminated primer. Other similar controlled reaction conditions can be used to characterize other event types.

Signal Estimation

Signal estimation is the process of assigning a fluorescent state to each of the molecules of interest. A molecule can be at the base state (non-emitting), the excited state (emitting), triplet blinking, or bleached. Additionally the molecule may be in FRET with another fluorophore, or in partial FRET, where it transfers energy to another molecule, but continues to emit light, but at a lower intentity level. In addition, certain fluorophores emit light in more than one band of the spectrum. Under some conditions where the signal-to-noise ratio is relatively high, this assignment is easily accomplished. However, in general, the ability to assign the correct state of each of the fluorophores at each time point in a trace ultimately determines the sensitivity of the system and will determine whether specific sequencing strategies are feasible. For example, FRET efficiency decreases rapidly with distance. The maximum usable distance is that in which the fluorescence of the acceptor molecule can still be distinguished reliably from background noise.

It is not necessary that this estimation function be fully distinct from the filtering functions described above. The inventors apply model-based estimation routines such as Kalman filtering, where each sequencing complex is considered to be in one of a series of internal states. A set of observables is defined (in this case fluorescence intensity of the various molecules). The observables are also analyzed for how their values vary as a function of the internal state and how their values are influenced, corrupted or degraded by various noise sources. The Kalman filter then produces a maximum likelihood estimate of the state of the model given the observables. This filtering represent a powerful approach, is well developed and has been applied to a variety of areas from satellite position detection to stock market prediction. Although the basic Kalman filter is limited in our application by a number of assumptions on linearity, extensions of this process such as extended Kalman filtering and particle filtering (Arulampalam et al., 2002) relax these assumptions (at the cost of additional computational requirements). The success of these algorithms for our purposes depends in large part on the ability to define statistics for different noise sources, and on available computational resources.

Base Assignment

Once the fluorescence states of the sequencing complexes have been assigned, the time-dependent changes in the states are then interpreted as or related to sequencing events occurring at the observed sequencing complexes. This interpretation depends on the specific configuration of reagents. For example, if an acceptor molecule on a labeled nucleotide travels into a FRET volume surrounding a donor, such as a donor-labeled enzyme, FRET may occur, where the FRET volume surrounding a donor is the volume in which a donor can transfer energy to an acceptor at a rate to be observed by the imagining system. Because of the nature of a FRET event, FRET events are characterized by a decrease in a donor fluorescent signal and a corresponding and simultaneous increase in an acceptor signal—the signals are anti-correlated. This time-dependent pattern of fluorescence at different wavelengths may represent or be interpreted as an incorporation event. If the fluorescence data are relatively clean, this step is very straightforward. One simply looks for specific patterns in the fluorescence signals. However, depending on the signal-to-noise ratio, it may be difficult or impossible to decide whether a specific set of changes in fluorescence is just noise. Thus, the inventors developed a set of criteria based on studying sequencing reactions subjected to a set of specific controls so that each assignment is accompanied by a numerical indicator of confidence. Such criteria includes the strength or clarity of the FRET signal, and the specific base being incorporated (characteristic patterns and/or lifetimes associated with fluorescence throughout incorporation).

DETAILED DESCRIPTION OF THE SIGNAL PROCESSING METHODOLOGY

Spot Find Process I

Figure 22:
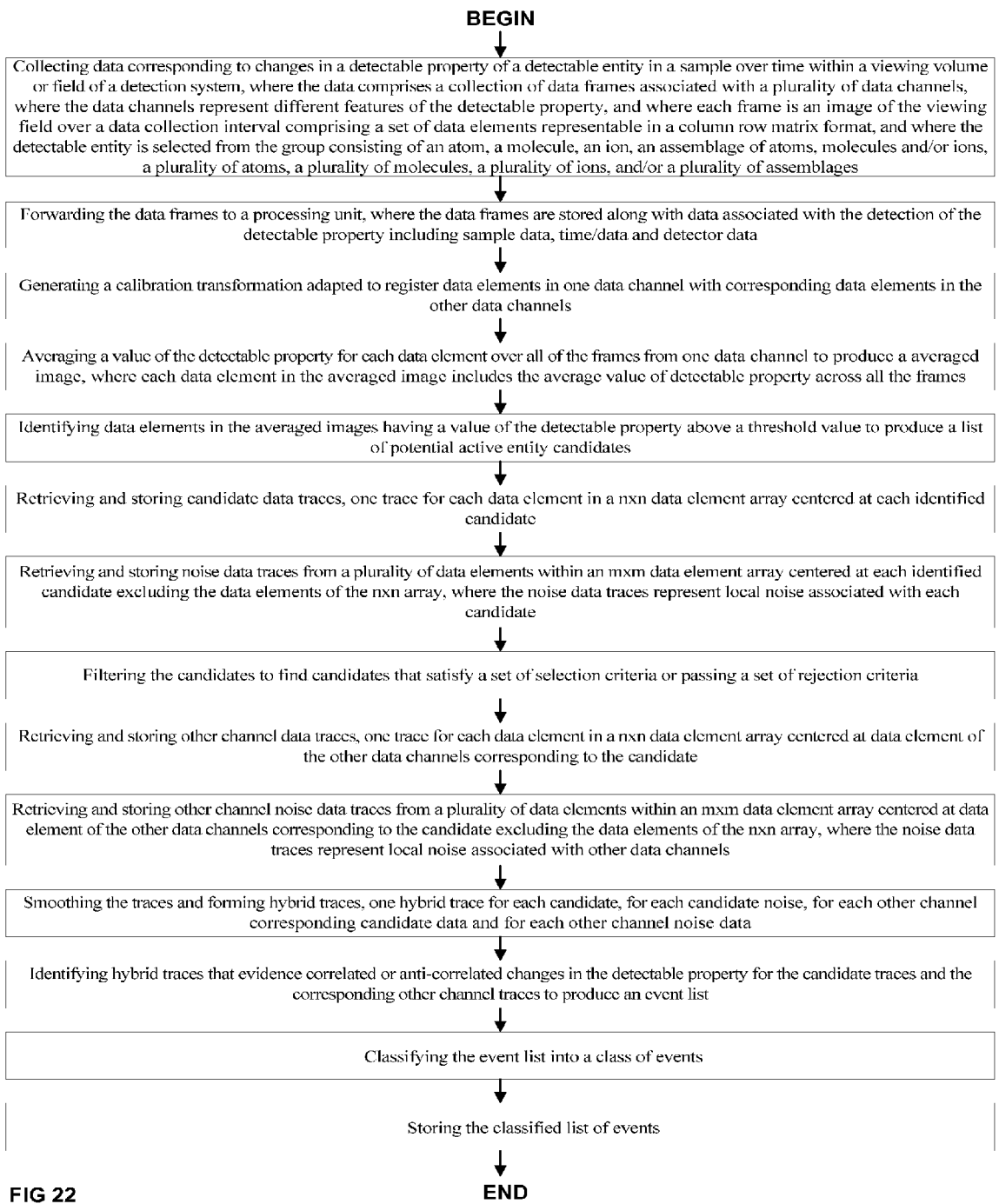
FIGS. 22-24 are flow diagrams that illustrate example signal processing methodologies for detecting and analyzing events at the single molecule level.
Figure 23:
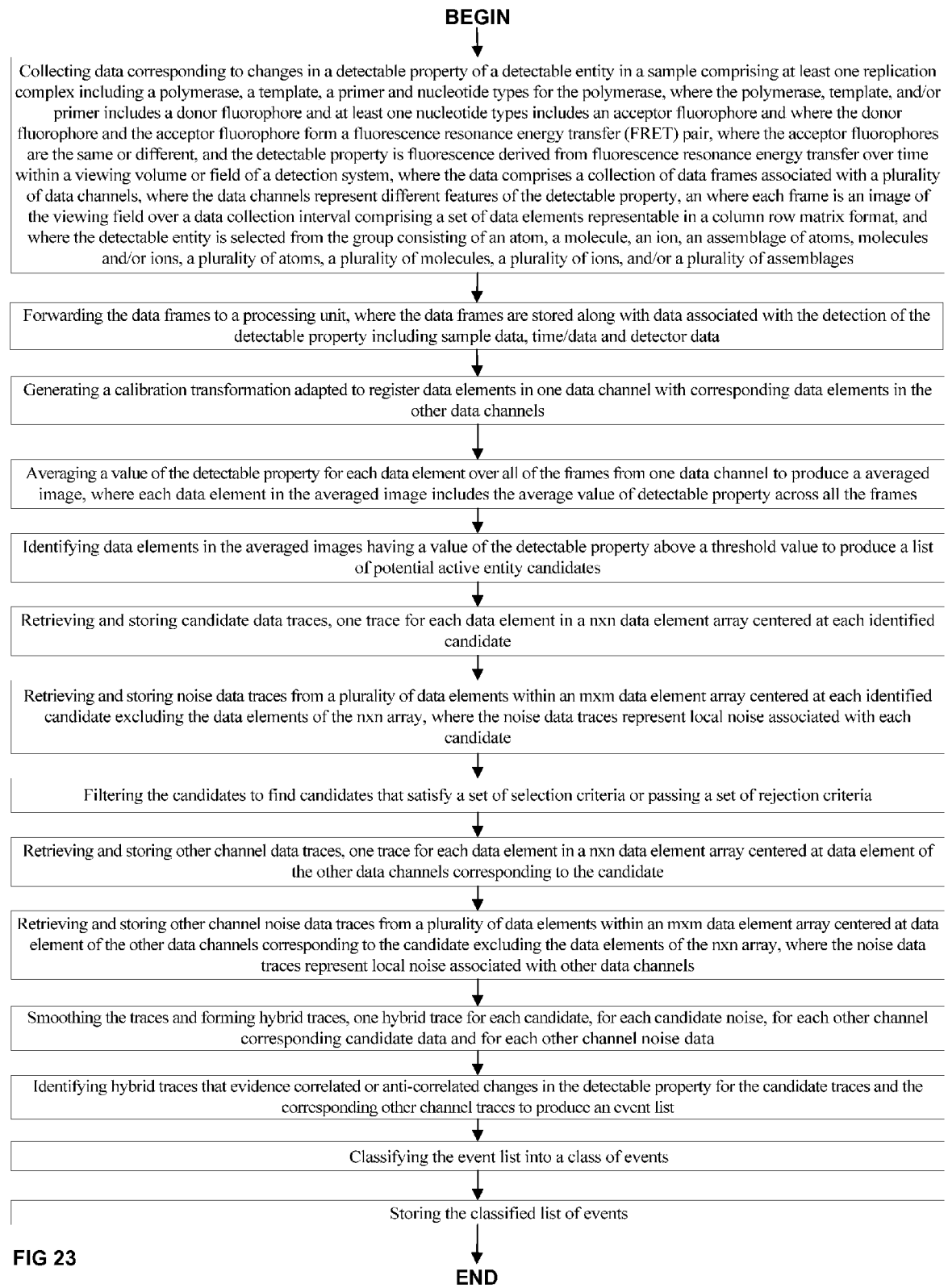
Figure 24:
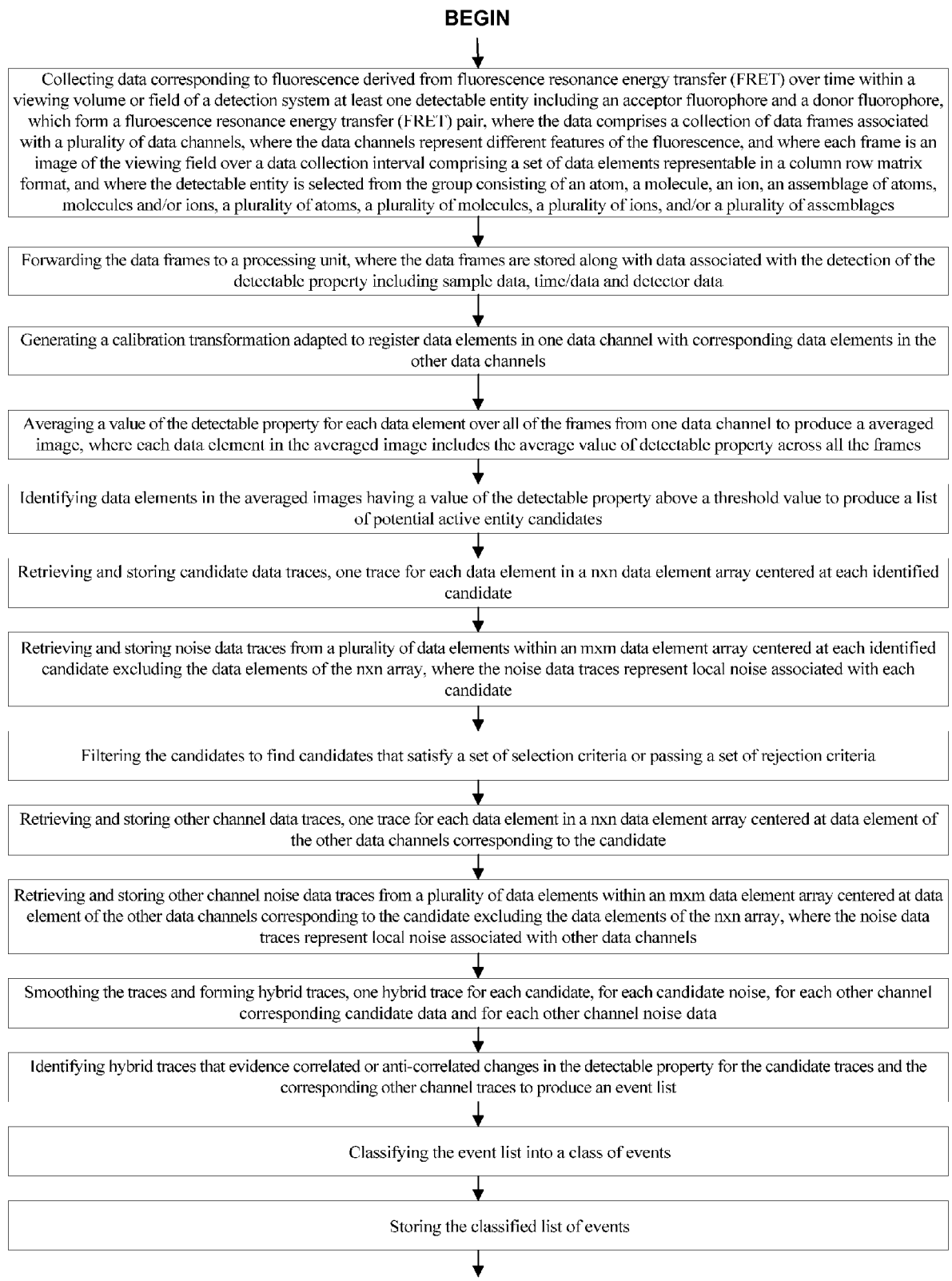

FIGS. 22-24 are flow diagrams that illustrate example signal processing methodologies for detecting and analyzing events at the single molecule level. The process starts by looking for pixels in the donor channel or quadrant that have a 'local maximum' donor intensity value in an averaged image, an image from averaging all or some of the frames in a stack for a given slide. For every value a of a pixel located at [col, row] in the image, the process determines whether the value a is greater than or equal to adjacent pixel values, and greater than 0.95 times diagonal neighbor pixel values. The condition 'greater than or equal to' is chosen to resolve the situation when two or more adjacent pixels have equal intensity, then the first one is picked as a candidate.

If the above conditions are met, the pixel at [col,row] is taken as a spot candidate. Because the number of candidates can be huge (typically around 3000 on an 360×360 overlay), several filters are applied to limit the number of spot candidates that are passed on for subsequent processing.

Figure 2:
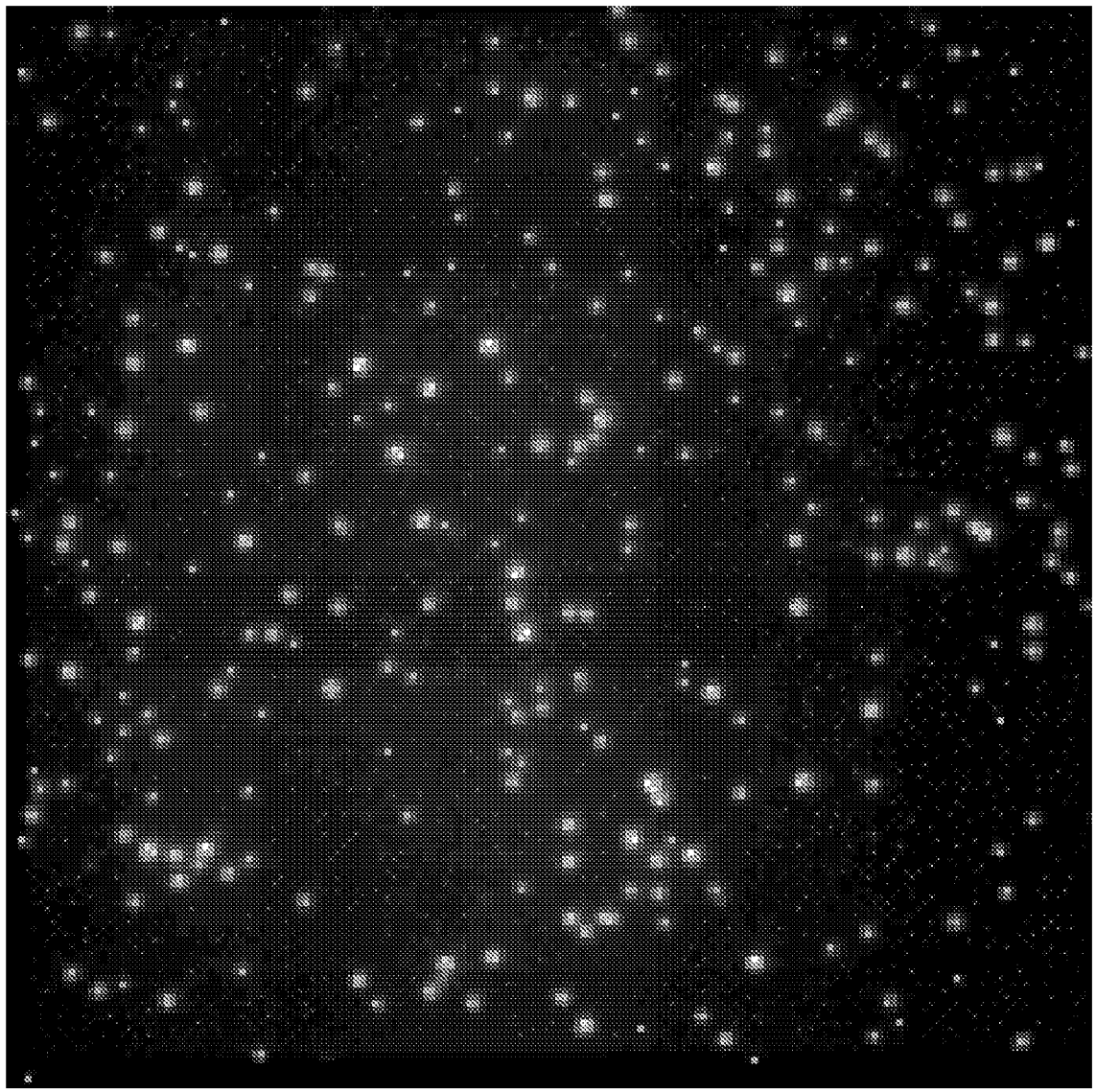
FIG. 2 depicts spot candidates displayed on an overlay picture of the viewing filed, where the accepted candidates are shown as large dots sometimes with gray boxes (green in a color image) and the very faint dots represent candidates rejected by staged filtering (in a color image, blue spots are candidates eliminated by the stage 1 filter and red dots are candidates rejected by the stage 2 and 3 filters).
Figure 2:
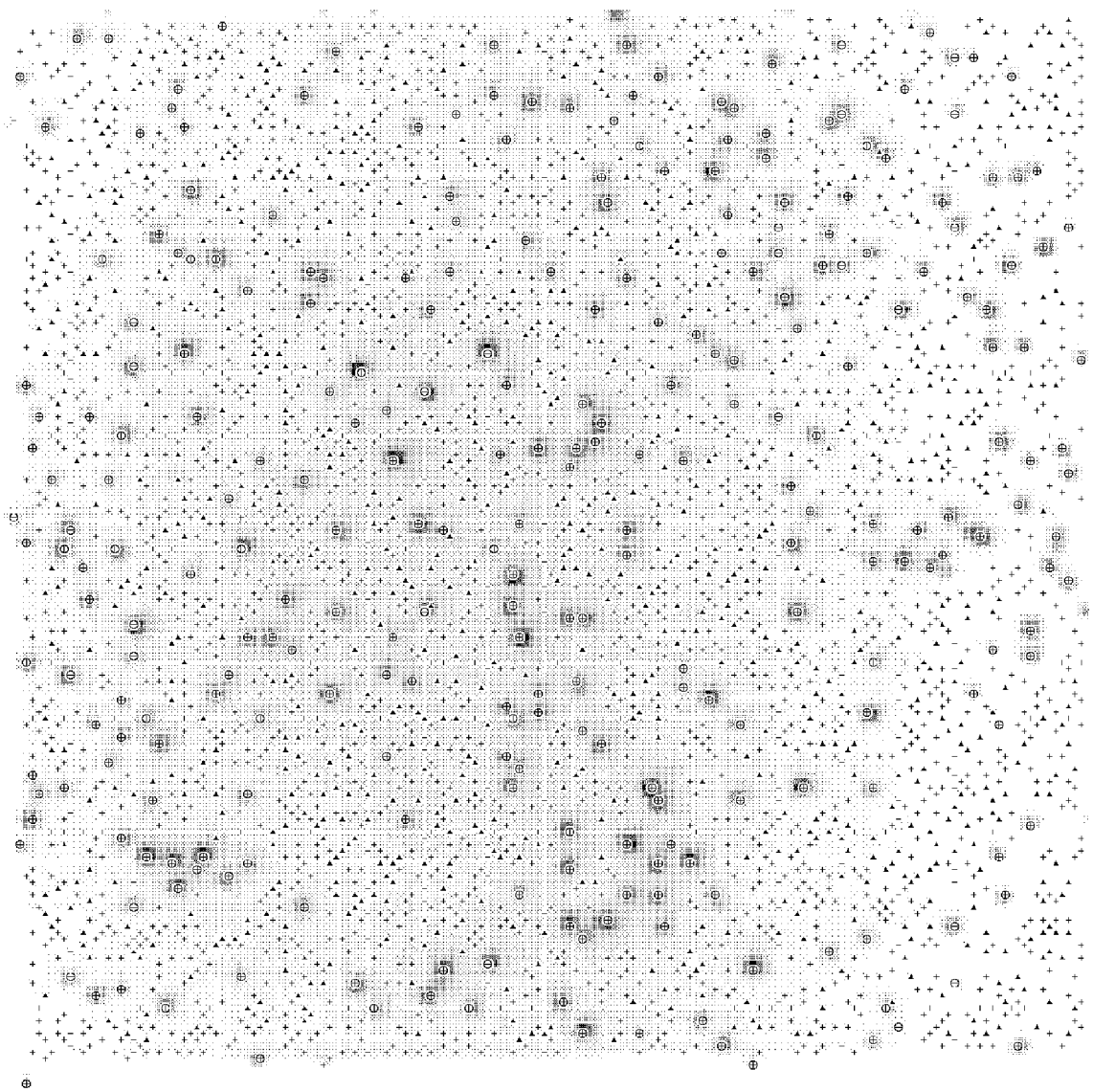

Referring now to FIGS. 2 and 2', spot candidates on an overlay image are shown as large and small dots (large dotes are green and small dots are blue and red in a color image). The small dots represent candidates rejected by the stage 1 filter and by the stage 2 and 3 filters (blue and red, respectively).

Stage 1 Filter

The stage 1 filter estimates background noise level around each candidate pixel, then compares it to the pixel value a. The stage 1 filter determines these levels by selects 15 least bright pixels in a 5×5 area [col−2,row−2 . . . col+2,row+2] and computes a mean c and a standard deviation na of their intensity distribution. The signal to noise ratio (a-c)/na is a measure of how much a candidate pixel intensity value is above local background noise. If this ratio is less than a signal-to-noise threshold value, then the candidate is rejected. The signal-tonoise threshold value is generally between about 1.5 and about 5. In certain embodiments, the signal-to-noise threshold value is 3.

Figure 3A:
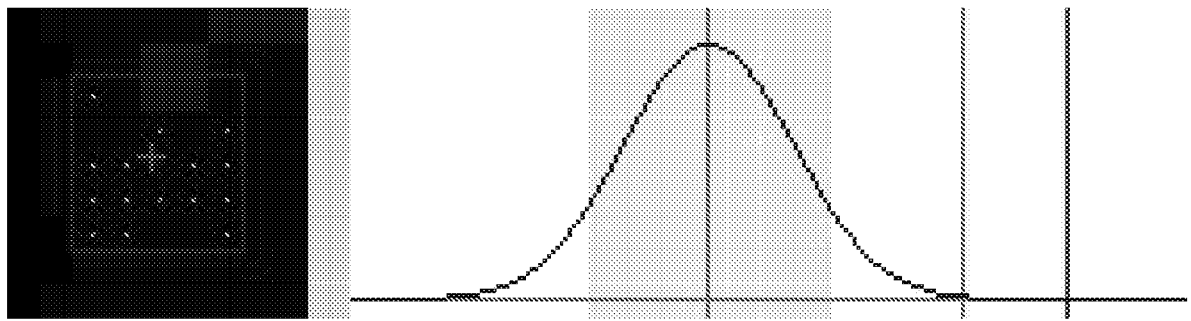
FIG. 3a depicts the intensity of the candidate pixel is below 3·na, the candidate is rejected.
Figure 3A:
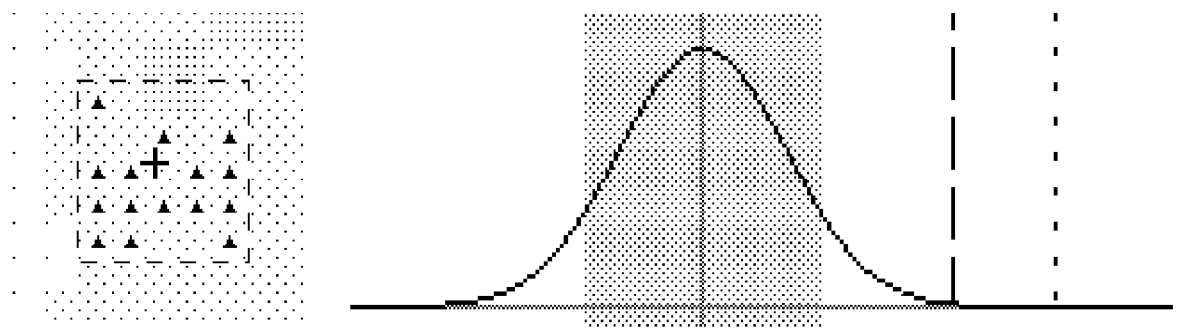
Figure 3B:
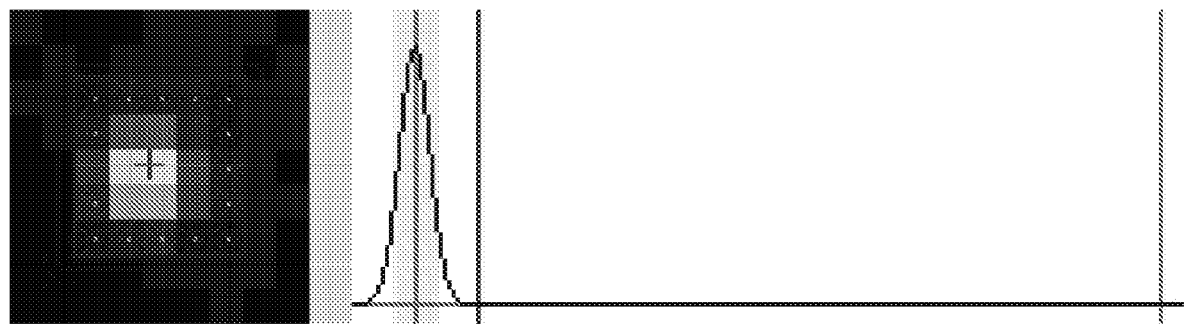
FIG. 3b depicts the intensity of the candidate pixel is equal to or above 3.na, the candidate is accepted.
Figure 3B:
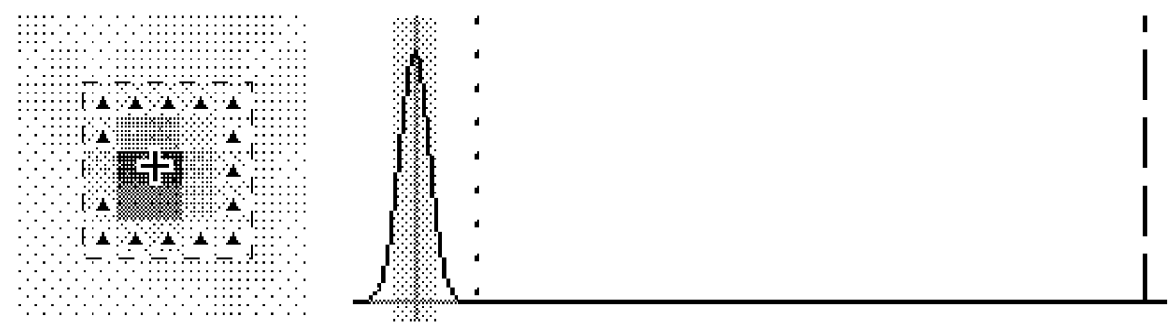

Refening now to FIGS. 3a&b and 3a'&b', the methodology for candidate pixel rejection and acceptance is shown. Looking at FIGS. 3a and 3a', candidate rejection is shown, where pixel candidates are rejected if their intensity values are below (less than) the signal-to-noise threshold value of 3 or equivalently, where the intensity a is below (less than) 3 na. Looking at FIGS. 3b and 3b', candidate acceptance is shown, where pixel candidates are accepted if their intensity values are greater than or equal to the signal-to-noise threshold value of 3 or equivalently where the intensity a is greater than or equal to 3 na.

In the figures, across (red in a color image) marks the candidate pixel in the left hand portion of the averaged image. A gray square (blue in a color image) surrounds that candidate pixel and is a 5×5 surrounding pixel area. 15 least bright pixels within the 5×5 surrounding pixel area are marked with dots (green in a color image).

The graph on the right in the figures plots the intensity distribution of the 15 selected pixels represented by the dots inside the square. A gray area in the plot shows the standard deviation of the background noise level. A black vertical line marks the mean value c of the distribution. A dark grey vertical line (red in a color image) is 3 times standard deviation na (same as the threshold signal to noise ratio) away from the mean. A light grey vertical line (green in a color image) is the intensity value a of the candidate pixel. If the light gray (green) line is to the left of the dark gray (red) line, the candidate is filtered out.

This filter typically eliminates about ⅔ of the pixel candidates, leaving about 1000 out of ~3000 spot candidates. The inventors have found that about ¾ of the remaining candidates also do not represent a true candidate. Thus, this stage 1 filter is not real efficient at candidate elimination. The principal reason for the stage 1 filters lack of robustness is that it uses a local noise level, computed on statistically insufficient data. Referring now to FIGS. 4 and 4', an example of a "poor" spot candidate that passed through the stage 1 filter is shown.

Stage 2 Filter

The stage 2 filter was designed to compensate for the lack of robustness of the stage 1 filter. The stage 2 filter works in a very similar way from the stage 1 filter. The stage 2 filter uses a global noise level, which is an average avgna of the local noise levels na of all spot candidates from the previous step.

Note that the global noise level cannot be easily obtained by just computing statistical parameters of low-intensity pixels from the entire overlay area, because the mean of their distribution is not constant, it slowly changes across the quadrant. However, an average of local noise levels around the spot candidates gives a fair approximation to the global noise level (average deviations from variable local pixel intensity means).

Referring to FIGS. 5 and 5', the stage 2 filter is illustrated graphically. The graph shows a horizontal slice of the overlay area around the candidate pixel shown in FIGS. 3a-3b and 3a'-3b'. The dark grey (green in a color image) bars represent pixel intensity values around and including the candidate pixel, which is the middle bar. A black horizontal line marks a local 'zero' level, the mean c of the intensity distribution of low-intensity pixels, which passes through most of the bars. The gray area with the black horizontal line centered in the middle represents the global noise level avgna, an avarage of standard deviations na derived from all the spot candidates as explained above. A bell curve (green in a color image) represents an estimated intensity model of the spot candidate, having its maximum at the brighiest (middle) pixel. The maximum is also shown as a horizontal (green in a color image) line touching the top of the bell curve.

A dark (red in color image) line represents a level of minc times avgna, where minc is a parameter having value between about 3 and about 12. In certain embodiments, the parameter is 7. A light gray (brown in color image) line represents a level of doubt times avgna, where doubt is a parameter having value between about 5 and about 20. In certain embodiments, the parameter is 12. The signal to noise (SN) ratio is re-computed for every spot candidate as (a-c)lavgna. If the candidate SN ratio is below (less than) the value of minc, the candidate is rejected. If the candidate SN ratio is greater than or equal to the value of doubt, the candidate is accepted with no further checking. If the candidate SN ratio is in between the value of minc and doubt, which typically happens in approximately 50 to 100 cases, the candidate is passed onto the stage 3 filter.

The stage 2 filter effectively eliminates almost all candidate pixels found by the inventors to not represent spots for further analysis, leaving only good spots (typically, ~250 out of ~1000) with a relatively small amount of doubtful spot candidates.

Stage 3 Filter

The stage 3 filter is applied only to the doubtful spot candidates from the stage 2 filter. The stage 3 filter starts by computing a more precise spot model by best-fitting spot pixel intensities in the 5×5 area [col−2,row−2 ... col+2,row+2] according to the formula:

$$I(\text{col},\text{row}) = C + A \cdot \exp(-((\text{col}-Xm)^2 + (\text{row}-Ym)^2)/R^2)$$

where C, A, Xm, Ym, and R are computed as to satisfy least squares condition. The adjusted signal to noise ratio Alavgna is then compared to the value of a parameter minc2 (ranging from about 5 to about 12, and in certain embodiments having the value 9). If the adjusted signal to noise ratio Alavgna is below (less than) minc2, then the doubtful spot candidate is finally rejected.

Figure 6A:
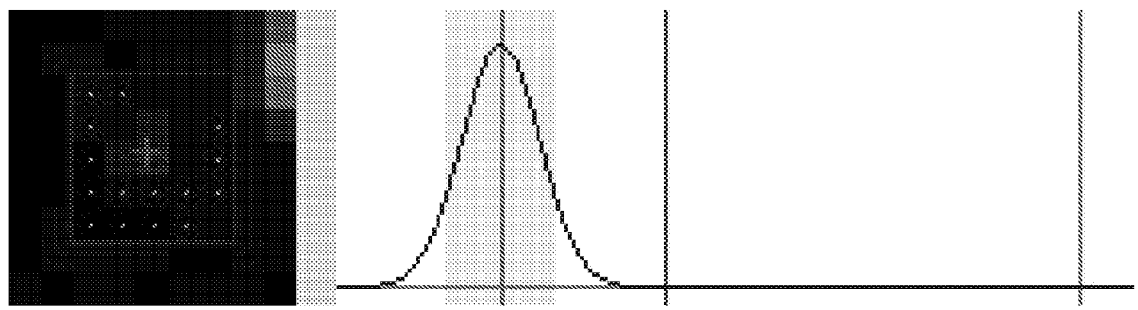
FIG. 6a depicts graphically the spot candidate filtering process of the stage 1 filter.
Figure 6A:
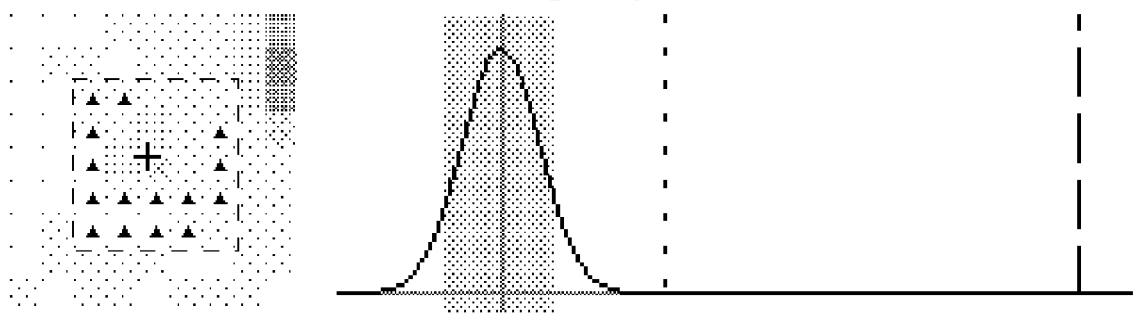
Figure 6B:
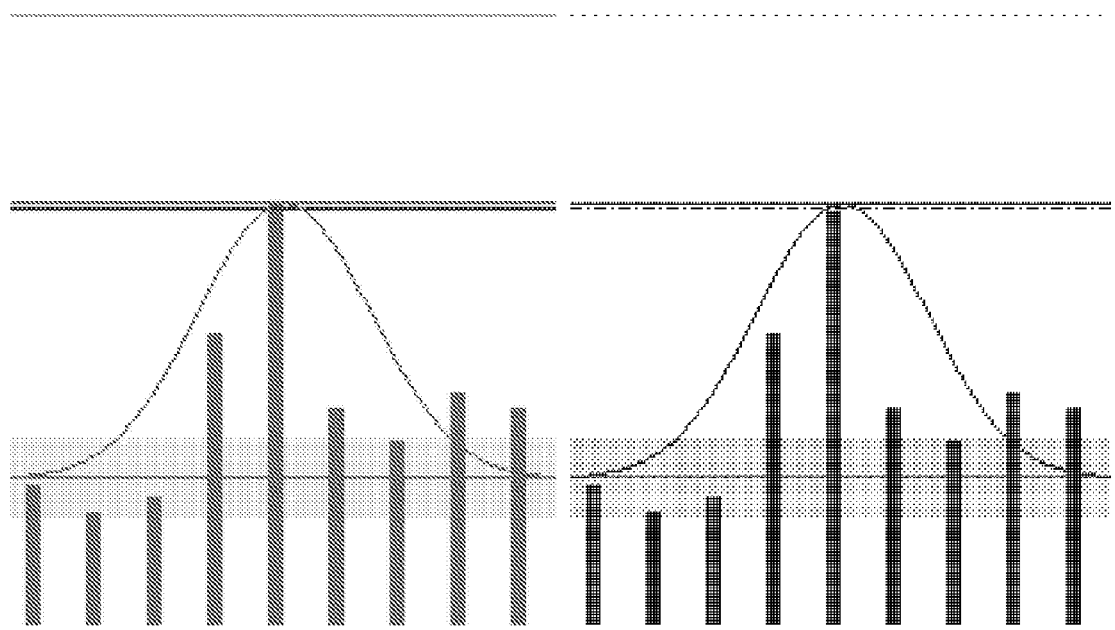
FIG. 6b depicts graphically the spot candidate filtering process of the stage 2 filter.

Referring now to FIGS. 6a-c and 6a'-c', the stage 3 filter is depicted graphically. Looking as FIGS. 6a and 6a', a spot candidate that passed through the stage 1 filter is shown, while looking at FIGS. 6b and 6b', a spot candidate that passed through the stage 2 filter is shown. Looking at FIGS. 6c and 6c', the best-fitted pixel intensity model is shown as a bell curve (blue in a color image) used in a stage 3 filter rejection. A curve horizontal line (green line in a color image) represents a maximum intensity of the model; the line contacts a top of the bell curve. A dark (red) horizontal line represent the level of minc2 times avgna. If the curve horizontal line is below the dark minc2 times avgna line, the spot candidate is finally rejected. The stage 3 filter typically eliminates 10 to 20 percent of the doubtful spot candidates.

The remaining spot candidate objects are stored in an array and returned to the caller. They are shown as green dots on the FIGS. 2 and 2'.

Average Stack Over Different Intervals

In some cases, potential donor candidates are not identified due to averaging over too large of a set of frames in a stack. This missing of potential donor is especially apparent when averaging is performed on an average including all frames of a stack. The potential reasons for missing acceptable candidates is that certain active sequencing complexes may not have donor that have detectable lifetimes that span all of frames or a significant amount of the total frames to be selected in an averaging over too large a frame set. Thus, these potential donor candidates generally have shorter lifetimes, and the average donor intensity is consequently too low for the site to be selected as a donor candidate.

Dynamic Binning

To address this problem, a dynamic binning process (adjusting the number of frames to average over) was implemented to determine whether the process changed the number of donor candidates. The user enters the number of the bins as a parameter, e.g., 1, 2, 4, 8 and 10 as number of bins. The parameter is modifiable based on the observed experimental donor lifetimes results. After implementing the dynamic binning in candidate identification, the inventors found an increase in the number of the donor candidates. The inventors also found that the number of candidates increased with decreasing binning number.

Consolidation of Donors

Figure 7A:
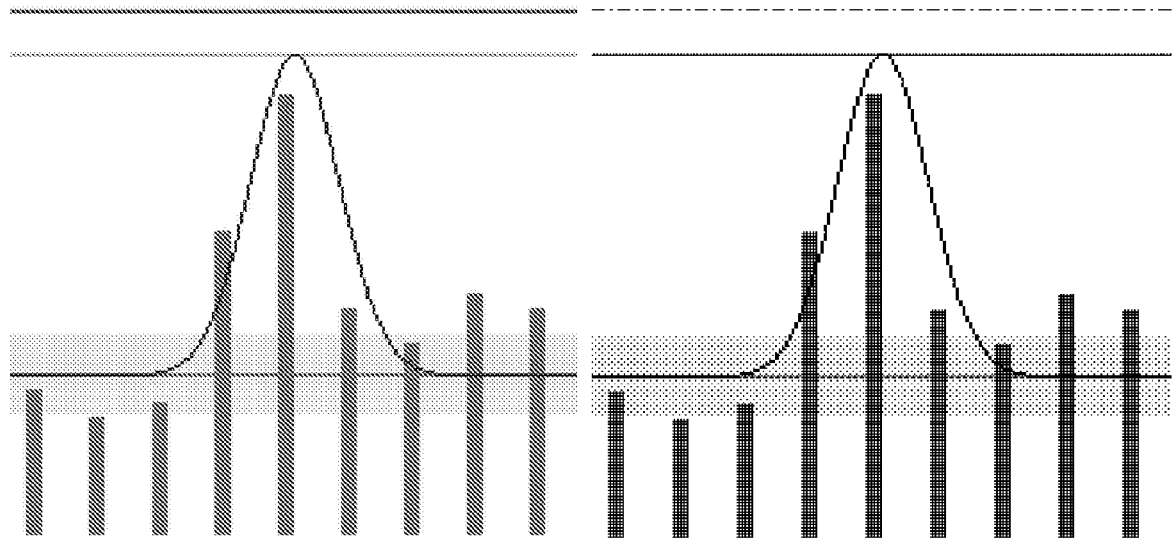
FIG. 7a depicts pixel values (9×9 neighborhood) after voting over average donor image.

Once the stack image is averaged over various intervals, the process generates multiple average images requiring consolidation of the donor spots. For each averaged image, the spot find process I is applied to identify initial spots. After the spot identification, the process performs voting of the donor spots. Voting involves adding the binary value associated with each spot across the averaged images and that value is stored the new master image. For example, if the stack include 1000 flames, which were imaged in 250 frame bins, then the voting would have a maximum value of 4 for each spot and an minimum value of 1. FIG. 7a depicts pixel values after voting over average donor images.

Figures 7B, 7C:
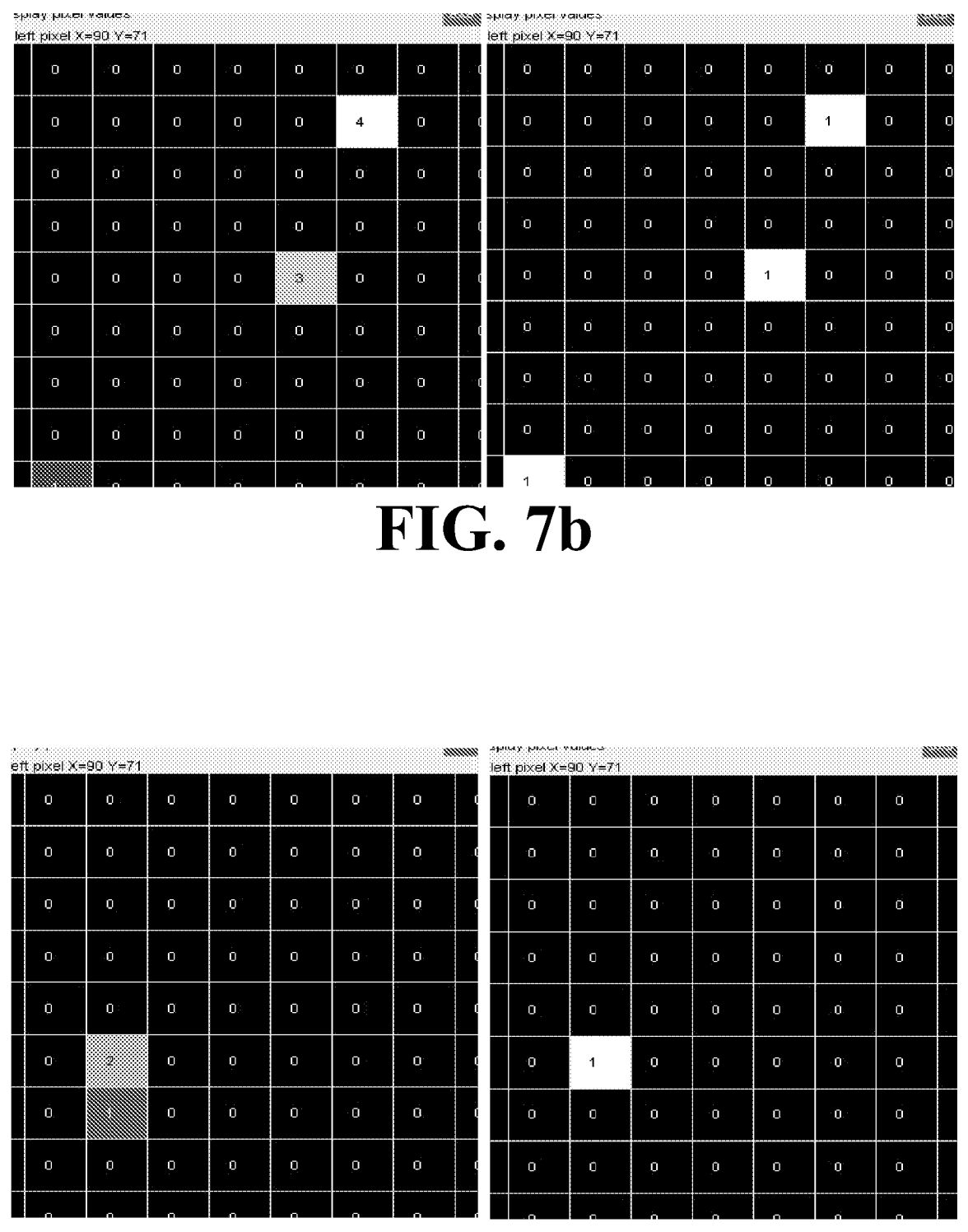

After the voting operation, we use a neighborhood criterion to obtain a consolidated donor image. All pixels which have a value greater or equal to 1 are considered donor candidates. In the consolidated donor image, first the spots with highest votes are selected, with consecutive selections proceeding on decreasing vote values. Any donor candidate within the 3×3 neighborhood of a previouslyselected candidate is rejected. This is a recursive operation performed until all pixels with votes greater than or equal to 1 (donor candidates) have been considered. In the case of a tie in vote value, the pixel with higher intensity is selected as a donor spot The process identifies both single spots and grouped spots. Only the grouped spots undergo the consolidation operation. FIG. 7b depicts single spot selection in an average donor image after voting, while FIG. 7c depicts a snapshot of grouped spots after voting and selection of the donor pixel.

Figure 8:
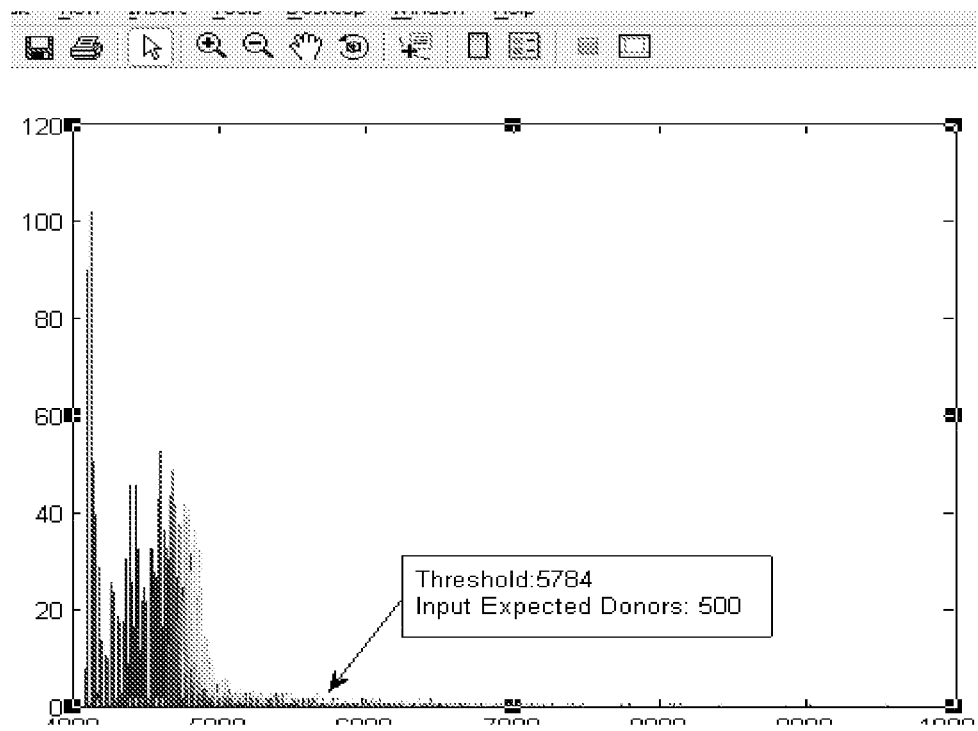
FIG. 8 depicts histogram of an average intensity stack image.

Dynamnic thresholding is an alternate process for identifying or find spots (pixels location for which fluorescence is above background and may represent active sequencing complexes). The pre-selection stage ofthe selection of donor candidates sometimes overestimates the donors and can be seen as redundant. Alternatively to stage 1 filtering, initial donor candidates can be estimated by computing a dynamic threshold. The user can enter expected donors (default is set to an experimental obtained value). Using histogram analysis, the brightest spots on the image are selected using intensity information as shown in FIG. 8. An accurate threshold value is generally determined from the intensity data alone, but can also be based on intensity and lifetime data.

Figure 9:
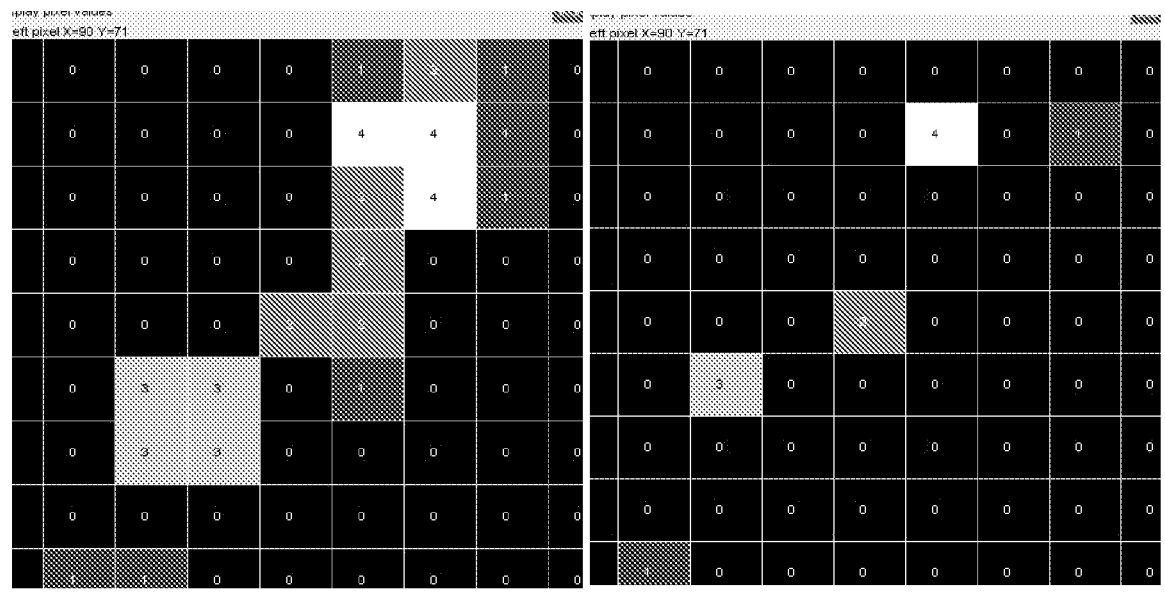
FIG. 9 depicts donors detected using dynamic threshold and consolidated donors.
Figure 10A:
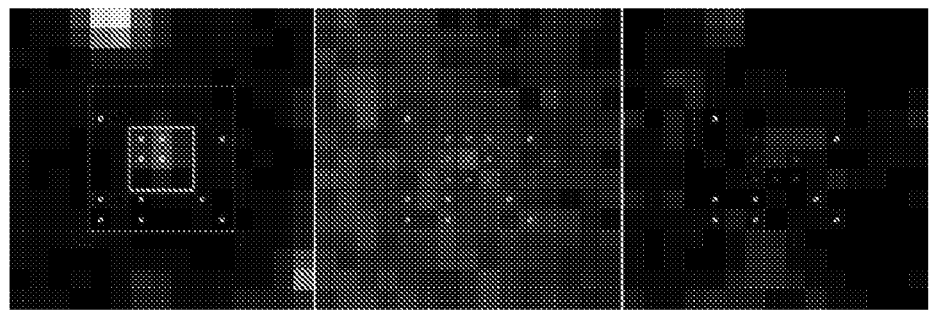
FIG. 10a depicts the noise pixel traces are averaged into a single averaged noise trace (top graph), then its polynomial approximation is computed using least squares algorithm, and finally, the value of the polynomial is subtracted from every individual pixel trace.
Figure 10A:
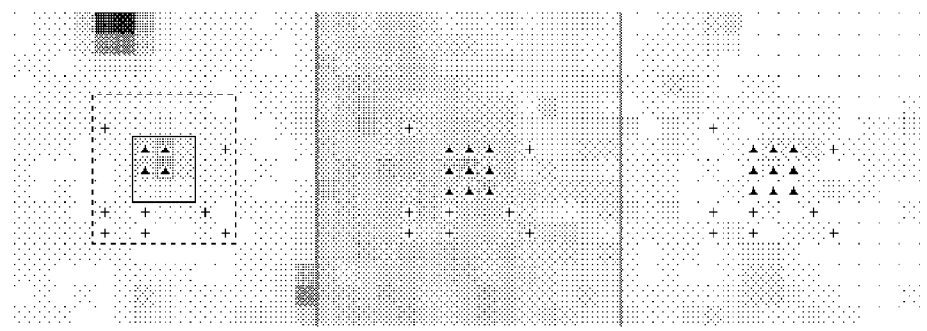
Figure 10B:
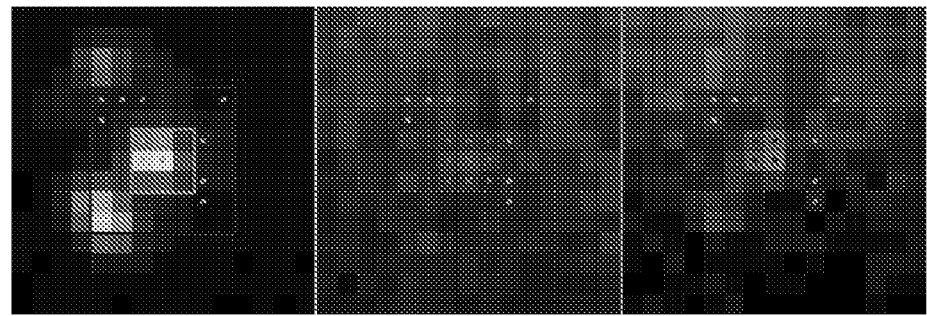
FIG. 10b depicts the value of the approximating polynomial is subtracted from donor signal pixels (above graph), the result is shown on the below graph—the horizontal line now represents the zero-level (mean of the background noise intensity distribution).
Figure 10B:
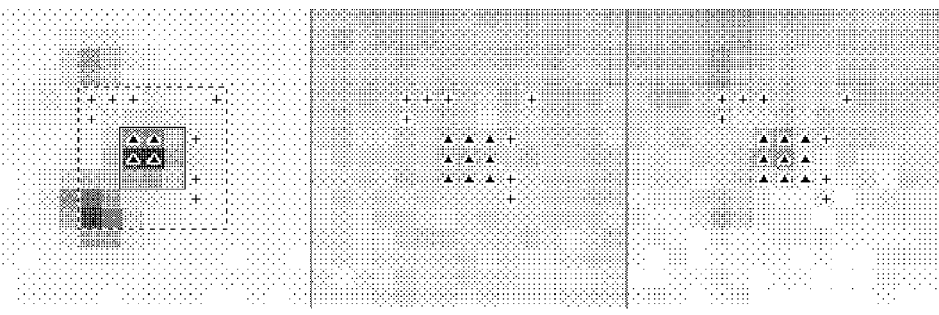
Figure 10C:
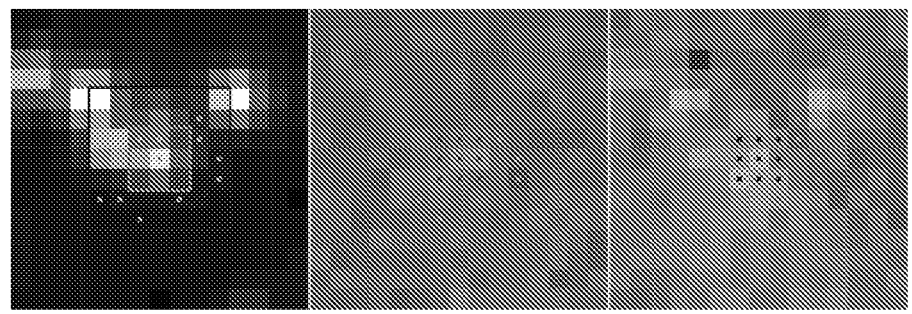
FIG. 10c depicts the noise pixel traces from an acceptor channel are averaged into a single averaged noise trace (top graph), then its polynomial approximation is subtracted from every individual acceptor pixel trace.
Figure 10C:
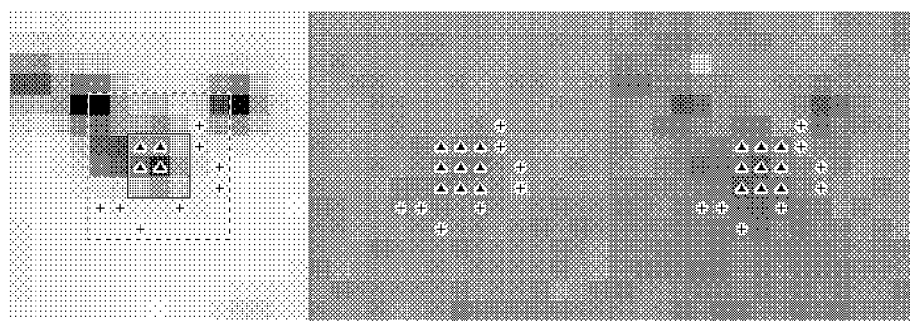
Figure 10D:
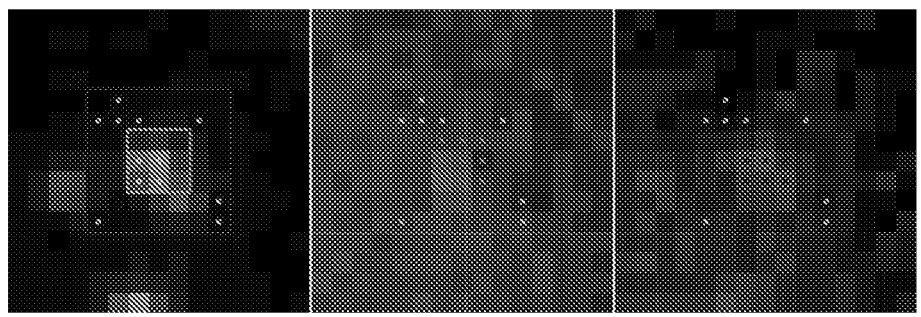
FIG. 10d depicts the value of the approximating polynomial is subtracted from acceptor signal pixels (above graph), the result is shown on the below graph—the horizontal line now represents the zero-level (mean of the background noise intensity distribution).
Figure 10D:
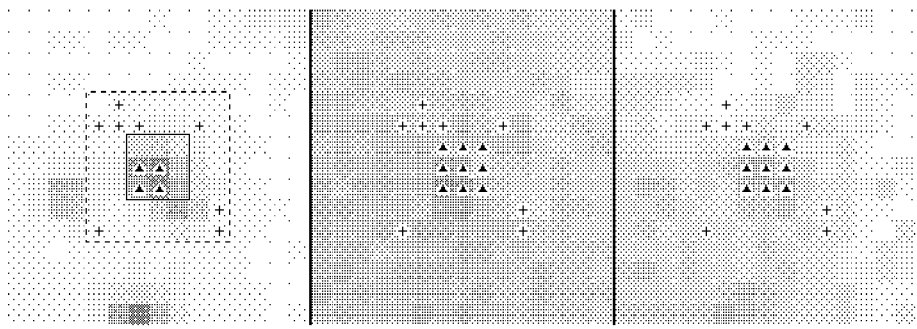
Figure 11A:
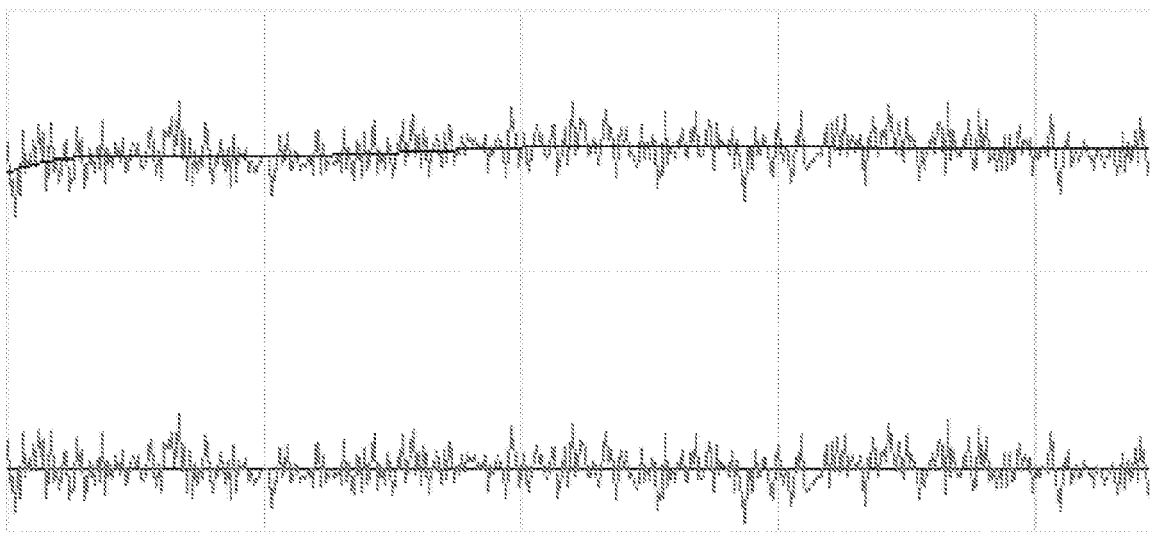
FIGS. 11a-11d depicts donor pixel selection.
Figure 11A:
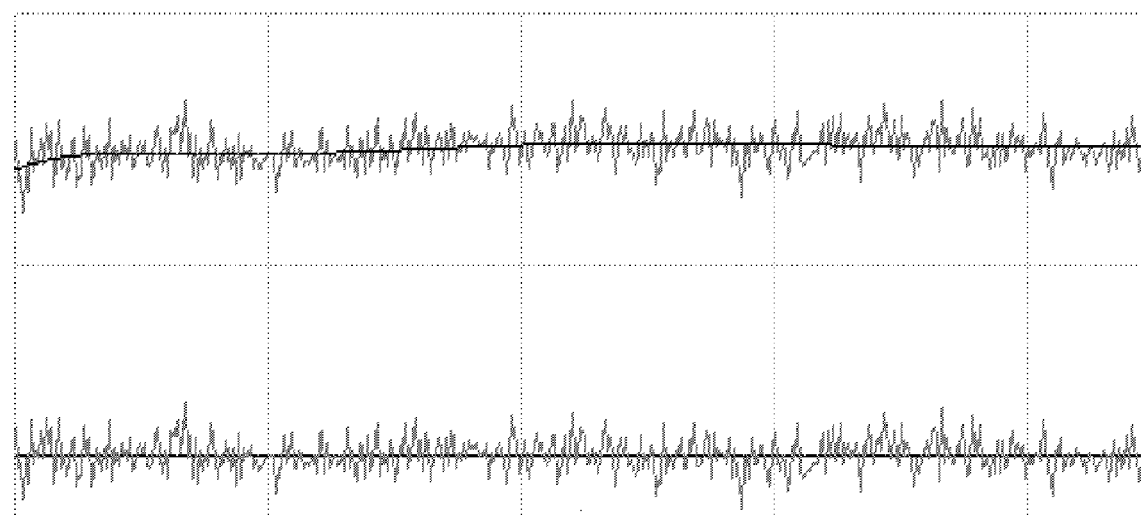
Figure 11B:
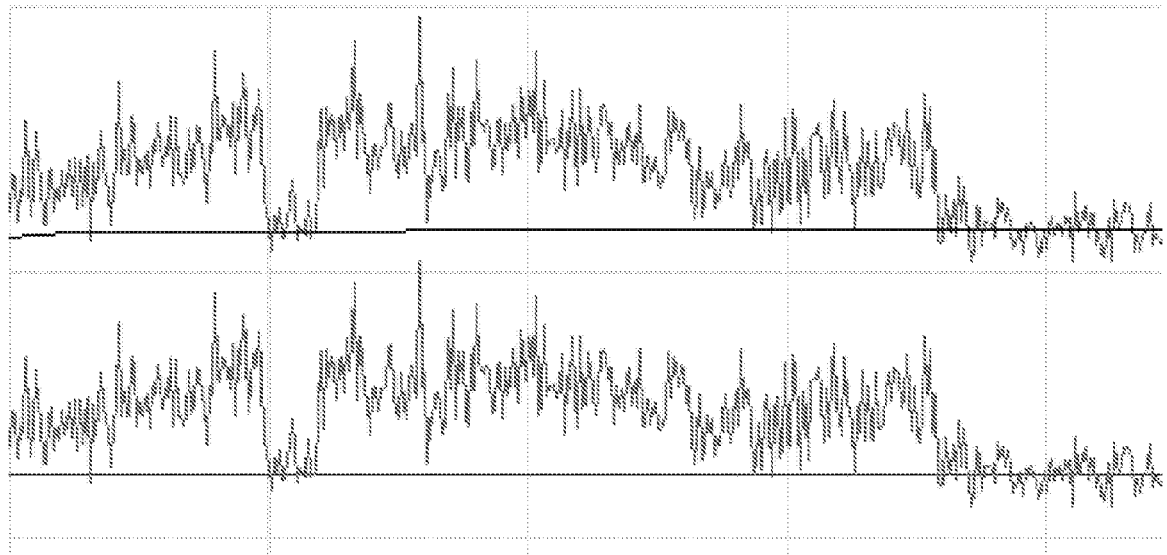
Figure 11B:
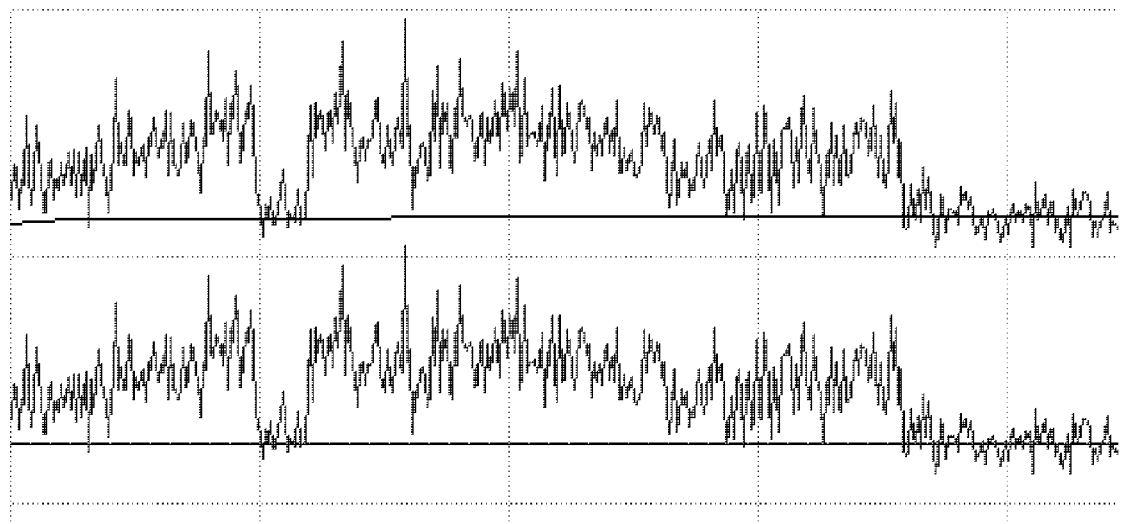
Figure 11C:
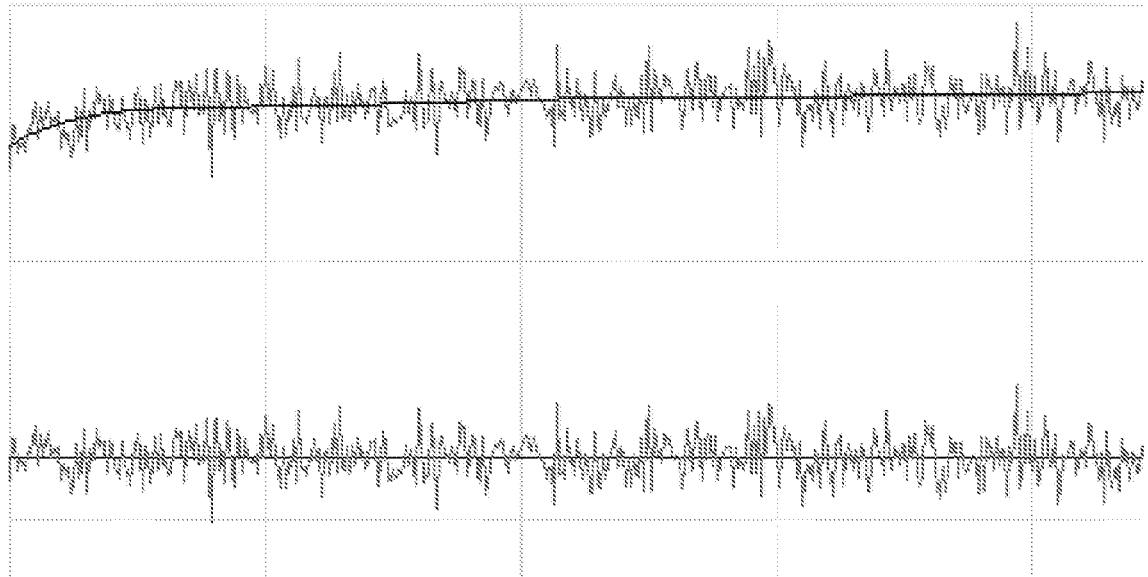
Figure 11C:
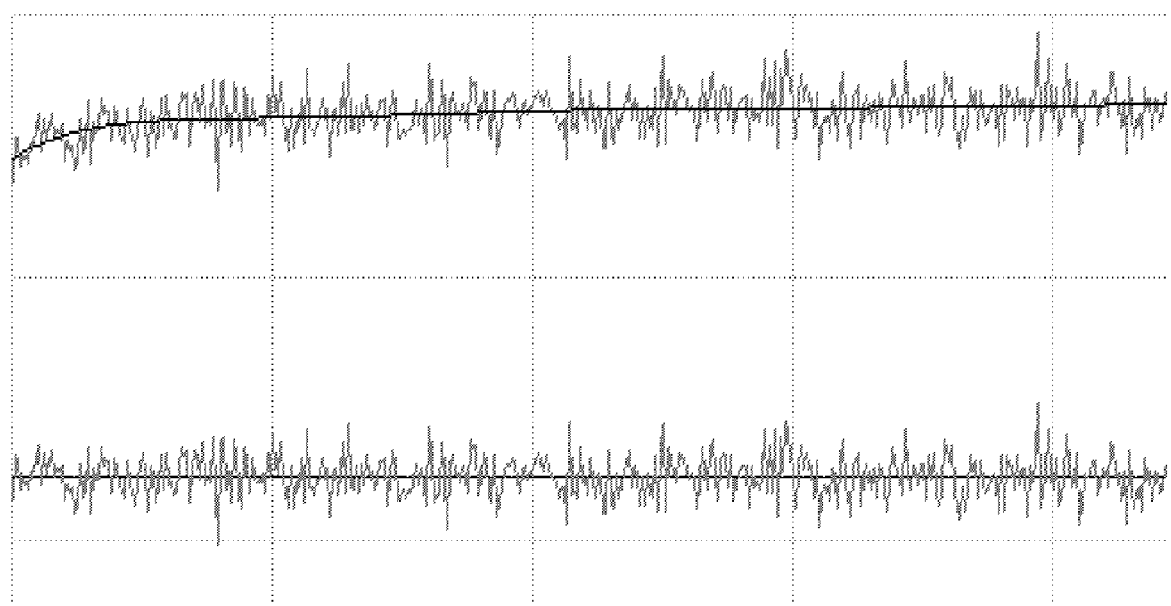
Figure 11D:
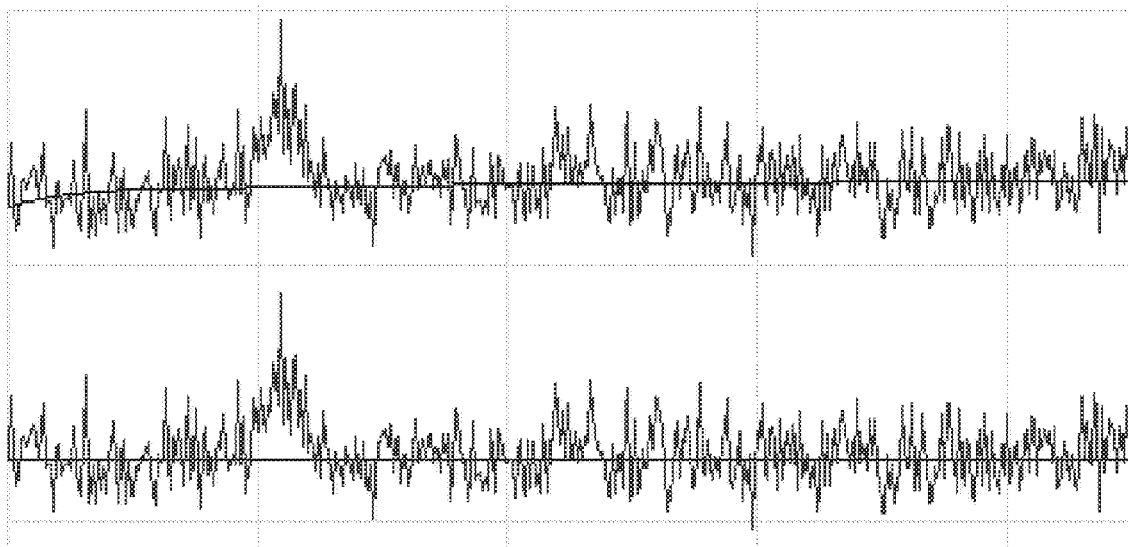
Figure 11D:
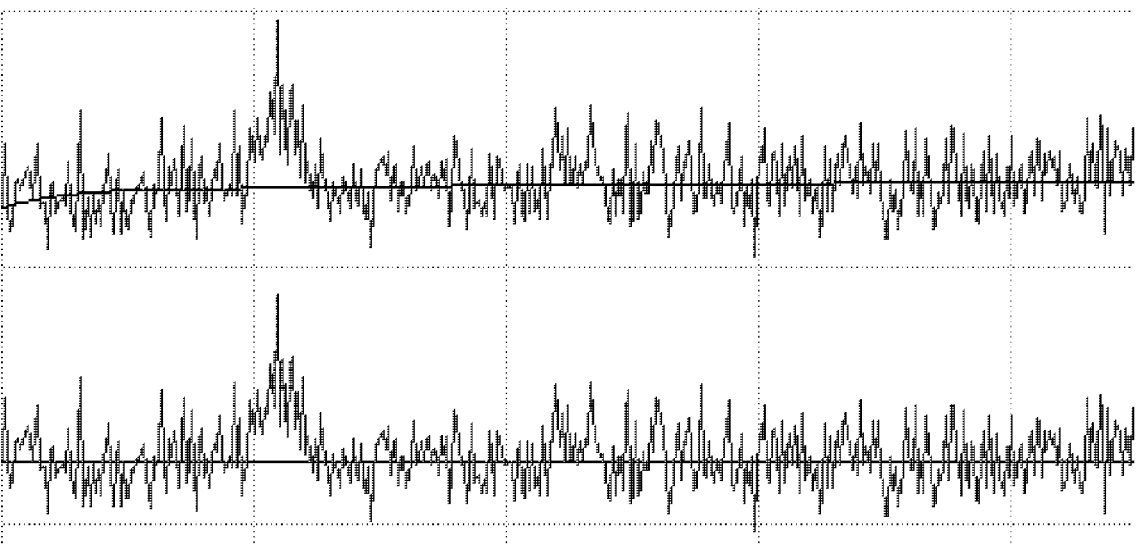

Thresholding is a global operation and may result in donor candidates that are actually with the closed 3×3 neighborhood of a previously identified donor candidate. The candidate identification process keeps track of single spots and grouped stops or clusters, by using morphological operations (single pixels in the 3×3 neighborhood matrix are separated from grouped pixels): FIG. 7b and FIG. 7c depict single spots and group spots identified after voting and selected donor pixels after confsolidation. To determine which pixels are real donors in a cluster, the process uses an approach similar to the approach used for consolidation of donors as described before, where the process analyzed the distance (3×3 neighborhood information) between candidates, votes and intensity information. Referring to FIG. 9, the thresholding gives rise to several instances of a donor candidate within the 3×3 neighborhood of another donor candidate. These occurrences are resolved into real donor candidates using vote and intensity information as discriminators.

Initial Pixel Selection

For every spot (donor) at [col,row], the process selects nine brightest pixels for the donor signal and up to eight pixels around the nine brightest pixels as donor noise data. At first, the process sorts pixels in a 7×7 area [col−3,row−3 . . . col+3,row+3] surrounding a spot by decreasing intensity. Then, the process selects nine (9) pixels in a 3×3 array or area [col−1,row−1 . . . col+1,row+1] with the candidate pixel in the middle of the 3×3 area. After that, the process randomly selects up eight (8) pixels having the lowest intensity from the set of pixels outside of the 3×3 array or in the second part of the 7×7 area as noise pixels for each 3×3 array including a bright pixel. Again, the method was tuned used 3×3 and 7×7, but the method can equally well work with larger and smaller arrays, n×n and m×m array where m and n are integers and m>n, with the array size being a function of the detection system and the system being detected.

Next, the donor quadrant coordinates [col,row] are transformed into acceptor quadrant coordinates [colA,rowA] by applying the coordinate transform obtained from the calibration data. That is, the data in the acceptor channels are transformed by the calibration transform so that locations in the acceptor channels correspond to location is the donor channel. Then, the nine (9) pixels in a 3×3 area or array including a pixel location [colA,rowA] in the acceptor channel corresponding to each of the selected donor pixel location [col, row] are selected as candidates from acceptor channel. Because at this stage of the analysis, there is no way to a prior discriminate between good and poor acceptor pixels, all nine pixels are selected in the 3×3 array including a donor corresponding acceptor pixel. The coordinates of acceptor noise pixels are obtained by applying the coordinate transform to donor noise pixels.

Referring now to FIGS. 10a-10d and 10a'-10d', four examples of the initial pixel selection methodology are depicted graphically. In the left most images, an inner square (green in a color image) delimits the 3×3 area [col−1, row−1 . . . col+1, row+1] from which the 9 donor signal pixels are selected. An outer square (blue in a color image) delimits the 7×7 area [col−3,row−3 . . . col+3,row+3] from which the 8 donor noise pixels are selected shown as gray dots (cyan dots in a color image). In the middle images, dark dots (red in a color image) represent the 9 selected acceptor pixels in acceptor channel 1 and gray dots represent the 8 selected acceptor 1 noise. In the right images, the dark dots (blue in a color image) represent the 9 selected acceptor pixels in acceptor channel 2 and gray dots represent the 8 selected acceptor 2 noise. The exact location of the acceptor pixels are determined by the application of the calibration transformation derived calibration routines.

After all relevant pixel coordinates for all candidates spots have been identified and selected, the process reads the stack file again, frame by frame, and collects individual pixel traces, i.e., data associated with a given pixel location in each frame through all the frames in the entire stack or that portion of the stack that includes potentially relevant sequencing data.

Thus, if the above analysis was directed to whole stack averages, then the candidates would represent pixels that have values above a threshold. If the above analysis was directed to partial stack averages, then the candidates would represent pixels that have values above a threshold as well, but the average would be over less than all the frames. Again, if binning is used, then the candidates signals may extend from one bin to the next bin so the trace would extend until the relevant data is collected into the trace.

Hi-pass Filter

Every signal trace can be considered as a useful signal to which an amount of random (chaotic) noise is added. The zero-point of the signal intensity can be defined as the mean of the noise intensity distribution. This zero-point is not constant as it has been found to slowly change over time. This slowly changing portion of the intensity is computed as a polynomial approximation (using a least squares fitting approach) of the averaged noise trace, which is a simple arithmetic average of all noise pixel traces in a channel. Although least squares fitting has been used, other fitting approaches can be used as well as a hi-pass filter for the pixel traces. The value of the approximating polynomial is then subtracted from every individual pixel trace in a channel to remove this slowly varying noise.

Referring now to FIGS. 10$a$-$d$ and 10$a'$-$d'$, the operation of the hi-pass fiter is graphically illustrated. Looking at FIGS. 10$a$ and 10$a'$, the noise pixel traces are averaged into a single averaged noise trace (top graph), then its polynomial approximation is computed using a least squares algorithm. Next, the value of the polynomial is subtracted from every individual pixel trace. Looking at FIGS. 10$b$ and 10$b'$, the value of the approximating polynomial is subtracted from donor signal pixels as shown in the top graph with the result of the subtraction shown in the bottom graph. The horizontal line (blue in a color image) represents the zero-level, the mean of the background noise intensity distribution for the donor data. Looking at FIGS. 10$c$ and 10$c'$, the noise pixel traces from an acceptor channel are averaged into a single averaged noise trace shown in the top graph. Next, its polynomial approximation is subtracted from every individual acceptor pixel trace. Looking at FIGS. 10$d$ and 10$d'$, the value of the approximating polynomial is subtracted from acceptor signal pixels as shown in the top graph with the result of the subtraction shown on the bottom graph. Again, the horizontal line (blue is a color image) represents the zero-level, mean of the background noise intensity distribution for the acceptor data.

This procedure is performed separately on the traces from each channel, donor and acceptors. As a result, for every identified spot object, a set of channel objects is created. Every channel object contains 9 signal pixel traces, and up to 8 noise pixel traces that were picked from around the signal pixels. Not all of the 9 signal traces are retained in the final data output, since not all of them contain useful signal information. Lower intensity signal traces are eliminated by subsequent processing of donor and acceptor pixel selection methodology described herein.

At this point for every spot, a set of pixel traces is accumulated, from the donor channel and from each acceptor channel. A pixel trace set typically includes 9 signal pixel traces and up to 8 noise pixel traces. The process described below constructs single hybrid traces from the donor channel and from each acceptor channel for every spot. The hybrid traces are constructed to optimize or maximize the signal to noise ratio of the data from every channel.

Donor Pixel Selection

Every individual donor pixel trace is smoothed with a Smart Smoother as described below, then compared to the noise level in order to determine segments, where the signal goes above the noise level (lifetime). The noise level NL is computed as a square root of a square average of all noise samples across all noise pixel traces, assuming that the mean of the noise intensity distribution is zero after application of the hi-pass filter.

Next, a score of every pixel trace is computed as an average of original (non-smoothed) data during the lifetime. If the lifetimes of individual traces differ significantly, the traces with short lifetimes (shorter than half of the longest lifetime in the set) are rejected.

The remaining traces are sorted by score. Then those traces having a score higher than half of a highest score are selected for averaging into the hybrid trace. However, if the number of traces having a score greater than half the score of the highest score is greater than 5, then only five traces are selected so that the five have the highest score and their score is greater than half the score of the highest scored pixel.

Figure 12:
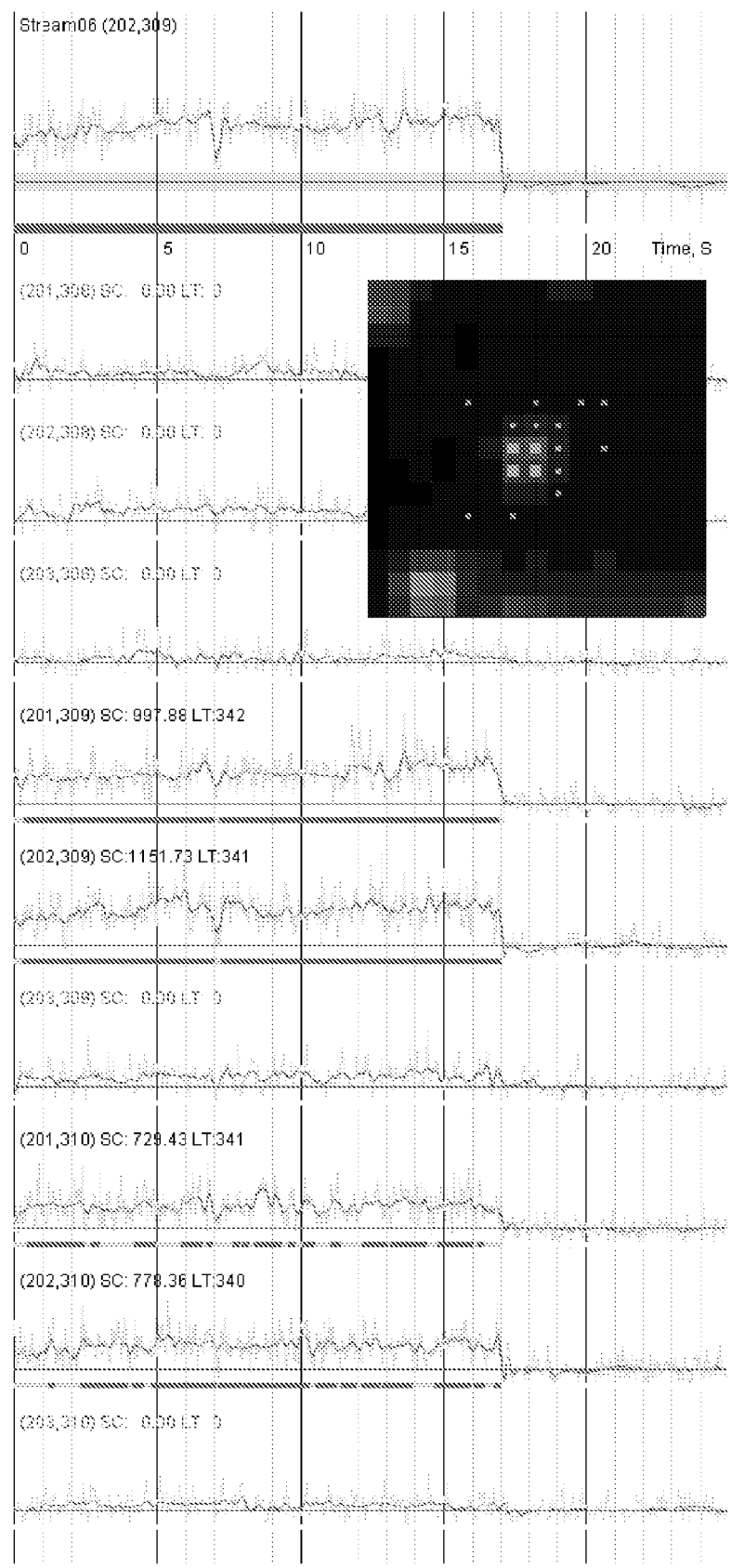
FIG. 12 depicts the intensity-based donor pixel selection algorithm.
Figure 12:
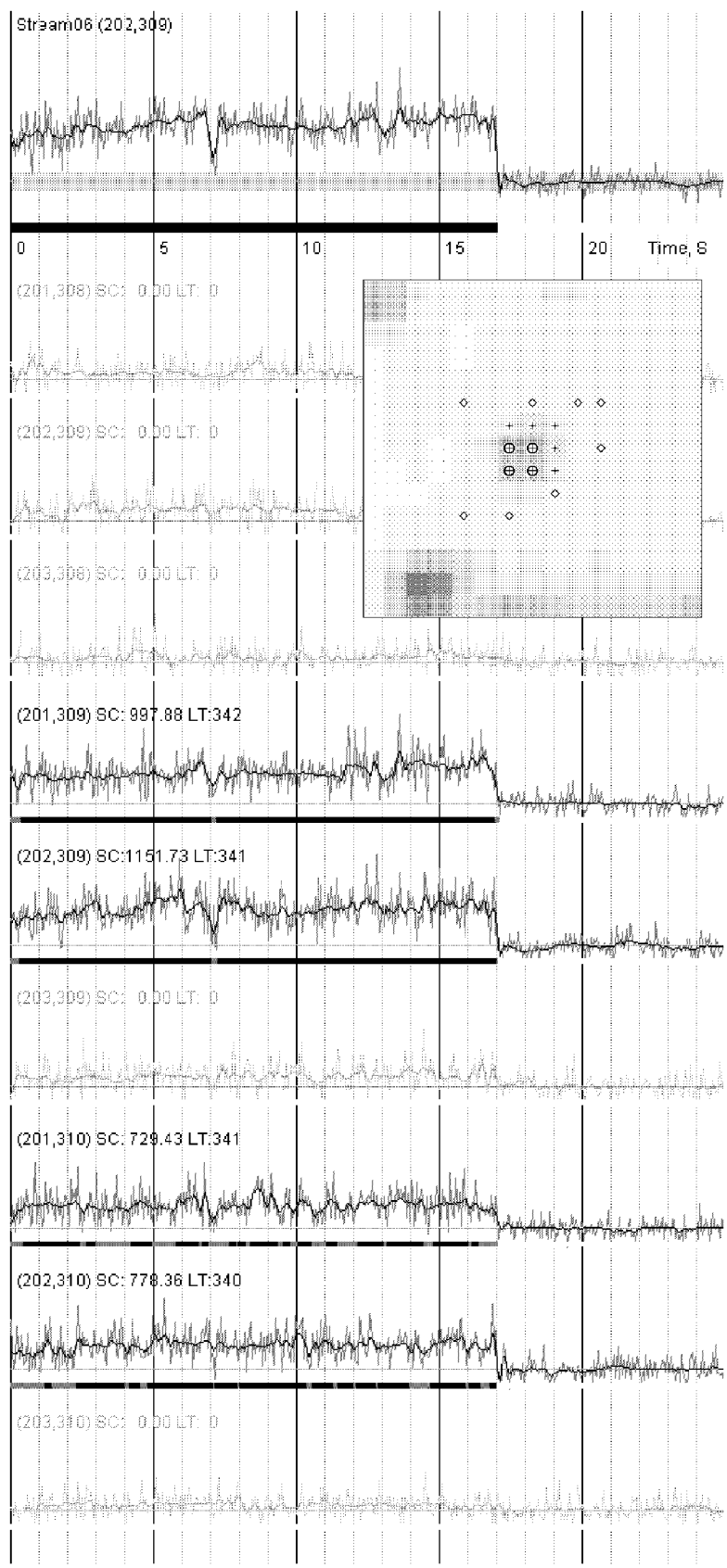

Referring now to FIGS. 12 and 12', donor pixel selection process is illustrated graphically. The figure includes an overlaid data image and ten panels that include pixels traces. In the figure, the nine bottom panels show the individual donor pixel traces in the 3×3 donor pixel array. The traces that do not include solid segment lines below the trace represent traces rejected by the anaiysis and are not used in producing the average donor trace shown in the top panel. The rejected donor pixels are shown as dots in the pixel image box. Each trace having a solid segment line below the trace is graphed with its original, non-smoothed data (light green in a color image) shown as fine line about a solid thicker line (dark green in a color image) representing its smoothed data generated using the Smart Smoother of this invention. The horizontal bars (green in a color image) below the accepted traces are the lifetime segments used in calculating thehybrid donor trace.

The top panel in the figure is the hybrid trace, an average of the selected traces. The gray horizontal strip centered about a zero line evidences the final noise level, computed as the standard deviation centered at 0 of the hybrid noise trace. The solid bar (green in a color image) underneath the trace shows the donor's hybrid lifetime. The overlaid data image shows the spacial position of the donor signal pixels and noise pixels. The selected traces are shown as large boxes, while rejected traces are shown as small boxes. In this example, four traces were selected and five traces were rejected. An equal number of noise traces randomly picked from the 8 available are averaged into a single hybrid noise trace. From this averaged noise, the final noise level is computed as the standard deviation from 0 of the hybrid noise pixels.

On the final hybrid donor signal trace, a few general parameters are computed: (1) a lifetime LT representing the number of data samples (frames) above the noise level (convertable to seconds by multiplying by time between samples), (2) average donor intensity during the lifetime Int, and (3) donor signal to noise ratio SIN, computed as Int/NL.

At this point of the analysis a few spots from the initial list may be rejected. The rejection criteria is based on the computed average lifetime and signal to noise ratio computed during the donor lifetime compared to the configurable minima of these values. The minimum lifetime parameter contained in the parameter bad_lifetime, which is adjustable and is currently set to 20 data samples or frames, and a signal to noise minimum parameter designated bad_dsn, which is also adjustable and is currently set to 1.5. The configurable minima were chosen based on empirical evidence that it is practically impossible to reliably detect anything at all in traces that do not meet these criteria.

Acceptor Pixel Selection

The discrimination between good and not so good acceptor pixel traces is more tricky, because the acceptor signals are typically short and week. The inventors currently use two competing methods to analyze the acceptor signals. These two methods can and often do produce different results. The inventors then use special logic to choose the method that yield the best results.

Figure 13A:
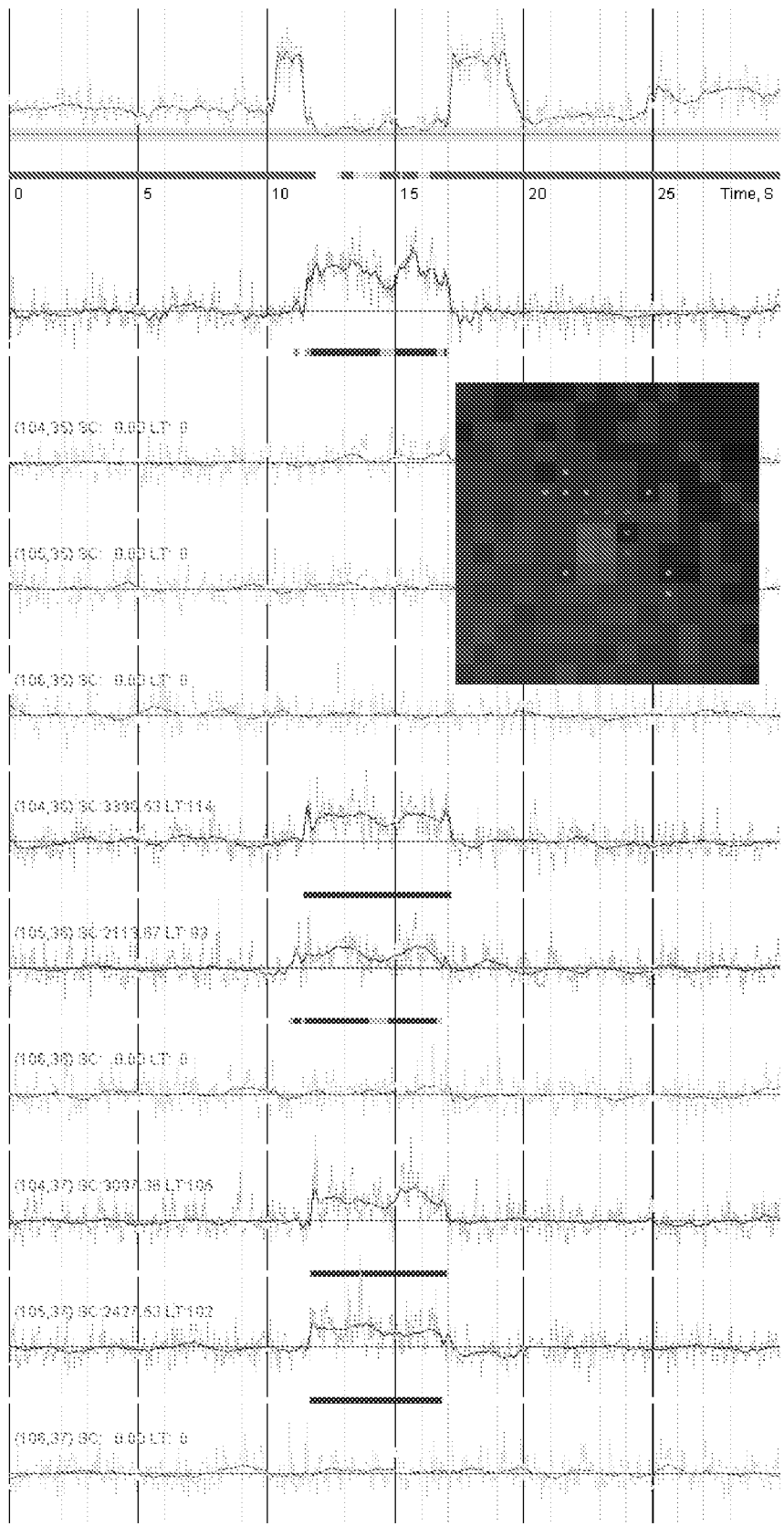
FIG. 13a depicts the intensity-based acceptor pixel selection algorithm.
Figure 13A:
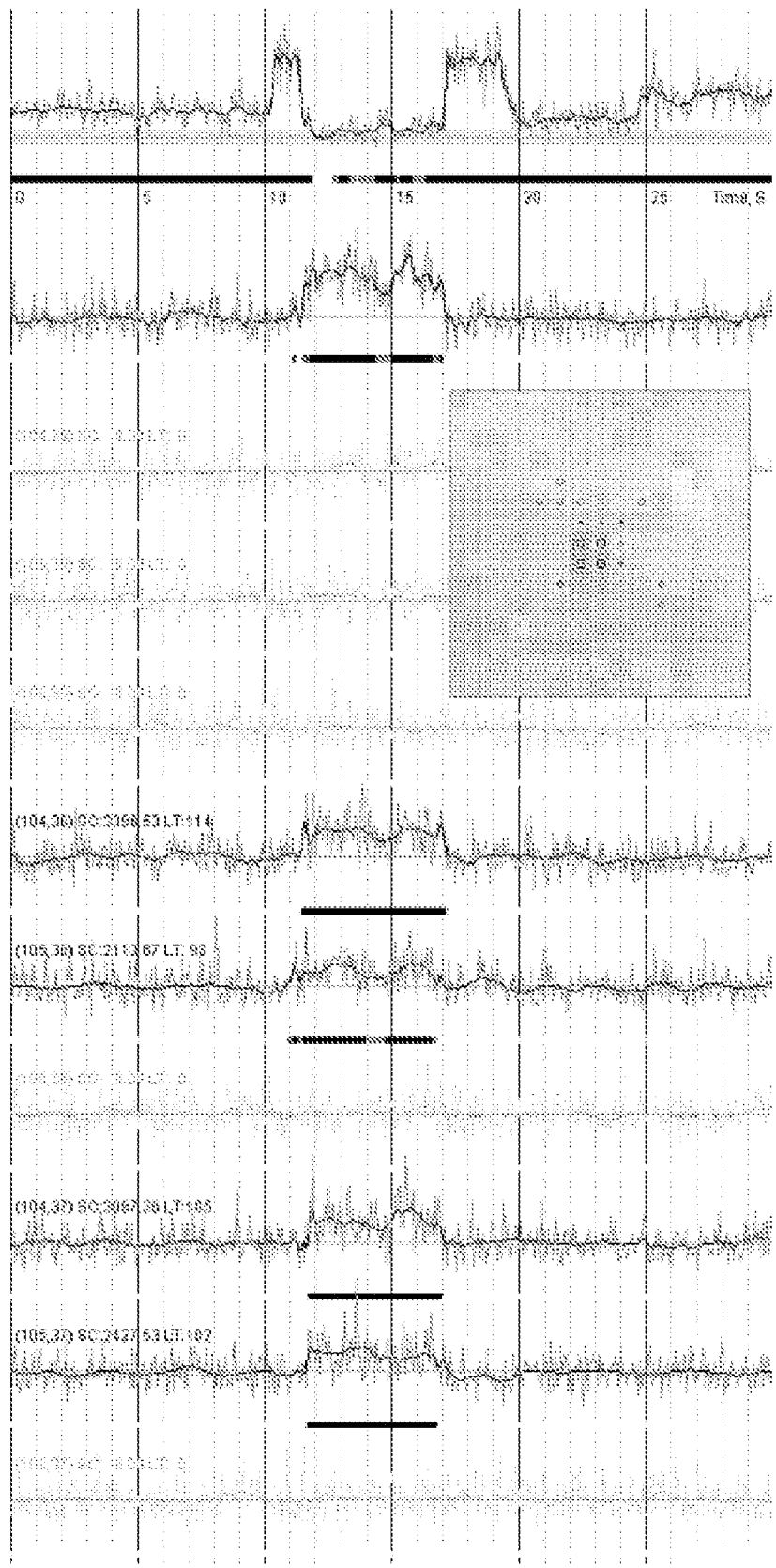

The first method is an intensity-based method and was optimized to detect long-living events. The method applies a Smart Smoothing routine (described below) to each pixel trace, then computes lifetimes as segments in the acceptor traces, where the smoothed data values are above the noise level. The method then assigns a score to the computed lifetimes as the ratio of standard deviation during lifetime to standard deviation outside lifetime. FIGS 13a and 13a' shows the score scaled by the factor 1000 next to each pixel trace. The factor 1000 is chosen solely for presentation, it has no meaning in the application of the method.

The traces are then sorted by score in descending order, and a cut-off value is defined as half the average of the two highest scores. The cut-off at 50% is chosen because adding lower intensities to the final hybrid trace does not improve signal to noise ratio, which has been confirmed experimentally on both simulated and real data. The traces that have lower scores, are rejected.

An additional routine is applied to check whether the lifetimes of individual traces match each other at least half of the time. If the lifetime of a trace has a significant (more than 50% of the longest lifetime) mismatch with the others, the trace is also rejected.

Finally, a spacial configuration of the pixel cluster is checked to ensure that non-adjacent pixels were not included in the cluster, because non-adjacent pixels cannot be from the same replication or sequencing complex.

Referring now to FIGS. 13a and 13a', the intensity-based acceptor pixel selection method is illustrated graphically. In the figure, the nine bottom graphs show individual acceptor pixel traces. The grayed graphs are the traces that have been rejected by the logic. The top (green) graph shows donor hybrid trace, and the graph right below it, the hybrid acceptor trace obtained by averaging selected (non-grayed) individual acceptor pixel traces. The overlay picture shows spacial location of all nine candidates, selected pixels shown in bold, and individual noise pixels.

An alternative algorithm (derivative-based) is optimized for short-living events, if any. It works in a very similar way, but instead of smoothed function of the trace itself, it takes the product of donor and acceptor derivatives, then computes "noise level" as the standard deviation, "lifetime" when the derivative product is above the noise level, "scores" of the traces, and so on.

Figure 13B:
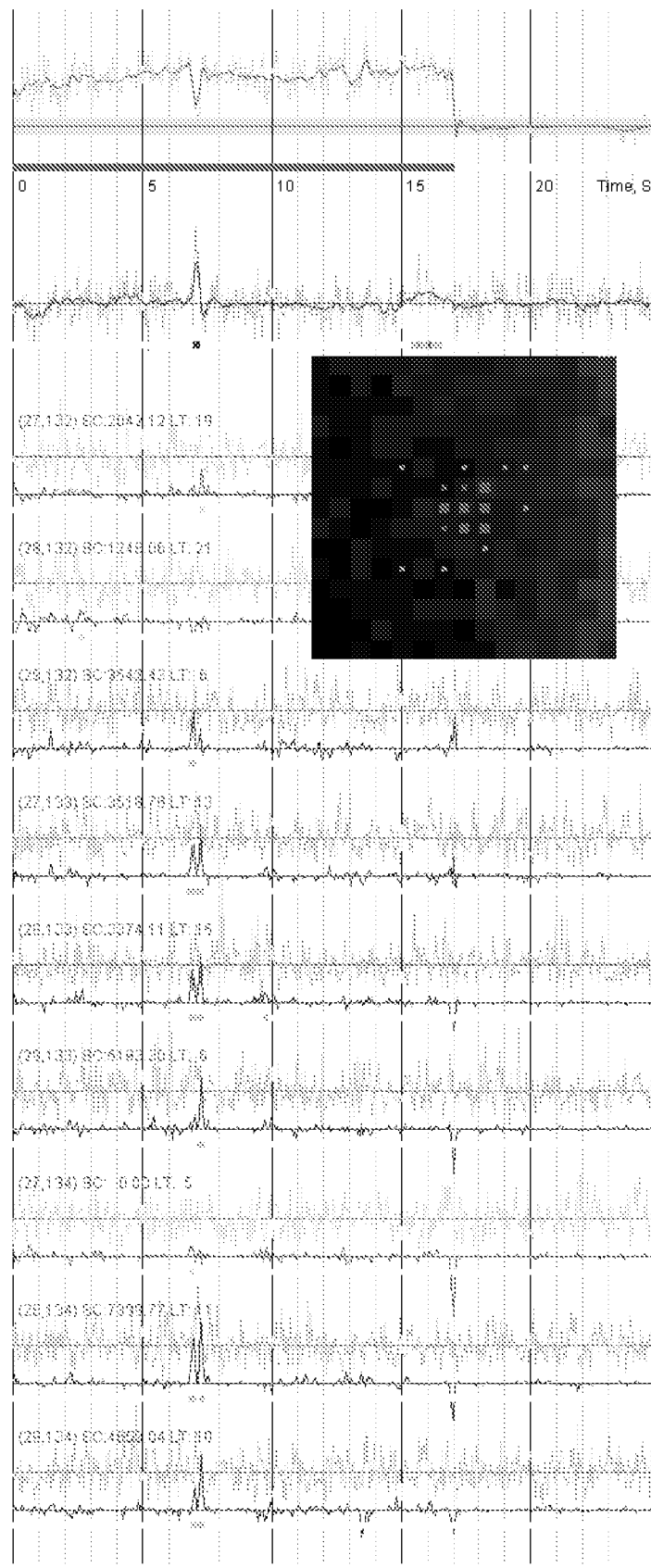
FIG. 13b depicts the derivative-based acceptor pixel selection algorithm.
Figure 13B:
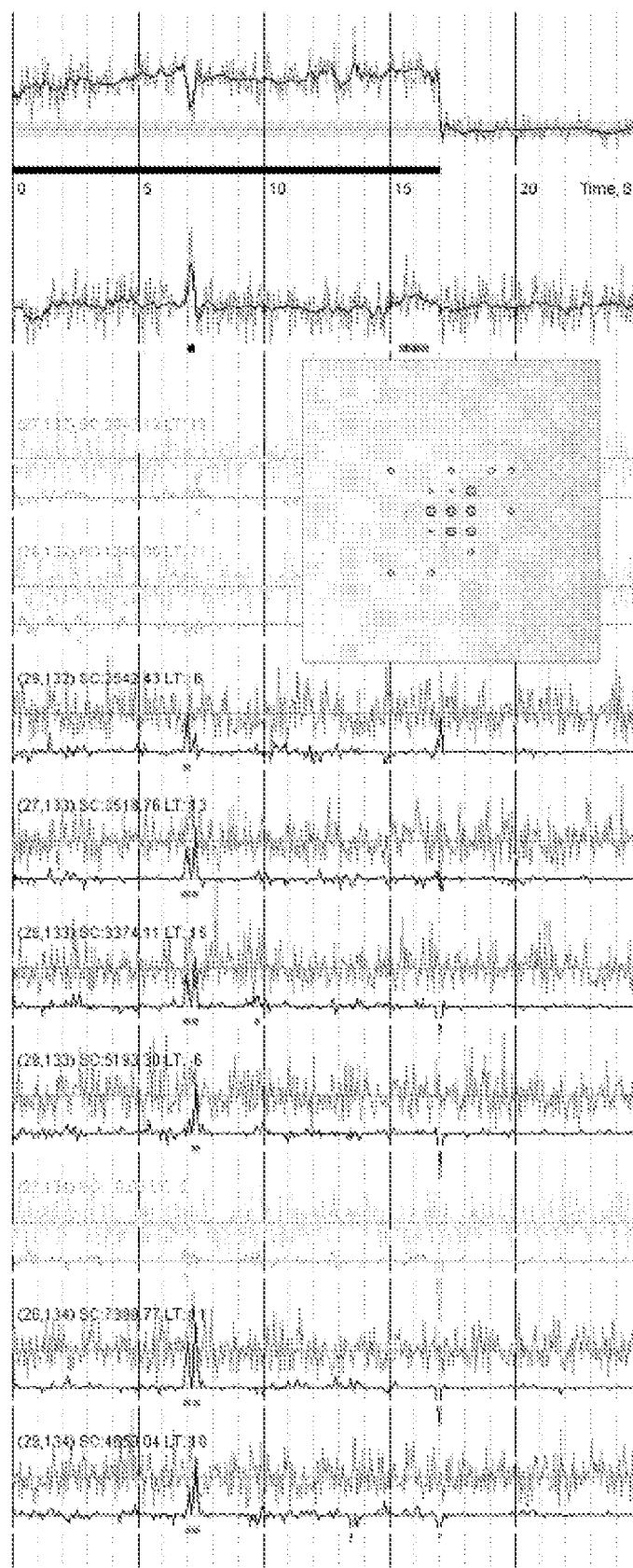

Referring now to FIGS. 13b and 13b', a derivative-based acceptor pixel selection process is illustrated graphically. The graphs below the time line show individual acceptor pixel traces. The grayed one(s) have been rejected, and did not contribute to the average (red) graph at the top. Below each graph the product of its derivative and donor's derivative is shown. The green graph at the top is the hybrid donor signal.

After the intensity-based algorithm is applied, the logic checks whether it has produced satisfactory results. That means, it detected one or more acceptor lifetime segments, comparable in duration to the S-G parameters nL and nR, and if the signal to noise ratio of these segments is higher than minimal signal to noise ratio, which can range from about 1.5 to about 2, the current preferred value is 0.7. If the above conditions are not met, the logic applies derivative-based algorithm. Finally, the logic averages selected acceptor traces into a single hybrid trace, then averages an equal number of noise traces, to create a hybrid acceptor noise channel, which is expected to have a compatible noise level.

Figure 14:
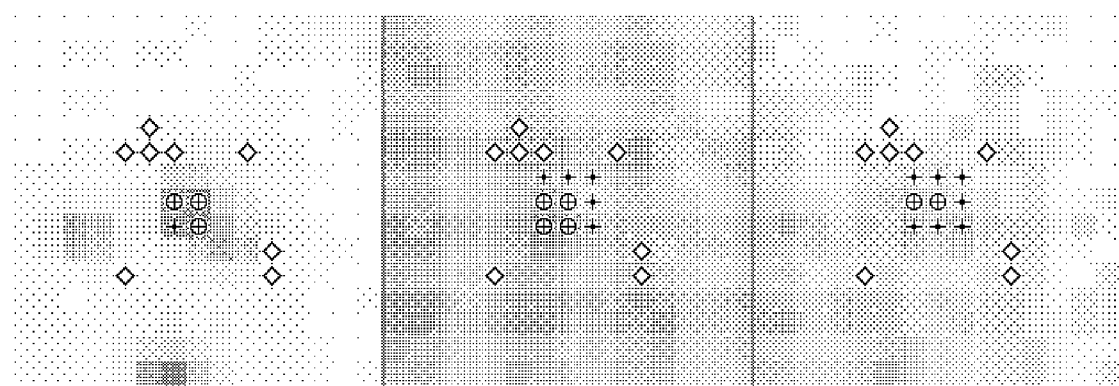
FIG. 14 depicts graphically the results of the donor and acceptor pixel section process. showing donor—acceptor 1—acceptor 2 overlays after pixel selection, where the ⊕ symbols represent accepted pixels, the+ represent rejected pixels, the ◇ symbols represent noise pixels.

Referring now to FIG. 14, the results of the filtering and hybridizing operations are shown graphically for the donor, acceptor 1 and acceptor 2.

Signal File Format

At this point, the result may be saved into a signal file in the following format:
spotdata (donCol,donRow) n samples delta
stack stack_name
directory stack_directory
spot spotname col row mask
spot . . .
start data
spot0sample[0] spot1sample[0] . . . spot0sample[1] spot1sample[1] . . . .
spot0sample[n samples-1] spot1sample[n samples-1] . . .
stack_name—file name of the stack file (normally, without extension);
stack_directory—path to the directory of stack file;
n samples—number of data samples in every trace, equal to the number of frames in the stack file;
delta—delta time in milliseconds between samples;
donCol,donRow—coordinates of the central donor pixel;
spotname—trace name, one of the following:
don—cumulative donor signal trace
donn—cumulative donor noise trace
ac1—cumulative acceptor 1 signal trace
acb 1n—cumulative acceptor 1 noise trace
ac2—cumulative acceptor 2 signal trace
ac2n—cumulative acceptor 2 noise trace
col,row represents the coordinates of the signal center pixel. The parameter mask is a bit mask that shows which of the 9 pixels in the 3 ×3 area around the center pixel have contributed to the cumulative signal. Bit 0 is set when the pixel at (col−1,row−1) has been selected, bit 1 for (col,row−1), and so on. The value is an hexadecimal sum of one or more bit values represented in the table below.

|  | col−1 | col | col+1 |
|---|---|---|---|
| row−1 | 001h | 002h | 004h |
| row | 008h | 010h | 020h |
| row+1 | 040h | 080h | 100h |

The value of mask is meaningless for noise traces.

A fragment of such a file is shown below:
spotdata (196,266)1000 25
stack Stream05
directory D:\Dteam\Detection Data\05-10-05\16pCg-QT-LAA-PiW-25ms
spot don 196 266 030
spot donn 196 266 1FF
spot ac1 23 89 1B8
spot ac1n 23 89 1FF
spot ac2 23 266 0BA
spot ac2n 23 266 1FF
start data 305-107 33 106-1-21
276 62-25 10 17-39
233 13 146-7-42-9
504 86 170-64-25 45

The Donor Model

At this point in the analysis, the signals are analyzed in a digital format. Thus, a signal can be considered as transitioning between a digital zero state and a digital unit state, i.e., transitioning between 0 and 1. While the digital zero level can be established fairly well by examining the noise channel, the digital unit level poses a problem, because it is not stable.

For acceptor channels, the task seems to be relatively easy and straightforward, because the acceptors are normally at their zero level, well established and fixed by the hi-pass filter. That is, the acceptors are in a dark state unless or until they receive sufficient energy from a source to fluoresce. Although some background acceptor emissions are seen, the principal pathway to acceptor fluorescence is via energy transfer from an excited donor as the sample is being irradiated with light the only the donor can accept. Therefore, the process simply assumes that an acceptor is at zero level as long as its intensity does not go above the noise level.

On the other hand, the donor data is more difficult to digitize. From a chemical view point, the donor signal can be on—it is being irradiated by a light source on a continuous basis. The donor can be transferring energy to an acceptor. The donor can inter-system cross from a singlet manifold to a triplet manifold, which is observed experimentally as blinking. The donor can non-radiatively lose excitation energy, also observed as blinking. The donor can temporarily photobleach or permanently photobleach. Additionally, the donor intensity has been found to fluctuate around its unit level and its unit level has been found not to remain constant over time. Thus, this routine is designed to find donor unit levels at different moments in time.

Because the donor signal may not only slowly change around its supposed unit level, but swiftly go up and down as well, a simple technique like a hi-pass filter is an ineffective processing filter. Before applying a polynomial fitting routine to the donor traces, the process breaks down the entire donor signal into segments, on which no swift and rapid changes occur. This segmentation of the signal is done by computing the signal's derivative and finding its outstanding extrema, that is, where the derivative goes above or below 1.2 times its own standard deviation. The value of 1.2 times was experimentally established to give the best overall results, but the parameter can range from about 0.8 to about 2.0. Every such extremum defines a segment boundary. The area between two consecutive extrema is a segment. At this point, there are too many segments, and most of them are too small.

Figure 15:
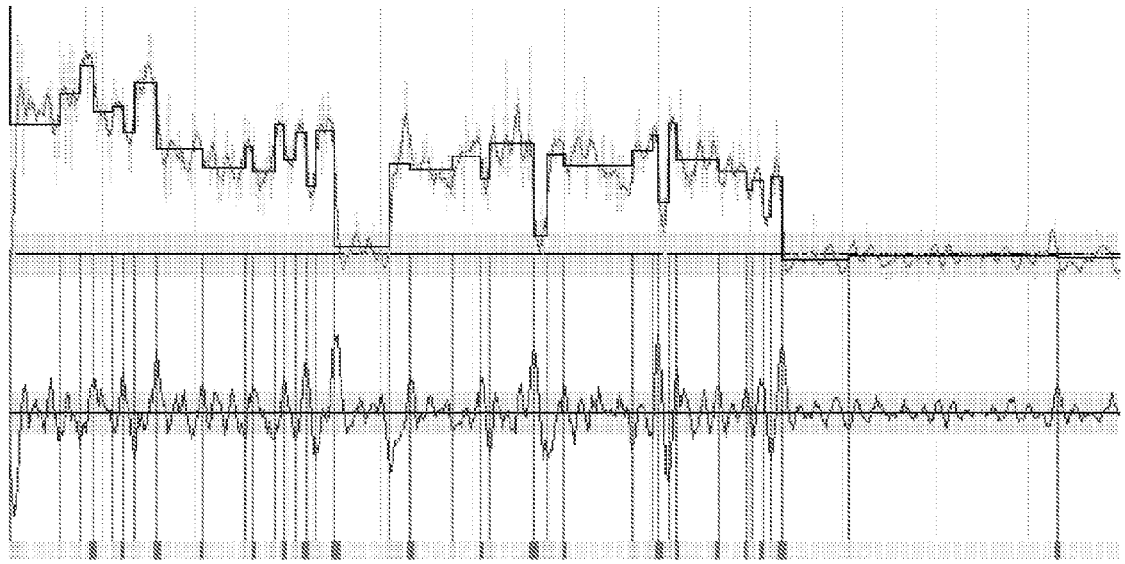
FIG. 15 depicts donor model represent initial segments.
Figure 15:
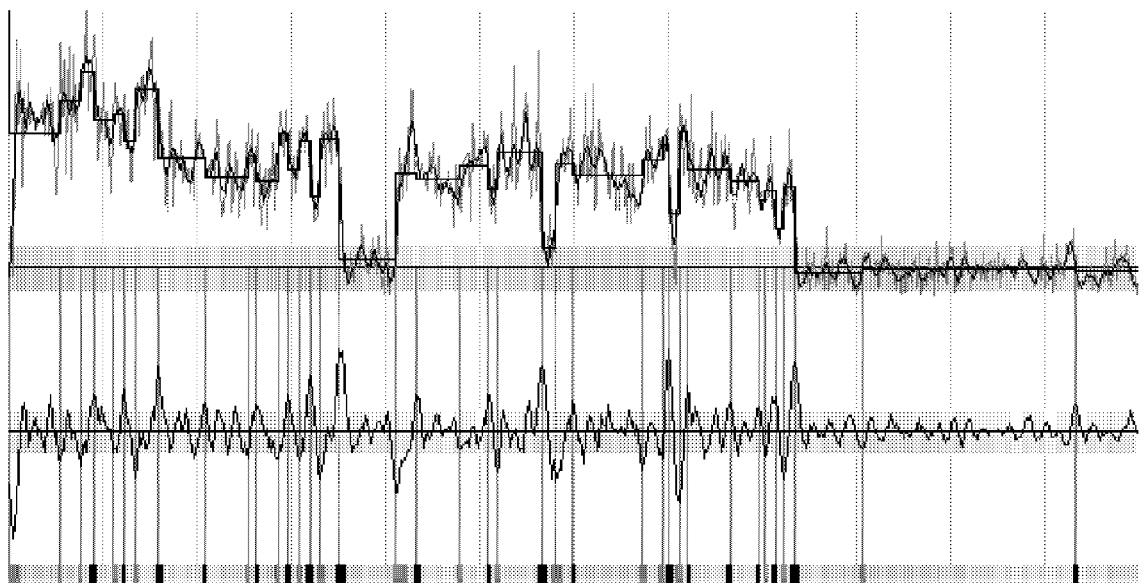

Referring now to FIGS. 15 and 15', aspects of the donor model relating to initial signal segmentation are illustrated graphically. The bottom portion graphs the derivative of the donor signal (red in a color image). The gray area denotes 1.2 times its standard deviation as an evidence of the noise level associated with the signal. The vertical lines (cyan in a color image) in the bottom graph mark boundaries of the segments derived by application of the routine onto the data trace. The top portion graphs the donor signal; the raw signal is shown in light gray (light green in a color image) and the smoothed signal is shown in dark gray (dark green in a color image). Again, the gray area denotes 1.2 times its standard deviation as an evidence of the noise level associated with the signal. The straight line graph (dark blue in a color image) plotted through the raw and smoothed data show averaged intensities for the segments.

For every segment, the method computes two parameters. The parameters are the segment length or temporal duration and the average intensity of the signal in that segment. These two parameters are then used to decide, whether one or more adjacent segments should be joined into a single larger segment. This joining is typically done when two adjacent segments have close average intensities. The term "close average intensities" means that adjacent segments have intensity values that differ by between 1 and 2 times the noise level. In certain embodiments, the term "close average intensities" means that the adjacent segments have intensity values that differ by less than 1.4 times the noise level. Segments are also be joined, if small data segment in interposed between to relatively long segments. Generally, a small data segment is a segment that extends over less than 40 frame or data samples. In certain embodiments, the routine joins two segments if an intervening segment as a duration between about 20 and about 40 data samples. In other embodiments, the routine joins two segments if an intervening segment as a duration between about 30 data samples. The routine consider segments separated by a short segment relatively long for the purpose of segment joining if the segments on each side of the short segment have durations or lengths 1 to 2 times larger than the short segment. In certain, embodiments, the two segments on each side of the short segment have durations or lengths 3 to 4 time larger than the short segment.

Figure 16A:
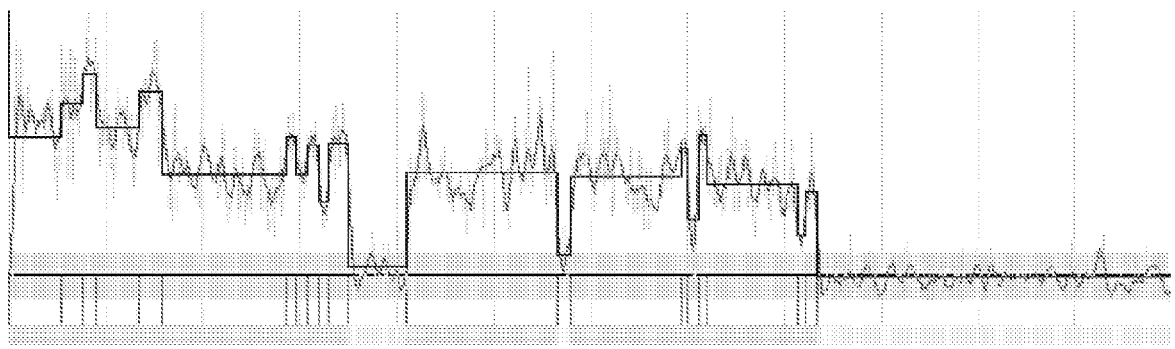
FIGS. 16a-16c depicts donor model represent optimizing segments.
Figure 16A:
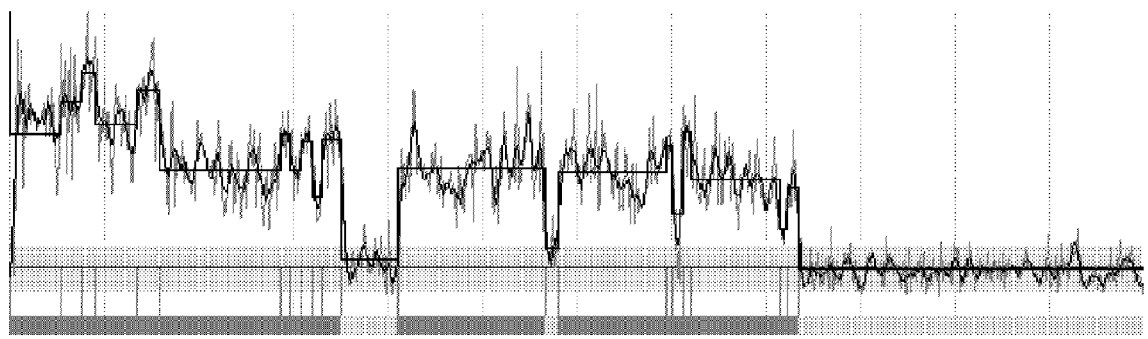
Figure 16B:
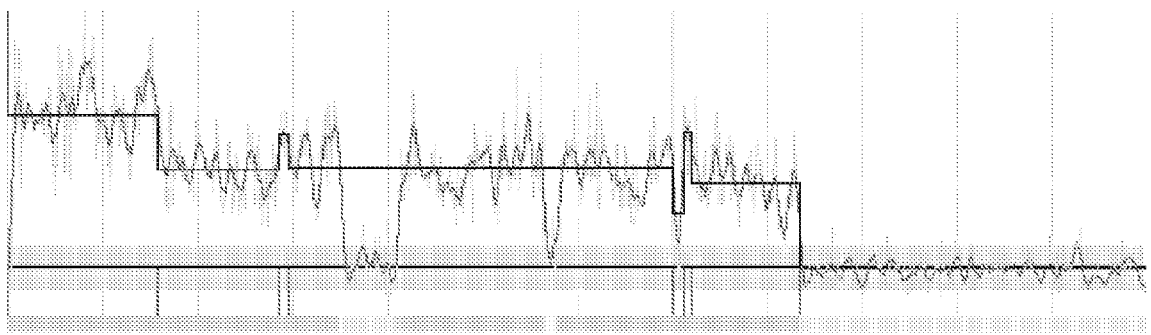
Figure 16B:
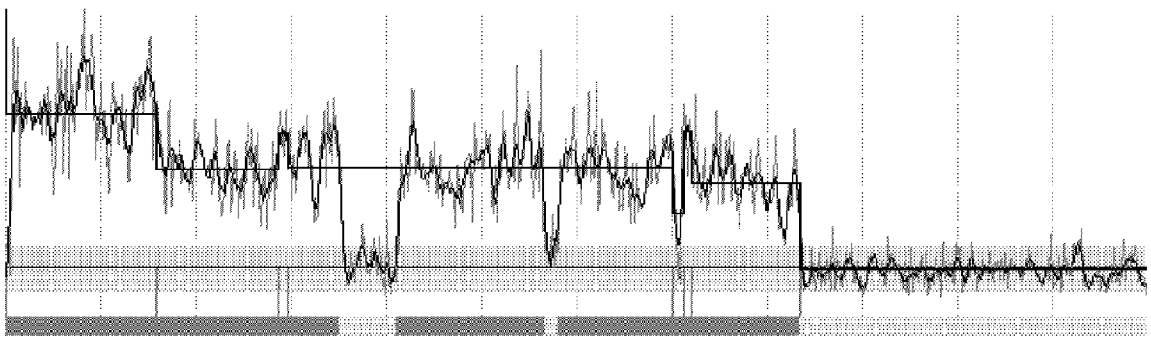
Figure 16C:
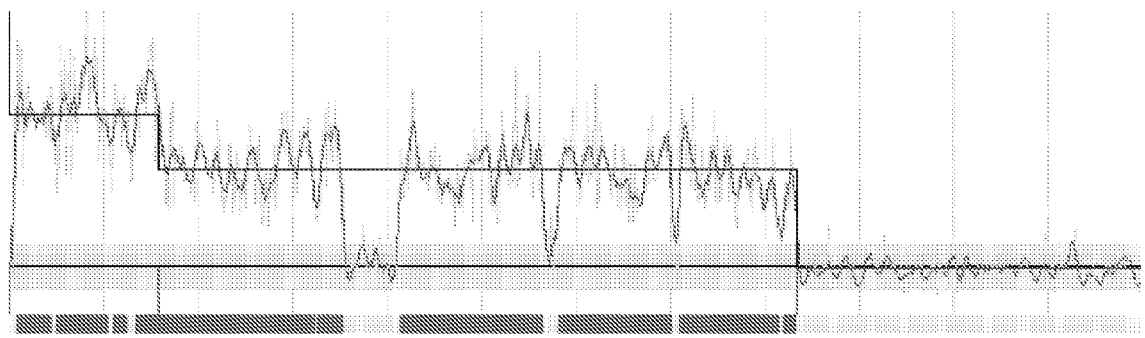
Figure 16C:
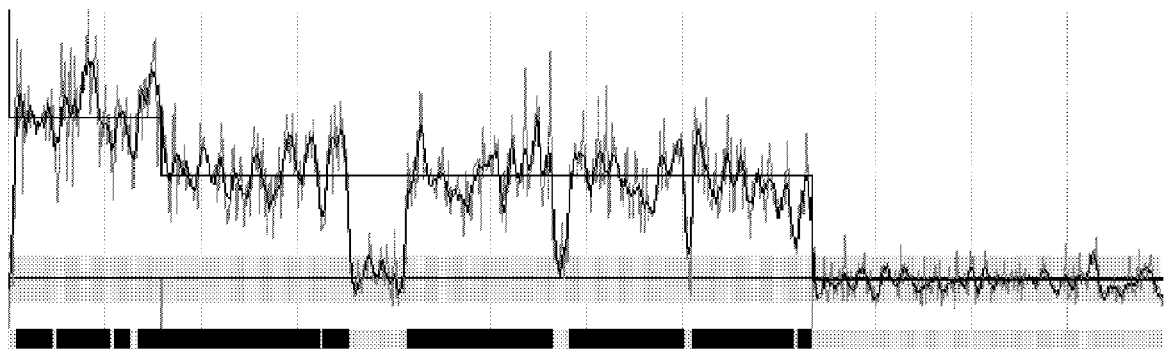

Referring now to FIGS. 16a-16c and 16a'-16c', aspects of the donor model relating to segment optimization is illustrated graphically. A series of successive optimizations is applied to the initial list of segments. For every segment, the segment optimization routine computes a segment length or duration and a segment average donor intensity. Based on these two parameters, several adjacent segments are joined into large one segments. Also, the routine determines, whether the donor signal is mostly at its unit level as evidence by horizontal and vertical lines through the data trace (blue lines in a color image). This segmentation representation of the data trace also include a horizontal line than represents when the fluorophore is a zero level (not emitting light) (red lines in a color image).

The optimization routine also distinguishes between segments, where the signal is mostly at the unit level, and the segments, where the signal is mostly at the zero level. For the former, the unit level can be computed out of segment data alone, but for the latter, the unit level has to be derived out of its neighbors.

The optimization routine also distinguishes between segments, where the signal is mostly at the unit level, and the segments, where the signal is mostly at the zero level. For the former, the unit level can be computed out of segment data alone, but for the latter, the unit level has to be derived out of its neighbors.

Figure 17:
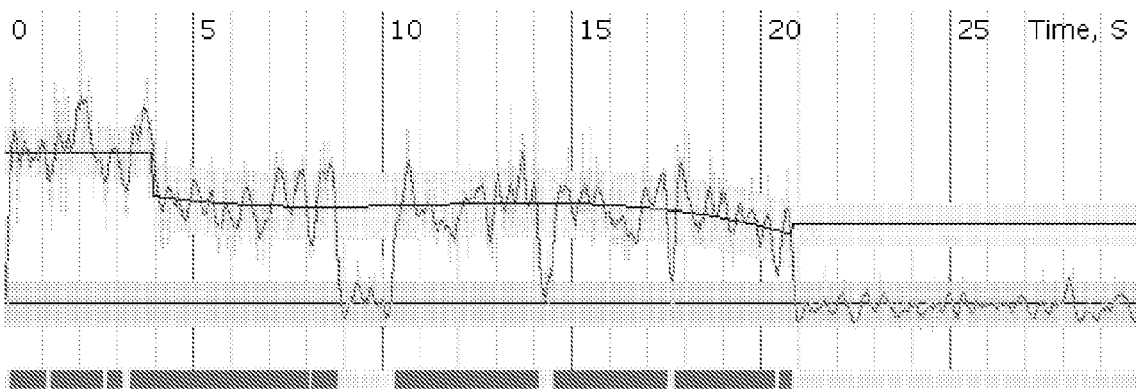
FIG. 17 depicts donor model representing final stage optimization.
Figure 17:
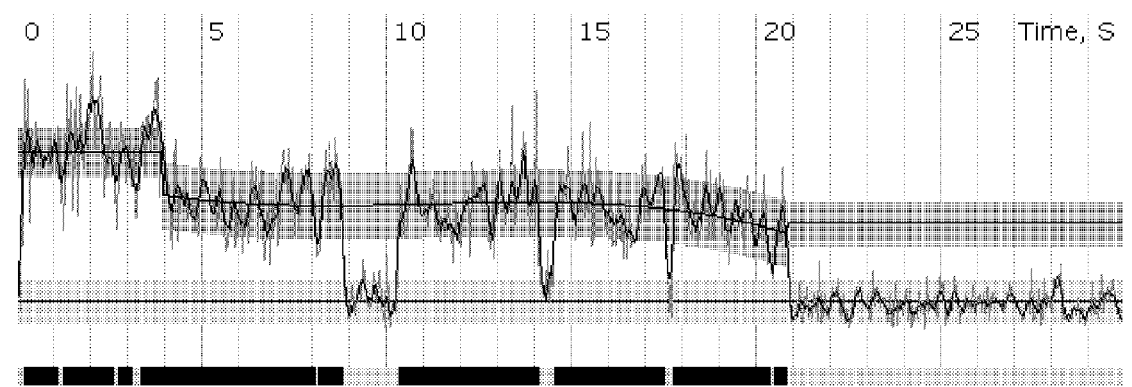

Referring now to FIGS. 17 and 17', aspects of the a donor model relating to final stage processing is illustrated graphically. The unit segments, segments where the fluorophore is active, are best fitted to a polynomial function represented by a solid curve through the trace (blue in a color image). The standard deviation (unit noise lever) associated with the polynomial function is shown as a gray area with the curve centered therein. The dark gray horizontal bars (dark green in a color image) at the bottom of the figure show segments where the donor signal has a high intensity value; while light gray horizontal bars (light green in a color image) show segments, where the donor signal has a low intensity value.

The final step in the process is to fit all unit segments, segments where the fluorophore signal stays at the unit level most of the time, with a polynomial function that follows the variable unit level of the signal intensity. The standard deviation associated with polynomial function is also computed, and serves as a measure of noise level around the unit level. For all zero segments, the unit level is assumed to be constant, and equal to unit level value computed at the previous step, and the noise level is assumed to be equal to the background noise level.

Now, the donor trace at a particular location in the viewing field is represented by a set of zeros and ones through the frames. The value of 1 over a segment of the donor trace signifies that the donor is in a high state and is simply determined by comparing the trace segment to the local unit level less local noise level—if the signal is above this value, the unit level value is set at 1 (donor is in a high state); otherwise, the unit level value of this donor is set a 0 (donor is in a low state). In certain traces, a donor segment may not fall to a value below local noise level, but is situated between two much higher intensity peaks; in such as case, the segment is also assigned a zero value.

Lo-Pass Filtering Algorithm

A low-pass filter is usually applied to signals that are variable, that is both slowly varying and corrupted by random noise. In such case, it is sometime useful to replace each actual data point with a local average of surrounding data points. Because nearby points measure very nearly the same underlying signal value, averaging over these surrounding data points can and often does reduce the level of noise without much biasing of the averaged signal value obtained.

The present invention utilizes a particular lo-pass or smoothing filter sometimes referred to as a "Savitzky-Golay" lo-pass filter, "least-squares" lo-pass filter, or DISPO ("Digital Smoothing Polynomial") lo-pass filter. The lo-pass filter operates by replacing a value of every input data point with a value derived from a polynomial fitted to that input data point and several nearby, generally adjacent, input data points.

Figure 18:
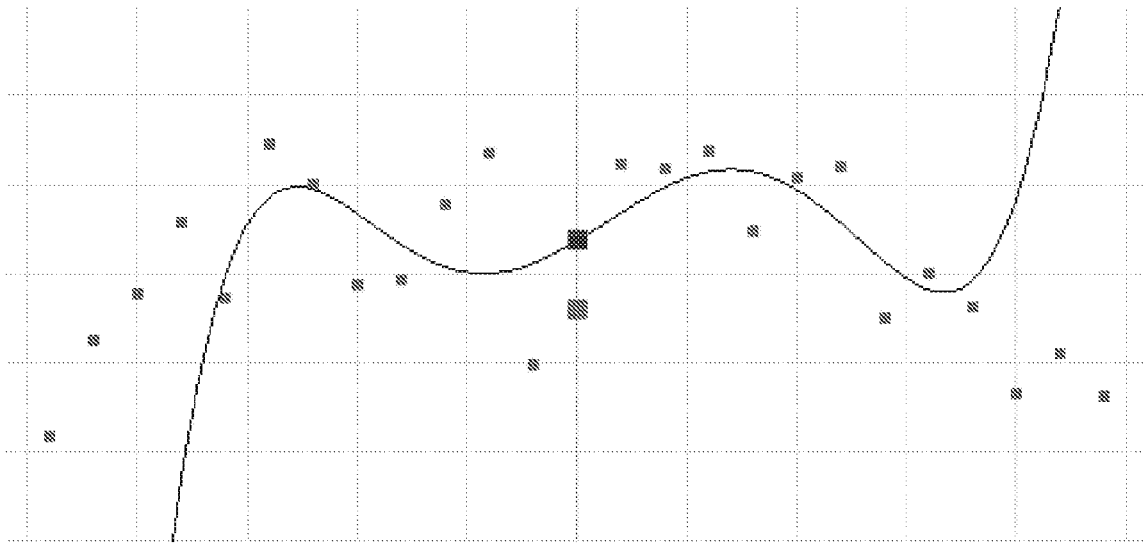
FIG. 18 depicts a numeric experiment using 17-point Savitzky-Golay smoothing filter.
Figure 18:
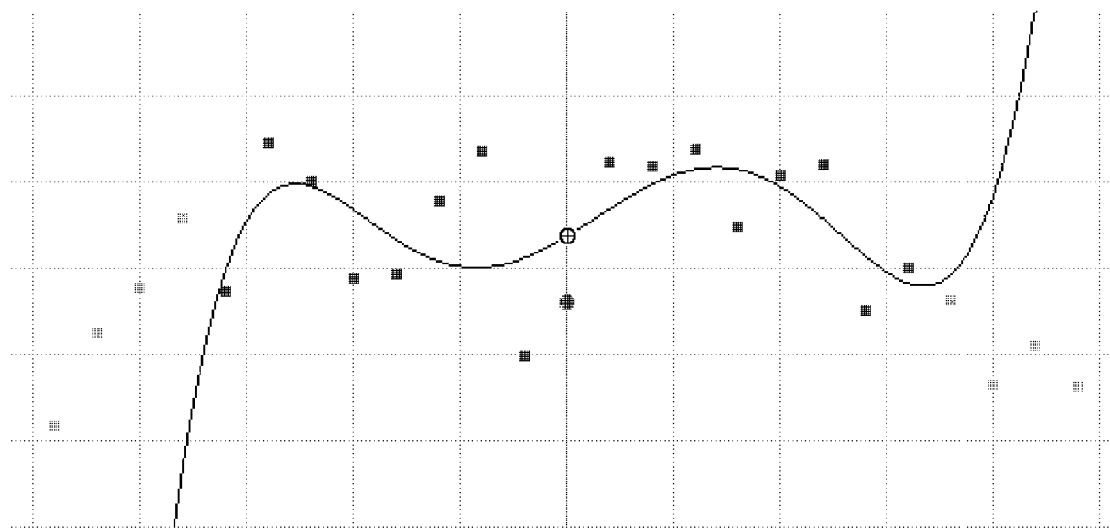

Referring now to FIGS. 18 and 18', a Savitzky-Golay, lo-pass smoothing filter is illustrated graphically. For a data point $f_i$ represented by a large square DP (green in a color image) in the figure, the filter then fits a polynomial of order M represented by the solid line curve (blue in a color image) to all data points from i−nL to i+nR (green dots), then replaces the value of the data point $f_i$ with the value of the polynomial at position i represented by a large square PV (red in a color image). In this example, nL=8, nR=8, and M=6.

Because the process of least-squares fitting involves only a linear matrix inversion, the coefficients of a fitted polynomial are themselves linear in the values of the data. Thus, all the polynomial fitting can be done in advance resulting in a set of coefficients $C_{i-nL} \ldots C_{i+nR}$, which do not depend on the particular data point values. Therefore, the polynomial or smoothed value is computed simply as a linear combination of the coefficients $\Sigma C_j f_j$ (j=i−nL . . . i+nR) of these pre-computed coefficients and the data samples around the $i^{th}$ point.

A similar technique is used to obtain of smoothed data values of the derivative of a data trace. In this case, the $i^{th}$ derivative value of the data trace is replaced not by the value of the fitting polynomial, but by the value of the derivative of the polynomial at the $i^{th}$ data position. As is true with the application of the lo-pass filter to the trace data, the coefficients for the polynomial can be performed in advance, by pre-computing coefficients $C_{i-nL} \ldots C_{i+nR}$. In most embodiments of this filtering process for computing replacement derivative values, the fitting polynomials is at least of order 4.

The parameters of the Savitzky-Golay, lo-pass smoothing filter are:

nL—number of nearby pixels to the left of the i-th pixel.
nR—number of nearby pixels to the right of the i-th pixel.
M—order of the fitting polynomial.
ld—order of the derivative (if 0, the function itself).

Figure 19:
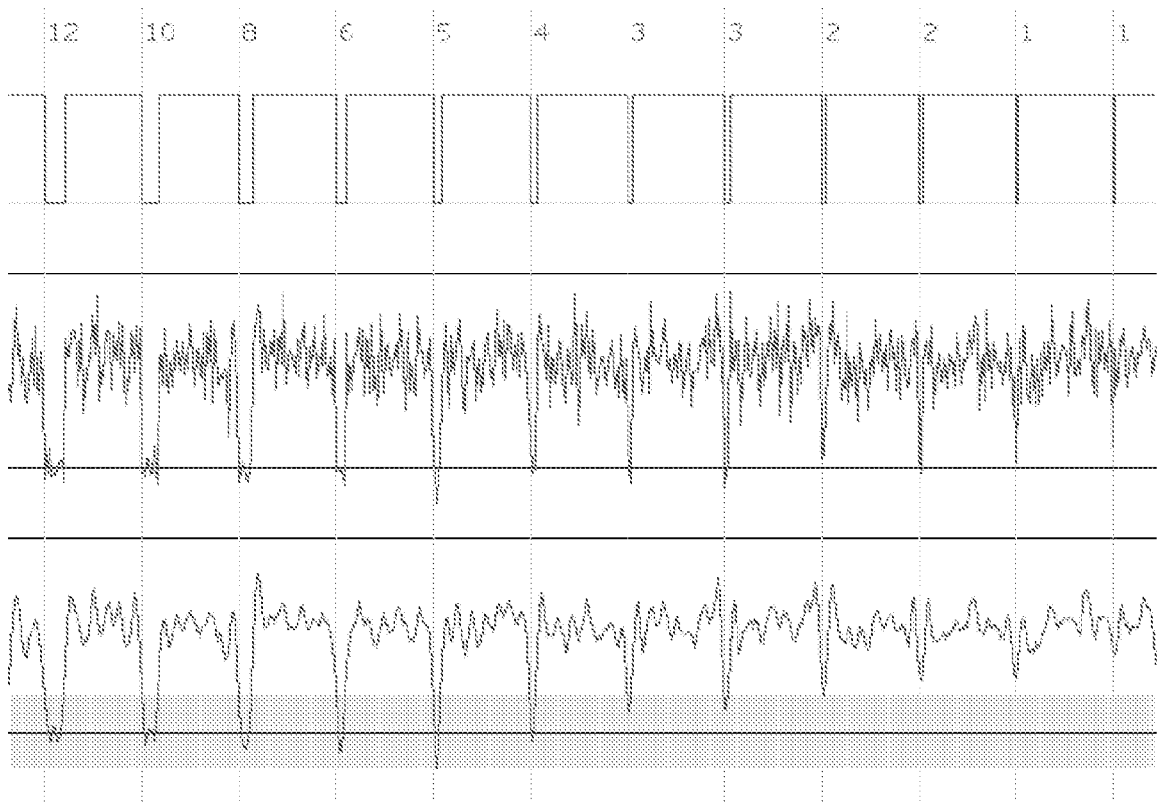
FIG. 19 depicts simulated data, simulated data after addition of noise and after smoothing of the noisy data to shown the veracity of the smoother.
Figure 19:
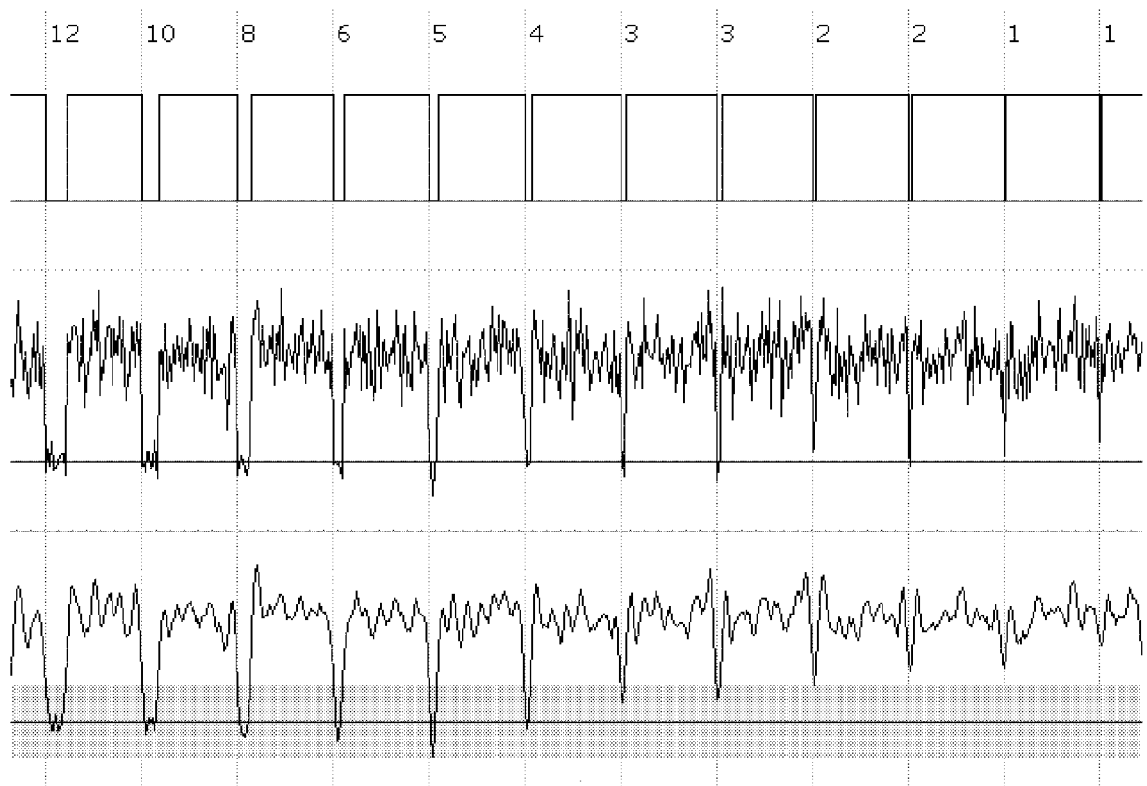

Referring now to FIGS. 19 and 19', a numeric experiment using a 17-point Savitzky-Golay smoothing filter is illustrated graphically. In the top panel, the simulated data comprises a constant signal interrupted by progressively narrower gaps. The size of gaps in data is shown above as numbers. In the center panel, the simulated data is shown with simulated white Gaussian noise added having a standard deviation of about 025. In tbe bottom panel, the noisy data of the center panel is shown after applying a Savitzky-Golay, lo-pass smoothing filter with nL=8, nR=8, M=6, and ld=0. The horizontal gray bar represents the noise level, computed as $\sqrt{2}$ times the standard deviation of the noise (about 0.3 in this case).

For example, for a lo-pass filter represented by the set of input parameters nL=1, nR=1, M=1, and ld=0, a set of 3 coefficients $C_{i-l}$, $C_i$, and $C_{i+l}$, are determined to have the values ⅓, ⅓, and ⅓, respectively, which is identical to the three point averages of the smoothing filter.

Derivative Anti-Correlation

Several parts of the detection software use a concept, which the inventors call DAC—Derivative Anti-Correlation. DAC is a function operates by deriving a value of a parameter m dash. If at any point both donor and acceptor derivatives have the same sign, then the value of DAC is set to zero (0). If at any point both the donor and acceptor derivatives have opposite signs, then the value of DAC is set as the product of the acceptor derivative value and the absolute value of the donor derivative value at the point.

Figure 20A:
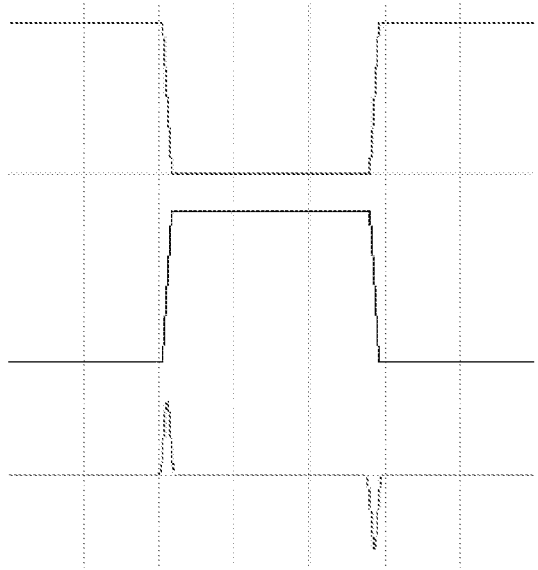
FIG. 20a depicts derivative anti-correlation for simulated non-noisy data.
Figure 20A:
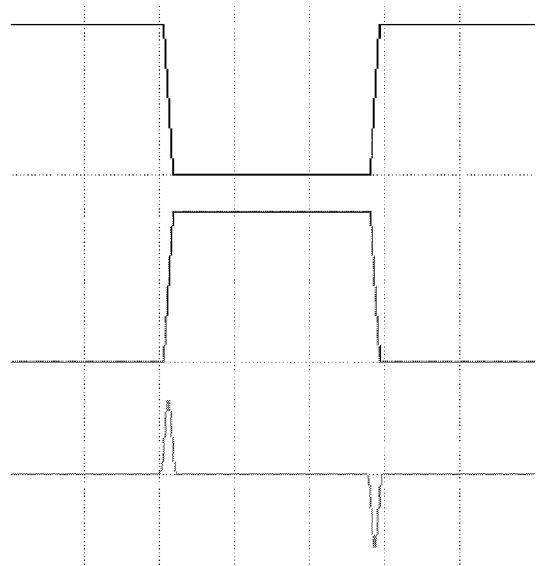

Referring now to FIGS. 20*a* and 20*a*', an example of the derivative anti-correlation methodology is illustrated graphically for ideal, non-noisy anti-correlated data. In the top panel, a simulated donor trace having an intensity dip in the middle of the trace is shown. In the center panel, a simulated acceptor trace having an intensity bump, anti-correlated with the donor dip is shown. In the bottom panel, the DAC values for the above signals are shown. The positive peak marks the start of an anti-correlated event, and the negative peak marks the end of the anti-correlated event.

Figure 20B:
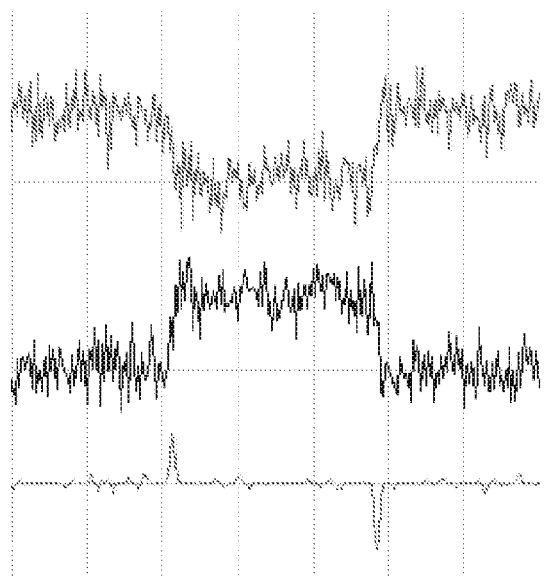
FIG. 20b depicts derivative anti-correlation of simulated moderately noisy data.
Figure 20B:
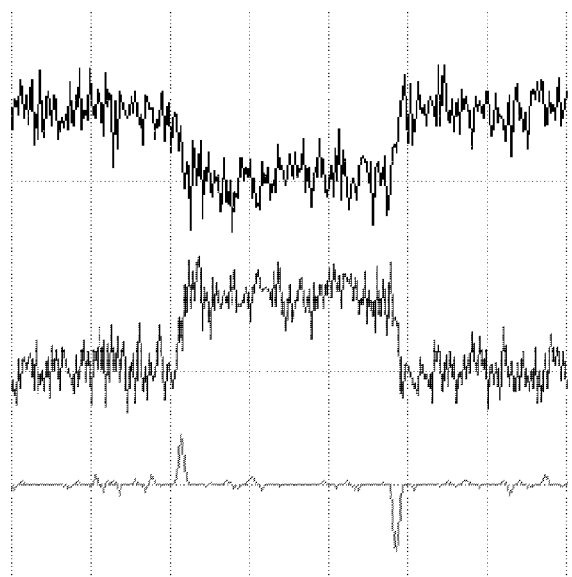

Referring now to FIGS. 20*b* and 20*b*', an example of the derivative anti-correlation methodology is illustrated graphically for moderately noisy data. In the data having a moderate noise level, the peaks are well above the standard deviation of the DAC function, so the DAC helps to detect even short anti-correlated events, that would be otherwise undetected.

Figure 20C:
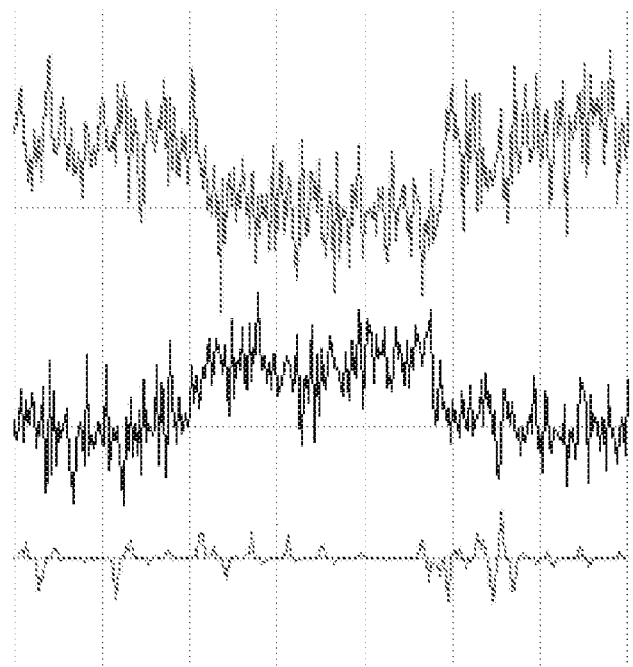
FIG. 20c derivative anti-correlation of simulated heavily noisy data.
Figure 20C:
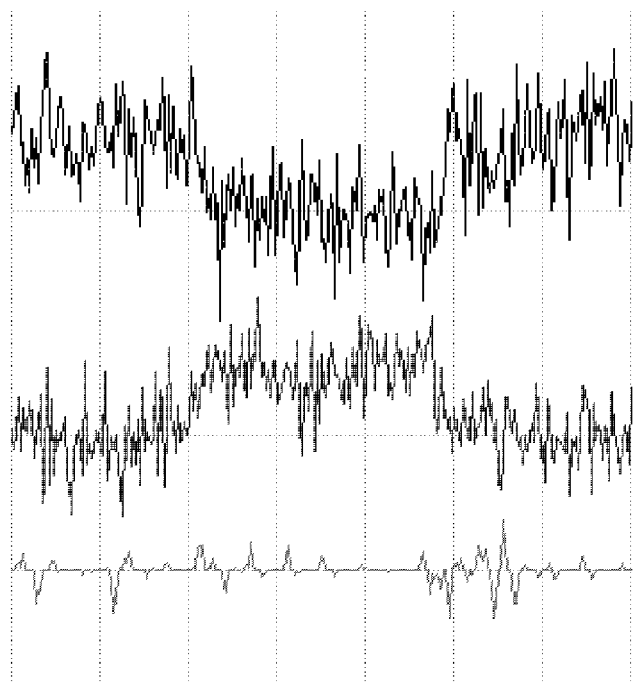

Referring now to FIGS. 20*c* and 20*c*', an example of the derivative anti-correlation methodology is illustrated graphically for heavily noisy data. If the noise level is too high, the DAC is unable to detect anti-correlated events, because the peaks are comparable to the standard deviation of the noise level. Short events become very difficult to detect, while long events are detected by other means, such as heavy data smoothing and analyzing average signal intensities over long periods of time.

Because the final goal of the detection software is to detect anti-correlated events, when a dip in the donor signal intensity occurs synchronously with a bump in an acceptor signal intensity, the DAC is effective even for short signals, provided that their shape is not too much distorted or attenuated by the noise level.

Smart Smoothing Algorithm

A standard Savitzky-Golay (S-G) smoothing filter (as described above) does not produce satisfactory results for heavily-noisy data, even if it contains some obvious long-lived signals. An S-G filter designed for heavy smoothing (e.g., larger number of samples, lower polynomial order), while removing enough noise, distorts the boundaries of the rectangular-shaped signals, making it nearly impossible to detect the correct boundaries. Also, the filter tends to lose shorter signals.

An S-G filter, designed for fine smoothing (e.g., smaller number of samples, higher polynomial order), on the other hand, tends to leave a great deal of noise, which can break down large signals into series of smaller ones, and also create many false positives in between the real signals.

The principal idea of the smart smoother of this invention is to balance the two S-G filters so that on flat segments, the heavy smoother takes precedence, removing most of the noise, while in areas where the intensity is rapidly changing, the fine smoother is invoked, preserving the exact signal boundaries, critical for detecting anti-correlated spFRET signals.

The balance function b is computed out of the derivative D of the original data, computed with an S-G filter with the settings somewhere in the middle between the settings for heavy smoother and fine smoother. For example, if the heavy smoother has nL=nR=32 and M=2 and the fine smoother has nL=nR=8 and M=6, then the derivative filter would have nL=nR=16 and M=4.

The next step is to convert the derivative, a function that theoretically ranges from $-\infty$ to $+\infty$, into a balance function, which ranges from zero (0) to one (1), where the balance function has the value of zero (0) when the derivative is zero, and the value of one (1) when the derivative goes to infinity in either direction.

The balance function b is computed as:

$$b_i = 1 - \exp(-F_i^2 / \text{Var}),$$

where Var is the variance given by $\Sigma F_i^2 / n$, where n is the total number of data samples.

After that, the balance function is smoothed with the same "middle" S-G parameters, as the ones for derivative. After the smoothing, values of the balance function may be out of range zero to one at a few points, so an additional process is applied to force the values within the zero to one boundaries. The resulting balance function is shown in the middle panel in FIG. 21 comprising a solid curve with a shaded area below the curve (light-red in a color image) and a shaded area above the curve (light-blue in a color image).

Figure 21:
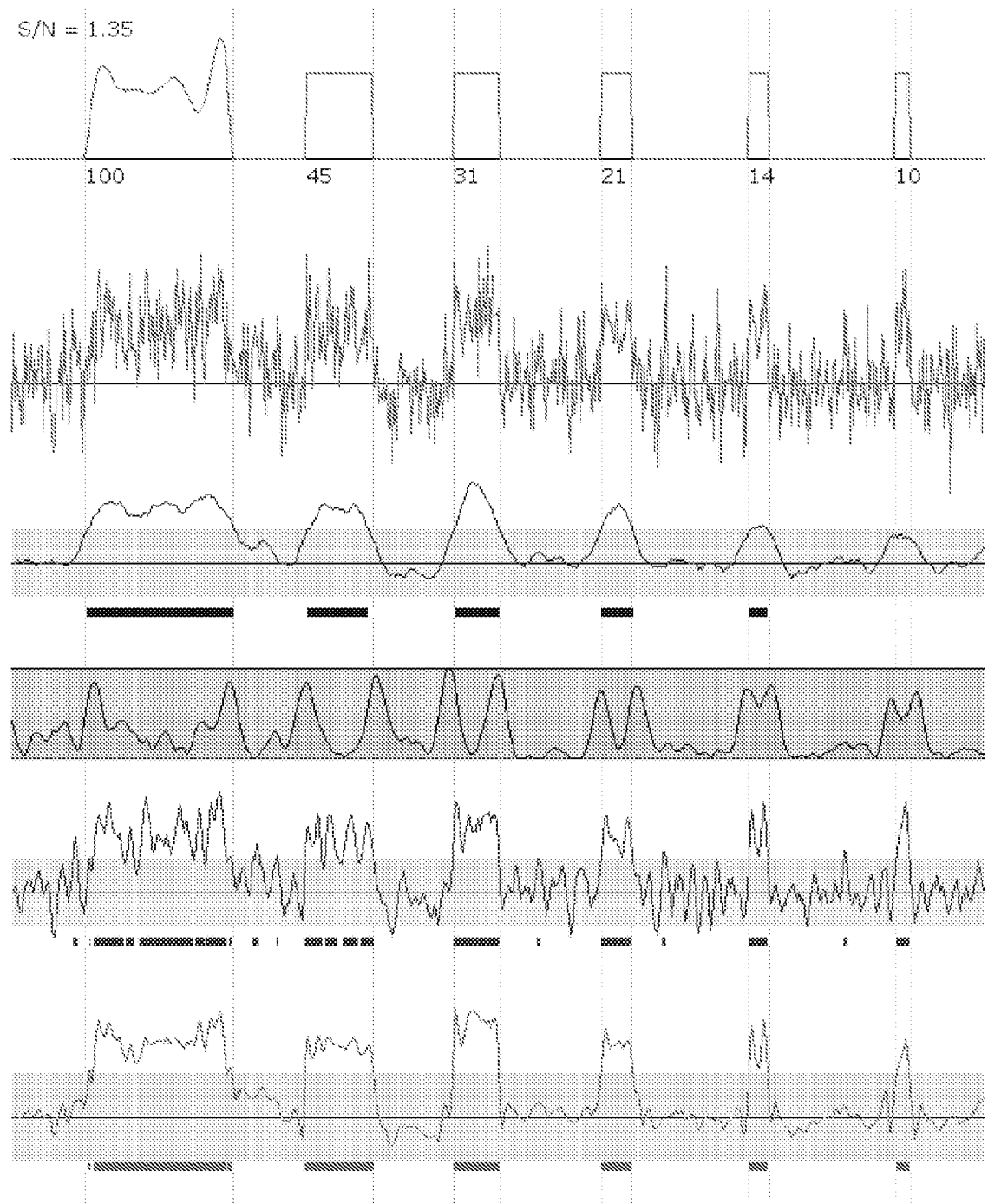
FIG. 21 depicts a smart smoothing process.

Looking at FIG. 21, the top three panels represent a simulated data trace. The top most panel comprising six high intensity bumps of different lengths with the length shown below the bumps having a SN of 1.35. The next panel represents the simulated data trace with Gaussian noise. The next panel represent the noisy data trace atter Savitzky-Golay filter having nL=32,nR=32,M=4. The gray bar about the solid zero line denotes the noise level, computed as standard deviation of a separate noise-only trace, generated with the same settings as used with the original signal. The solid horizontal bars below the gray area represent the data segments of the smoothed curve, i.e, the segments of the curve that have values above the gray bar. The next panel is a graph of the balance function ranging from 0 to 1, computed from the derivative of the noisy signal, second panel from top, obtained by a Savitzky-Golay process with nL=16, nR=16, M=4. The next panel***; e) Red graph. Noisy signal (b) after Savitzky-Golay filter with nL=8,nR=8, M=6. Grey area is the noise level, same as in (c). Red bars below is the lifetime, similar to (c); f) Green graph. Smart-smoothed signal, the combined signal. computed as b*Fs+ (I-b)*Fr, where Fs is the light-smoothed data (e),Fr is the heavy-smoothed data (c),b is the balance function (d). Grey area is the noise level. (same as above), green bars below is the lifetime.

The last step is just to compute "balanced" function as:

$$Fsm_i = Fs_i * b_i + Fr_i * (1 - b_i),$$

where Fs is the fine smoothed data, Fr is the heavy smoothed data, and the result Fsm is the smart smoothed data.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

What is claimed is:

1. A method for detecting and analyzing events at the single molecule level, where the method comprising the steps of:
   collecting data corresponding to changes in a detectable property of a detectable entity in a sample over time within a viewing volume or field of a detection system, where the data comprises a collection of data frames associated with a plurality of data channels, where the data channels represent different features of the detectable property, and where each frame is an image of the viewing field over a data collection interval comprising a set of data elements representable in a column row matrix format, and where the detectable entity is selected from the group consisting of an atom, a molecule, an ion, an assemblage of atoms, molecules and/or ions, a plurality of atoms, a plurality of molecules, a plurality of ions, and/or a plurality of assemblages,
   forwarding the data frames to a processing unit, where the data frames are stored along with data associated with the detection of the detectable property including sample data, time/data and detector data,
   generating a calibration transformation adapted to register data elements in one data channel with corresponding data elements in the other data channels,
   averaging a value of the detectable property for each data element over all of the frames from one data channel to produce an averaged image, where each data element in the averaged image includes the average value of detectable property across all the frames,
   identifying data elements in the averaged images having a value of the detectable property above a threshold value to produce a list of potential active entity candidates,
   retrieving and storing candidate data traces, one trace for each data element in a n×n data element array centered at each identified candidate,
   retrieving and storing noise data traces from a plurality of data elements within an m×m data element array centered at each identified candidate excluding the data elements of the n×n array, where the noise data traces represent local noise associated with each candidate,
   filtering the candidates to find candidates that satisfy a set of selection criteria or passing a set of rejection criteria,
   retrieving and storing other channel data traces, one trace for each data element in a n×n data element array centered at data element of the other data channels corresponding to the candidate, retrieving and storing other channel noise data traces from a plurality of data elements within an m×m data element array centered at data element of the other data channels corresponding to the candidate excluding the data elements of the n×n array, where the noise data traces represent local noise associated with other data channels, smoothing the traces and forming hybrid traces, one hybrid trace for each candidate, for each candidate noise, for each other channel corresponding candidate data and for each other channel noise data, identifying hybrid traces that evidence correlated or anti-correlated changes in the detectable property for the candidate traces and the corresponding other channel traces to produce an event list, classifying the event list into a class of events, and storing the classified list of events.

2. The method of claim 1, wherein at least one component of the entities include a fluorophore and the detectable property is fluorescence.

3. The method of claim 1, wherein at least one component of the entities include a donor fluorophore, at least one component of the entities include an acceptor fluorophore and the detectable property is fluorescence derived from fluorescence resonance energy transfer (FRET).

4. The method of claim 1, wherein each detectable entity comprises replication complex including a polymerase, a template, a primer and nucleotides for the polymerase, where the polymerase, template, and/or primer includes a donor fluorophore and at least two nucleotide types including acceptor fluorophores forming a fluorescence resonance energy transfer (FRET) pair, where the acceptor fluorophores are the same or different, and the detectable property is fluorescence derived from fluorescence resonance energy transfer (FRET).

5. The method of claim 4, where the identified hybrid traces are anti-correlated.

6. The method of claim 1, wherein each detectable entity comprises replication complex including a polymerase, a template, a primer and nucleotides for the polymerase, where the polymerase, template, and/or primer includes a donor fluorophore and at least one nucleotide type including an acceptor fluorophore forming a fluorescence resonance energy transfer (FRET) pair and the detectable property is fluorescence derived from fluorescence resonance energy transfer (FRET).

7. The method of claim 6, where the identified hybrid traces are anti-correlated.

8. The method of claim 6, where the acceptor fluorophores are bonded to a part of the nucleotide that is released during nucleotide incorporation due to action of the polymerase.

9. A method for detecting and analyzing events at the single molecule level, where the method comprising the steps of:

collecting data corresponding to changes in a detectable property of a detectable entity in a sample comprising at least one replication complex including a polymerase, a template, a primer and nucleotide types for the polymerase, where the polymerase, template, and/or primer includes a donor fluorophore and at least one nucleotide types includes an acceptor fluorophore and where the donor fluorophore and the acceptor fluorophore form a fluorescence resonance energy transfer (FRET) pair, where the acceptor fluorophores are the same or different, and the detectable property is fluorescence derived from fluorescence resonance energy transfer over time within a viewing volume or field of a detection system, where the data comprises a collection of data frames associated with a plurality of data channels, where the data channels represent different features of the detectable property, and where each frame is an image of the viewing field over a data collection interval comprising a set of data elements representable in a column row matrix format, and where the detectable entity is selected from the group consisting of an atom, a molecule, an ion, an assemblage of atoms, molecules and/or ions, a plurality of atoms, a plurality of molecules, a plurality of ions, and/or a plurality of assemblages, forwarding the data frames to a processing unit, where the data frames are stored along with data associated with the detection of the detectable property including sample data, time/data and detector data, generating a calibration transformation adapted to register data elements in one data channel with corresponding data elements in the other data channels, averaging a value of the detectable property for each data element over all of the frames from one data channel to produce an averaged image, where each data element in the averaged image includes the average value of detectable property across all the frames, identifying data elements in the averaged images having a value of the detectable property above a threshold value to produce a list of potential active entity candidates, retrieving and storing candidate data traces, one trace for each data element in a n×n data element array centered at each identified candidate, retrieving and storing noise data traces from a plurality of data elements within an m×m data element array centered at each identified candidate excluding the data elements of the n×n array, where the noise data traces represent local noise associated with each candidate, filtering the candidates to find candidates that satisfy a set of selection criteria or passing a set of rejection criteria, retrieving and storing other channel data traces, one trace for each data element in a n×n data element array centered at data element of the other data channels corresponding to the candidate, retrieving and storing other channel noise data traces from a plurality of data elements within an m×m data element array centered at data element of the other data channels corresponding to the candidate excluding the data elements of the n×n array, where the noise data traces represent local noise associated with other data channels, smoothing the traces and forming hybrid traces, one hybrid trace for each candidate, for each candidate noise, for each other channel corresponding candidate data and for each other channel noise data, identifying hybrid traces that evidence correlated or anti-correlated changes in the detectable property for the candidate traces and the corresponding other channel traces to produce an event list, classifying the event list into a class of events, and storing the classified list of events.

10. The method of claim 9, where the identified hybrid traces are anti-correlated.

11. The method of claim 9, where the acceptor fluorophores are bonded to a part of the nucleotide that is released during nucleotide incorporation due to action of the polymerase.

12. The method of claim 9, wherein the replication complexes further include at least two nucleotide types including acceptor fluorophores forming a fluorescence resonance energy transfer (FRET) pairs with the donor fluorophore, where the acceptor fluorophores are the same or different.

13. The method of claim 12, where the identified hybrid traces are anti-correlated.

14. The method of claim 9, wherein at least three of the nucleotide types including acceptor fluorophores forming fluorescence resonance energy transfer (FRET) pairs with the donor fluorophore, where the acceptor fluorophores are the same or different.

15. The method of claim 14, where the identified hybrid traces are anti-correlated.

16. The method of claim 9, wherein each nucleotide type including acceptor fluorophores forming a FRET pairs with the donor fluorophore, where the acceptor fluorophores are the same or different.

17. The method of claim 16, where the identified hybrid traces are anti-correlated.

18. A method for detecting and analyzing events at the single molecule level, where the method comprising the steps of:
  collecting data corresponding to fluorescence derived from fluorescence resonance energy transfer (FRET) over time within a viewing volume or field of a detection system at least one detectable entity including an acceptor fluorophore and a donor fluorophore, which form a fluorescence resonance energy transfer (FRET) pair, where the data comprises a collection of data frames associated with a plurality of data channels, where the data channels represent different features of the fluorescence, and where each frame is an image of the viewing field over a data collection interval comprising a set of data elements representable in a column row matrix format, and where the detectable entity is selected from the group consisting of an atom, a molecule, an ion, an assemblage of atoms, molecules and/or ions, a plurality of atoms, a plurality of molecules, a plurality of ions, and/or a plurality of assemblages,
  forwarding the data frames to a processing unit, where the data frames are stored along with data associated with the detection of the detectable property including sample data, lime/data and detector data,
  generating a calibration transformation adapted to register data elements in one data channel with corresponding data elements in the other data channels,
  averaging a value of the detectable property for each data element over all of the frames from one data channel to produce an averaged image, where each data element in the averaged image includes the average value of detectable property across all the frames,
  identifying data elements in the averaged images having a value of the detectable property above a threshold value to produce a list of potential active entity candidates,
  retrieving and storing candidate data traces, one trace for each data element in a n×n data element array centered at each identified candidate,
  retrieving and storing noise data traces from a plurality of data elements within an m×m data element array centered at each identified candidate excluding the data elements of the n×n array, where the noise data traces represent local noise associated with each candidate,
  filtering the candidates to find candidates that satisfy a set of selection criteria or passing a set of rejection criteria,
  retrieving and storing other channel data traces, one trace for each data element in a n×n data element array centered at data element of the other data channels corresponding to the candidate,
  retrieving and storing other channel noise data traces from a plurality of data elements within an m×m data element array centered at data element of the other data channels corresponding to the candidate excluding the data elements of the n×n array, where the noise data traces represent local noise associated with other data channels,
  smoothing the traces and forming hybrid traces, one hybrid trace for each candidate, for each candidate noise, for each other channel corresponding candidate data and for each other channel noise data,
  identifying hybrid traces that evidence correlated or anti-correlated changes in the detectable property for the candidate traces and the corresponding other channel traces to produce an event list,
  classifying the event list into a class of events, and
  storing the classified list of events.

19. The method of claim 18, wherein at least one component of the entities include a donor fluorophore, at least one component of the entities include an acceptor fluorophore and the detectable property is fluorescence derived from fluorescence resonance energy transfer.

20. The method of claim 18, where the acceptor fluorophores are bonded to a part of the nucleotide that is released during nucleotide incorporation due to action of the polymerase.

21. The method of claim 18, wherein each detectable entity comprises replication complex including a polymerase, a template, a primer and nucleotides for the polymerase, where the polymerase, template, and/or primer includes a donor fluorophore and at least one nucleotide type including an acceptor fluorophore forming a FRET pair with the donor fluorophore.

22. The method of claim 21, where the identified hybrid traces are anti-correlated.

23. The method of claim 18, wherein each detectable entity comprises replication complex including a polymerase, a template, a primer and nucleotides for the polymerase, where the polymerase, template, and/or primer includes a donor fluorophore and at least two nucleotide types including acceptor fluorophores forming a FRET pair with the donor fluorophore and where the acceptor fluorophores are the same or different.

24. The method of claim 23, where the identified hybrid traces are anti-correlated.

25. The method of claim 18, wherein each detectable entity comprises replication complex including a polymerase, a template, a primer and nucleotides forte polymerase, where the polymerase, template, and/or primer includes a donor fluorophore and at least three nucleotide types including acceptor fluorophores forming a FRET pair with the donor fluorophore and where the acceptor fluorophores are the same or different.

26. The method of claim 25, where the identified hybrid traces are anti-correlated.

27. The method of claim 18, wherein each detectable entity comprises replication complex including a polymerase, a template, a primer and nucleotides for the polymerase, where the polymerase, template, and/or primer includes a donor fluorophore and all four nucleotide types including acceptor fluorophores forming a FRET pair with the donor fluorophore and where the acceptor fluorophores are the same or different.

28. The method of claim 27, where the identified hybrid traces are anti-correlated.

* * * * *